(12) United States Patent
Miller

(10) Patent No.: US 9,133,182 B2
(45) Date of Patent: Sep. 15, 2015

(54) SELECTIVE ANDROGEN RECEPTOR MODULATORS

(75) Inventor: Chris P. Miller, Cambridge, MA (US)

(73) Assignee: Radius Health, Inc., Waltham, MA (US)

( * ) Notice: Subject to any disclaimer, the term of this patent is extended or adjusted under 35 U.S.C. 154(b) by 58 days.

(21) Appl. No.: 13/876,809

(22) PCT Filed: Sep. 27, 2011

(86) PCT No.: PCT/US2011/053375
§ 371 (c)(1),
(2), (4) Date: Mar. 28, 2013

(87) PCT Pub. No.: WO2012/047617
PCT Pub. Date: Apr. 12, 2012

(65) Prior Publication Data
US 2013/0217732 A1   Aug. 22, 2013

Related U.S. Application Data

(60) Provisional application No. 61/387,440, filed on Sep. 28, 2010.

(51) Int. Cl.
*C07D 417/10* (2006.01)
*C07D 263/24* (2006.01)
*C07D 233/36* (2006.01)
*C07D 207/26* (2006.01)
*C07D 417/04* (2006.01)

(52) U.S. Cl.
CPC ............ *C07D 417/10* (2013.01); *C07D 207/26* (2013.01); *C07D 233/36* (2013.01); *C07D 263/24* (2013.01); *C07D 417/04* (2013.01)

(58) Field of Classification Search
None
See application file for complete search history.

(56) References Cited

U.S. PATENT DOCUMENTS

| | | | |
|---|---|---|---|
| 5,411,981 A | 5/1995 | Gaillard-Kelly et al. | |
| 6,156,899 A | 12/2000 | Galey et al. | |
| 6,159,959 A | 12/2000 | Miller | |
| 6,960,474 B2 | 11/2005 | Salvati et al. | |
| 7,446,110 B2 | 11/2008 | Kaufman et al. | |
| 7,968,580 B2 * | 6/2011 | Lanter et al. | 514/386 |
| 8,067,448 B2 | 11/2011 | Miller | |
| 8,268,872 B2 | 9/2012 | Miller | |
| 8,455,525 B2 | 6/2013 | Miller | |
| 8,629,167 B2 | 1/2014 | Miller | |
| 8,642,632 B2 | 2/2014 | Miller | |
| 2005/0182105 A1 | 8/2005 | Nirschl et al. | |
| 2005/0250749 A1 | 11/2005 | Labrie et al. | |
| 2005/0261303 A1 | 11/2005 | Taniguchi et al. | |
| 2006/0106067 A1 | 5/2006 | Shiraishi et al. | |
| 2006/0116415 A1 | 6/2006 | Sui et al. | |
| 2006/0142387 A1 | 6/2006 | Cadilla et al. | |
| 2006/0148893 A1 | 7/2006 | Blanc et al. | |
| 2006/0211756 A1 | 9/2006 | Zhang et al. | |
| 2006/0287327 A1 | 12/2006 | Labrie et al. | |
| 2007/0088039 A1 | 4/2007 | Balog et al. | |
| 2007/0254875 A1 | 11/2007 | Zhi et al. | |
| 2007/0281906 A1 | 12/2007 | Dalton et al. | |
| 2008/0057068 A1 | 3/2008 | Dalton et al. | |
| 2009/0042866 A1 | 2/2009 | Lennox et al. | |
| 2009/0042967 A1 | 2/2009 | Hasuoka | |
| 2009/0253758 A1 | 10/2009 | Miller | |
| 2009/0264534 A1 | 10/2009 | Dalton et al. | |
| 2010/0041721 A1 | 2/2010 | Miller | |
| 2010/0152236 A1 | 6/2010 | Yamamoto et al. | |
| 2011/0224267 A1 | 9/2011 | Miller | |
| 2012/0004270 A1 | 1/2012 | Miller | |
| 2013/0041007 A1 | 2/2013 | Miller | |
| 2013/0116288 A1 | 5/2013 | Miller | |

FOREIGN PATENT DOCUMENTS

| | | |
|---|---|---|
| EP | 0 916 652 | 5/1999 |
| EP | 0 580 459 B1 | 3/2001 |
| EP | 1 911 743 A1 | 4/2008 |
| GB | 1 547 758 A | 6/1979 |
| JP | 60-16957 A | 1/1985 |
| JP | 01-261381 A | 10/1989 |
| WO | WO 94/27989 A1 | 12/1994 |
| WO | WO 96/41793 A1 | 12/1996 |
| WO | WO 97/49709 A1 | 12/1997 |
| WO | WO 02/16310 A1 | 2/2002 |
| WO | WO 03/011824 A1 | 2/2003 |
| WO | WO 03/068217 A1 | 8/2003 |
| WO | WO 03/096980 A2 | 11/2003 |
| WO | WO 2004/041277 A1 | 5/2004 |
| WO | WO 2004/041782 A1 | 5/2004 |
| WO | WO 2004/045518 A2 | 6/2004 |
| WO | WO 2004/080377 A2 | 9/2004 |
| WO | WO 2004/110978 A2 | 12/2004 |
| WO | WO 2005/000309 A2 | 1/2005 |
| WO | WO 2005/000794 A1 | 1/2005 |
| WO | WO 2005/000795 A2 | 1/2005 |

(Continued)

OTHER PUBLICATIONS

Acevedo, S., et al., "Selective Androgen Receptor Modulators Antagonize Apolipoprotein E4-Induced Cognitive Impairments," *Letters in Drug Design & Discovery*, 5: 271-276 (2008).

(Continued)

*Primary Examiner* — Kamal Saeed

(74) *Attorney, Agent, or Firm* — Perkins Coie LLP; Yingli Wang

(57) ABSTRACT

This invention provides compounds of formula I, pharmaceutical compositions comprising a compound of formula I and a pharmaceutically acceptable excipient, methods of modulating the androgen receptor, methods of treating diseases beneficially treated by an androgen receptor modulator (e.g., sarcopenia, prostate cancer, contraception, type 2 diabetes related disorders or diseases, anemia, depression, and renal disease) and processes for making compounds and intermediates useful in the preparation of same.

18 Claims, No Drawings

(56) References Cited

FOREIGN PATENT DOCUMENTS

| | | |
|---|---|---|
| WO | WO 2005/040136 A1 | 5/2005 |
| WO | WO 2005/042464 A1 | 5/2005 |
| WO | WO 2005/049574 A1 | 6/2005 |
| WO | WO 2005/049580 A1 | 6/2005 |
| WO | WO 2005/060956 A1 | 7/2005 |
| WO | WO 2005/077925 A1 | 8/2005 |
| WO | WO 2005/085185 A1 | 9/2005 |
| WO | WO 2005/086735 A2 | 9/2005 |
| WO | WO 2005/087232 A1 | 9/2005 |
| WO | WO 2005/089118 A2 | 9/2005 |
| WO | WO 2005/090282 A1 | 9/2005 |
| WO | WO 2005/090328 A1 | 9/2005 |
| WO | WO 2005/094810 A2 | 10/2005 |
| WO | WO 2005/099707 A1 | 10/2005 |
| WO | WO 2005/102998 A1 | 11/2005 |
| WO | WO 2005/108351 A1 | 11/2005 |
| WO | WO 2005/111028 A1 | 11/2005 |
| WO | WO 2005/115361 A2 | 12/2005 |
| WO | WO 2005/116001 A1 | 12/2005 |
| WO | WO 2005/120483 A2 | 12/2005 |
| WO | WO 2006/031715 A1 | 3/2006 |
| WO | WO 2006/039243 A1 | 4/2006 |
| WO | WO 2006/044359 A2 | 4/2006 |
| WO | WO 2006/044707 A1 | 4/2006 |
| WO | WO 2006/055184 A2 | 5/2006 |
| WO | WO 2006/060108 A1 | 6/2006 |
| WO | WO 2006/076317 A2 | 7/2006 |
| WO | WO 2006/113552 A2 | 10/2006 |
| WO | WO 2006/124447 A2 | 11/2006 |
| WO | WO 2006/133216 A2 | 12/2006 |
| WO | WO 2007/002181 A2 | 1/2007 |
| WO | WO 2007/005887 A2 | 1/2007 |
| WO | WO 2007/015567 A1 | 2/2007 |
| WO | WO 2007/034846 A1 | 3/2007 |
| WO | WO 2007/067490 A1 | 6/2007 |
| WO | WO 2007/087518 A2 | 8/2007 |
| WO | WO 2007/099200 A1 | 9/2007 |
| WO | WO 2007/146914 A1 | 12/2007 |
| WO | WO 2008/008433 A2 | 1/2008 |
| WO | WO 2008/011072 A2 | 1/2008 |
| WO | WO 2008/011073 A1 | 1/2008 |
| WO | WO 2008/024456 A2 | 2/2008 |
| WO | WO 2008/042571 A2 | 4/2008 |
| WO | WO 2008/044033 | 4/2008 |
| WO | WO 2008/063867 A2 | 5/2008 |
| WO | WO 2008/121602 A1 | 10/2008 |
| WO | WO 2008/124000 A2 | 10/2008 |
| WO | WO 2008/124922 A1 | 10/2008 |
| WO | WO 2008/127717 A1 | 10/2008 |
| WO | WO 2008/128100 A1 | 10/2008 |
| WO | WO 2009/020234 A2 | 2/2009 |
| WO | WO 2009/065600 A2 | 5/2009 |
| WO | WO 2009/081197 A1 | 7/2009 |
| WO | WO 2009/082437 A2 | 7/2009 |
| WO | WO 2009/105214 A2 | 8/2009 |
| WO | WO 2009/133861 A1 | 11/2009 |
| WO | WO 2009/140448 A1 | 11/2009 |
| WO | WO 2010/118287 | 10/2010 |
| WO | WO 2011/097496 | 8/2011 |
| WO | WO 2012/047617 | 4/2012 |

OTHER PUBLICATIONS

Allan G. F., et al., "A Selective Androgen Receptor Modulator with Minimal Prostate Hypertrophic Activity Enhances Lean Body Mass in Male Rats and Stimulates Sexual Behavior in Female Rats," *Endocr.*, 32: 41-51 (2007).

Allan, G., et al., "A Selective Androgen Receptor Modulator that Reduces Prostate Tumor Size and Prevents Orchidectomy-Induced Bone Loss in Rats," *Journal of Steroid Biochemistry & Molecular Biology*, 103: 76-83 (2007).

Anderson, A.C., "The Process of Structure-Based Drug Design," *Chem and Biol*, 10: 787-797 (Sep. 2003).

Autoimmune disorders: MedlinePlus Medical Encyclopedia [online], [retrieved on Jun. 3, 2011]. Retrieved from the Internet URL: http://www.nlm.nih.gov/medlineplus/ency/article/000816.htm.

Bohl, C. E., "Structural Basis for Antagonism and Resistance of Bicalutamide in Prostate Cancer," *PNAS*, 102 (17): 6201-6206 (2005).

Bohl, C.E., et al., "Structural Basis for Accommodation of Nonsteroidal Ligands in the Androgen Receptors," *The Journal of Biological Chemistry*, 280 (45): 37747-37754 (Nov. 11, 2005).

Browne, "Stable Isotopes in Pharamaceutical Research," *Pharmacochemistry Library*, 26: 13-18(1997).

Cantin, L., et al., "Structural Characterization of the Human Androgen Receptor Ligand-Binding Domain Complexed with EM5744, a Rationally Designed Steroidal Ligand Bearing a Bulky Chain Directed Toward Helix 12," *Journal of Biological Chemistry*, 282 (42): 30910-309.19 (Oct. 19, 2007).

"deuterium." In http://www.britannica.com. Retrieved Feb. 18, 2009 from <http://www.britannica.com/Ebchecked/topic/159684/deuterium>.

Gao, W., et al., "Comparison of the Pharmacological Effects of a Novel Selective Androgen Receptor Modulator, the 5α-Reductase Inhibitor Finasteride, and the Antiandrogen Hydroxyflutamide in Intact Rats: New Approach for Benign Prostate Hyperplasia," *Endocrinology*, 145 (12): 5420-5428 (Dec. 2004).

Gao, W., et al., "Expanding the Therapeutic use of Androgens via Selective Androgen Receptor Modulators (SARMs)," *Drug Discovery Today*, 12: 241-248 (Mar. 2007).

Gao, W., et al., "Ockham's Razor and Selective Androgen Receptor Modulators (SARMs): Are we Overlooking the Role of 5α-Reductase?", *Molecular Interventions*, 7: 10-13 (Feb. 2007).

Gao, W., et al., "Selective Androgen Receptor Modulator (SARM) Treatment Improves Muscle Strength," *Endocrinology*, doi:10.1210/en.2005-0572, pp. 1-37 (Aug. 11, 2005).

Gao, W., et al., "Selective Androgen Receptor Modulator Treatment Improves Muscle Strength and Body Composition and Prevents Bone Loss in Orchidectomized Rats," *Endocrinology*, 146 (II): 4887-4897 (Nov. 2005).

Hamann, L. G., "Discovery and Preclinical Profile of a Highly Potent and Muscle Selective Androgen Receptor Modulator (SARM)," *227th National Meeting of the American Chemical Society Medicinal Chemistry Division*, Mar. 28, 2004, Anaheim, CA.

Hamann, L.G., et al., "Tandem Optimization of Target Activity and Elimination of Mutagenic Potential in a Potent Series of N-aryl Bicyclic Hydantoin-Based Selective Androgen Receptor Modulators," *Bioorganic & Medicinal Chemistry Letters*, 17: 1860-1864 (2007).

Hanada, K., et al. "Bone Anabolic Effects of S-40503, a Novel Nonsteroidal Selective Androgen Receptor Modulator (SARM), in Rat Models of Osteoporosis," *Biol. Pharm. Bull.*, 26(11): 1563-1569 (Nov. 2003).

Higuchi, R. I., et al., "Novel Series of Potent, Nonsteroidal, Selective Androgen Receptor Modulators Based on 7 H-[1,4]Oxazino[3,2-g]quinolin-7-ones," *J. Med. Chem.*, 50(10): 2486-2496 (2007).

Horig, H. and Pullman, W., "From Bench to Clinic and Back: Perspective on the 1st IQPC Translational Research Conference," *Journal of Translational Medicine* 2(44):1-8 (2004).

Hwang, D. J., et al., "Arylisothiocyanato Selective Androgen Receptor Modulators (SARMs) for Prostate Cancer," *Bioorganic & Medicinal Chemistry*, 14: 6525-6538 (2006).

Kemppainen, J. A., et al., "Distinguishing Androgen Receptor Agonists and Antagonists: Distinct Mechanisms of Activation by Medroxyprogesterone Acetate and Dihydrotestosterone," *Molecular Endocrinology*, 13: 440-454 (1999).

Kilbourne, E. J., et al., "Selective Androgen Receptor Modulators for Frailty and Osteoporosis," *Current Opinion in Investigational Drugs*, 8(10): 821-829 (2007).

Kim, J., et al., "The 4-Para Substituent of S-3-(phenoxy)-2-hydroxy-2-methyl-N-(4-nitro-3-triflurormethyl-phenyl)-propionamides is a Major Structural Determinant of In Vivo Disposition and Activity of Selective Androgen Receptor Modulators," *JPET* #88344, DOI:10.1124/jpet.105.088344, 42 pages (Jun. 29, 2005).

(56) References Cited

OTHER PUBLICATIONS

Kinoyama, I., et al., "(+)-(2R,5S)-4-[4-Cyano-3-(trifluoromethyl)phenyl]-2,5-dimethyl-N-[6-(trifluoromethyl)pyridin-3-yl]piperazine-1-carboxamide (YM580) as an Orally Potent and Peripherally Selective Nonsteroidal Androgen Receptor Antagonist," *J. Med. Chem.* 49(2): 716-726 (2006).
Lanter, J. C., et al., "The Discovery of a Potent Orally Efficacious Indole Androgen Receptor Antagonist Through in vivo Screening," *Bioorganic & Medicinal Chemistiy Letters*, 17: 123-126 (2007).
Martinborough, E., et al., "Substituted 6-(1-(Pyrrolidine)quinolin-2(1H)-ones as Novel Selective Androgen Receptor Modulators," *J. Med. Chem.* 50(21): 5049-5052 (Oct. 18, 2007).
McGinley, P. L., et al., "Circumventing Anti-Androgen Resistance by Molecular Design," *J. Am. Chem. Soc.*, 129: 3822-3823 (2007).
Miller, C. P., et al., "Design, Synthesis, and Preclinical Characterization of the Selective Androgen Receptor Modulator (SARM) RAD140," ACS Med. Chem. Lett., 2(2): 124-129, DOI: 10.1021/ml1002508 (Dec. 2, 2010).
Miller, C.P., et al., "Synthesis of Potent, Substituted Carbazoles as Selective Androgen Receptor Modulators (SARMs)," *Bioorg. Med. Chem. Lett.*, 20: 7516-7520 (2010).
Mitchell, H. J., et al., Design, Synthesis, and Biological Evaluation of 16-Substituted 4-Azasteroids as Tissue-Selective Androgen Receptor Modulators (SARMs), *J. Med. Chem.*, 52(15): 4578-81 (2009).
Mohler, M. L., et al., "Nonsteroidal Selective Androgen Receptor Modulators (SARMs): Dissociating the Anabolic and Androgenic Activities of the Androgen Receptor for Therapeutic Benefit," *J. Med Chem.*, 52(12): 3597-617 (Jun. 25, 2009).
Morris, J. J., et al., "Non-steroidal Antiandrogens. Design of Novel Compounds Based on an Infrared Study of the Dominant Conformation and Hydrogen-Bonding Properties of a Series of Anilide Antiandrogens," *J. Med. Chem.*, 34: 447-155 (1991).
Ng, R.A.,"Synthesis and SAR of Potent and Selective Androgen Receptor Antagonists: 5,6-Dicholoro-benzimidazole Derivatives," *Bioorganic & Medicinal Chemistry Letters*, 17: 784-788 (2007).
Ng, R. A., "Synthesis of Potent and Tissue-Selective Androgen Receptor Modulators (SARMs): 2-(2,2,2)-Trifluoroethyl-benzimidazole Scaffold," *Bioorganic & Medicinal Chemistry Letters*, 17: 1784-1787 (2007).
Obinata, R. et al., "Stereodivergent Constructiion of Aminidiols with CF3 Group," *Organic Letters* 12 (19):4316-4319 (2010).
Ostrowski, J., et al., "Pharmacological and X-Ray Structural Characterization of a Novel Selective Androgen Receptor Modulator: Potent Hyperanabolic Stimulation of Skeletal Muscle with Hypostimulation of Prostate in Rats," *Endocrinology*, 148(1): 4-12 (Jan. 2007).
Piu, F., et al., "Pharmacological Characterization of AC-262536, A Novel Selective Androgen Receptor Modulator," *Journal of Steroid Biochemistry & Molecular Biology*, 109: 129-137 (2008).
Riedmaier, et al., "Influence of Testosterone and a Novel SARM on Gene Expression in Whole Blood of Macaca Fascicularis,"*Journal of Steroid Biochemistry and Molecular Biology*, 114:167-173 (2009).
Salvati, M. E., et al., "Identification and Optimization of a Novel Series of [2.2.1]-oxabicyclo imide-based Androgen Receptor Antagonists," *Bioorganic & Medicinal Chemistry Letters*, 18: 1910-1915 (2008).
Schafer, S. and Kolkhof, P., "Failure is an Option: Learning From Unsuccessful Proof-of-Concept Trials," *Drug Discovery Today*, 13(21/22):913-916 (2008).
Sun, C., et al. "Discovery of Potent, Orally-Active, and Muscle-Selective Androgen Receptor Modulators Based on an N-Aryl-hydroxybicyclohydantoin Scaffold," *J. Med. Chem.* 49(26): 7596-7599 (2006).
Sundar, et al., "Spironolactone, a possible selective androgen receptor modulator, should be used with caution in patients with metastatic carcinoma of the prostate,"*BMJ Case Rep*. (Feb. 25, 2012), Abstract.
Thiel, K. A., "Structure-aided drug design's next generation,"*Nature Biotechnol*, 22(5): 513-519 (May 2004).
Tucker, H., el al., "Nonsterodial Antiandrogens, Synthesis and Structure-Activity Relationships of 3-Substituted Derivatives of 2-Hydroxypropionanilides," *J. Med. Chem.*, 31: 954-959 (1988).
Vajda, E. G., et al., Pharmacokinetics and Pharmacodynamics of LGD-3303 [9-Cholor-2-ehyl-1-methyl-3-(2,2,2-trifluoroethyl)-3H-pyrrolo-[3,2-f]quinolin-7(6H)-one], an Orally Available Nonsteroidal-Selective Androgen Receptor Modulator, *The Journal of Pharmacology and Experimental Therapeutics*, 328(2): 663-670 (2009).
Van Oeveren, A., et al., "Novel Selective Androgen Receptor Modulators: SAR Studies of 6-bisalkylamino-2-quinolinones,"*Bioorganic & Medicinal Chemistry Letters*,17: 1527-1531 (2007).
Wang, Z. et al., "Anti-Inflammatory Properties and Regulatory Mechanism of a Novel Derivative of Artemisinin in Experimental Autoimmune Encephalomyelitis," *The Journal of Immunology*, J Immunol 179;5958-5965 (2007).
Zeng, C., et al., "Efficient Synthesis of (2R,3S)-2-amino-3-(benzyloxy)-4,4,4-trifluorobutanoic acid (4,4,4-trifluror-OBn-D-allothreonine)," *Tetrahedron Letters*,51: 5361-5363 (2010).
Zhang, X., et al., "Design, Synthesis, and in Vivo SAR of a Novel Series of Pyrazolines as Potent Selective Androgen Receptor Modulators," *J. Med. Chem*, 50(16): 3857-3869 (2007).
Zhang, X., et al., "Synthesis and SAR of Novel Hydantoin Derivatives as Selective Androgen Receptor Modulators," *Bioorganic & Medicinal Chemistry Letters*, 16: 5763-5766 (2006).
International Search Report and Written Opinion for Int'l Application No. PCT/US2009/001035 entitled: Selective Androgen Receptor Modulators; Dated: Aug. 7, 2009.
International Preliminary Report on Patentability for Int'l Application No. PCT/US2009/001035 entitled: Selective Androgen Receptor Modulators; Dated: Aug. 24, 2010.
International Search Report and Written Opinion for Int'l Application No. PCT/US2010/304480 entitled: Selective Androgen Receptor Modulators; Dated: Jun. 9, 2010.
International Preliminary Report on Patentability for Int'l Application No. PCT/US2010/030480 entitled: Selective Androgen Receptor Modulators; Dated: Oct. 11, 2011.
International Search Report and Written Opinion for Int'l Application No. PCT/US2011/023768 entitled: Selective Androgen Receptor Modulators; Dated: Mar. 25, 2011.
International Preliminary Report on Patentability for Int'l Application No. PCT/US2011/023768 entitled: Selective Androgen Receptor Modulators; Dated: Aug. 7, 2012.
European Search report for European Application No. 11740437.6 entitled: Selective Androgen Receptor Modulators; Dated: Apr. 26, 2013.
International Search Report and Written Opinion for International Application No. PCT/US2011/053375 entitled: Selective Androgen Receptor Modulators; Dated: Jan. 16, 2012.
International Preliminary Report on Patentability for International Application No. PCT/2011/053375 entitled: Selective Androgen Receptor Modulators; Dated: Apr. 2, 2013.
Notice of Allowance and Fees Due for U.S. Appl. No. 12/378,812, entitled: Selective Androgen Receptor Modulators; Date Mailed: Jul. 21, 2011.
Non-Final Office Action for U.S. Appl. No. 12/541,489, entitled: Selective Androgen Receptor Modulators; Mailing Date: Aug. 4, 2011.
Non-Final Office Action for U.S. Appl. No. 12/541,489, entitled: Selective Androgen Receptor Modulators; Mailing Date: Oct. 25, 2011.
Notice of Allowance for U.S. Appl. No. 12/541,489, entitled: Selective Androgen Receptor Modulators; Date Mailed: May 10, 2012.
Office Action for U.S. Appl. No. 12/806,636, entitled: Selective Androgen Receptor Modulators; Date Mailed: Sep. 12, 2012.
Notice of Allowance for U.S. Appl. No. 12/806,636, entitled: Selective Androgen Receptor Modulators; Date Mailed: Feb. 1, 2013.
Non-Final Office Action for U.S. Appl. No. 13/570,417, entitled: Selective Androgen Receptor Modulators; Date Mailed: Apr. 24, 2013.

(56) References Cited

OTHER PUBLICATIONS

Notice of Allowance for U.S. Appl. No. 13/570,417, entitled: Selective Androgen Receptor Modulators; Date Mailed: Sep. 17, 2013.
Non-Final Office Action for U.S. Appl. No. 13/576,754, entitled: Selective Androgen Receptor Modulators; Date Mailed: Jan. 17, 2014.
Non-Final Office Action for U.S. Appl. No. 13/175,306, entitled: Selective Androgen Receptor Modulators; Date Mailed: Oct. 31, 2012.
Final Office Action for U.S. Appl. No. 13/175,306, entitled: Selective Androgen Receptor Modulators; Date Mailed: Apr. 5, 2013.
Notice of Allowance and Fees Due for U.S. Appl. No. 13/175,306, entitled: Selective Androgen Receptor Modulators; Date Mailed: Sep. 18, 2013.

* cited by examiner

SELECTIVE ANDROGEN RECEPTOR MODULATORS

RELATED APPLICATIONS

This application is the U.S. National Stage of International Application No. PCT/US2011/053375, filed Sep. 27, 2011, which designates the U.S., published in English, and claims the benefit of U.S. Provisional Application No. 61/387,440, filed Sep. 28, 2010. The entire teachings of the above applications are incorporated herein by reference.

BACKGROUND OF THE INVENTION

Androgen signaling is mediated through the androgen receptor (AR) and is a nuclear signaling pathway of tremendous importance in mammals. In addition to its primary role in sexual development, maturation and maintenance of sexual function in both males and females, this critical hormone signaling pathway affects a large number of non-sexual tissues including, bone, muscle, CNS, liver, etc. In humans, testosterone and dihydrotestosterone are the primary ligands that mediate AR-signaling. Both are high affinity ligands for AR, with dihydrotestosterone having somewhat higher affinity. Testosterone is converted to dihydrotestosterone through the action of 5α-reductase enzymes and is converted to 17β-estradiol (potent endogenous estrogen) through the action of P-450 aromatase enzymes. AR signaling is mediated by binding of an AR ligand to AR in the cellular cytosol, homodimerization of two AR receptors and nuclear location of the ligand bound dimer to the cell nucleus where the complex associates with various coactivators as well as Androgen Response Elements (palindrome-like sequences of DNA) which serve as activation sites for certain AR-mediated genes. Due to the very large number of AR target tissues, both sexual and non-sexual, androgens such as testosterone and dihydrotestosterone have a number of potentially desirable actions as well as non-desirable actions depending on the particular individual's age, sex, therapeutic need, etc. In the adult male and female, certain positive consequences of AR-agonist signaling can be generalized as including increased bone mineral density and a corresponding reduction of risk of bone fractures. Accordingly, androgen supplementation can be very valuable in the prevention or treatment of osteoporosis where the osteoporosis might originate from any number of different causes, such as corticosteroid induced osteoporosis and age-related osteoporosis (e.g. post-menopausal). Likewise, males and females respond to agonist supplementation with an increase in muscle mass and very often a decrease in fat mass. This is beneficial in a very large number of treatment modalities. For example, there are many wasting syndromes associated with different disease states where the therapeutic goal is for a patient to maintain weight and function, such as the treatment of cancer associated cachexia, AIDs-related cachexia, anorexia and many more. Other muscle-wasting disorders such as muscular dystrophy in its many forms as well as related disorders might be treated to advantage with androgens. The increase in muscle mass with concomitant reduction in fat mass associated with anabolic androgen action has additional health benefits for many men and women including potentially increased sensitivity to insulin. Androgen supplementation is also associated with reduction of high triglycerides, though there is a general correlation with androgen use and decreased HDL levels and in some cases, increased LDL levels. In the CNS, numerous laudatory benefits have been associated with androgen supplementation including improved sexual desire and functioning, increased cognition, memory, sense of well being and possible decrease in risk of Alzheimer's disease.

Androgen antagonists have been used in treating prostate cancer, where blockade of androgen signaling is desired whereas some androgens agonists (e.g. dihydrotestosterone) stimulate the hypertrophy of prostate tissue and may be a causative factor in prostate cancer. Androgen agonist activity is often associated with stimulation of benign prostate hyperplasia, a disease characterized by an enlarged prostate often accompanied by discomfort and difficulty in urination due to blockage of the urethra. As a result, androgen antagonists have efficacy in the reduction of the size of the prostate and the corresponding symptoms of benign prostate hyperplasia, though it is much more common to use a 5α-reductase inhibitor (e.g. finasteride) as such inhibitors do not decrease androgen signaling systemically to the same extent as a typical anti-androgen (e.g. bicalutamide), but rather reduce androgen drive more site specifically to where testosterone to DHT conversion occurs such as the prostate and scalp. Androgen antagonists also find utility in the treatment of hirsutism in women as well as the treatment of acne. Androgens are generally contraindicated in conditions that are treated with androgen antagonists since they can exacerbate the symptoms that are being treated.

Ideally, an androgen would retain the benefits of androgen agonists while minimizing the stimulatory effects on the prostate in males as well as some of the other untoward effects of androgens including masculinization of women and increase in acne in both sexes. Androgens that demonstrate tissue selective effects compared to the benchmarks testosterone and/or dihydrotestosterone are typically referred to as androgen receptor modulators or more often, selective androgen receptor modulators (SARMs). At the far end of potential selectivity, an ideal SARM would demonstrate no prostate stimulation while maintaining or growing muscle sufficient to effectively mimic the effects of testosterone or dihydrotestosterone. The growing appreciation of the positive contribution that SARMs can make in the many therapeutic areas where androgen activity is desirable has led to a large amount of research into this important area. Due to a compelling need for novel and effective androgen therapies with potentially reduced side effects, novel and effective SARM compounds are urgently needed.

SUMMARY OF THE INVENTION

In certain embodiments, this invention describes a compound of formula I

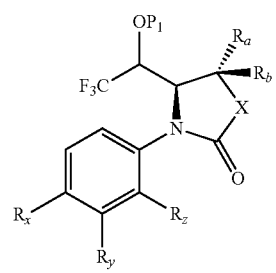

wherein $R_x$ is CN, Cl, Br, $NO_2$ or $R_{x1}$;

$R_y$ is $CH_3$, $CF_3$, or halogen;

$R_z$ is hydrogen or optionally $C_{1-3}$ alkyl, $C_{2-3}$ alkenyl, $C_{1-3}$ hydroxyalkyl, $C_{1-3}$ haloalkyl, $NO_2$, $NH_2$, OMe, halogen or OH; or $R_y$ and $R_z$ together form

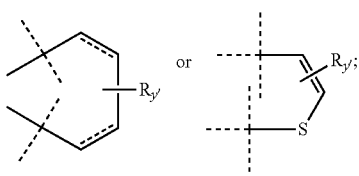

wherein $R_{y'}$ is optionally a substituent selected from the group consisting of halogen, $C_{1-3}$ alkyl, $C_{1-3}$ haloalkyl and OH;

$R_{x1}$ is a 5 member heteroaryl, said heteroaryl selected from

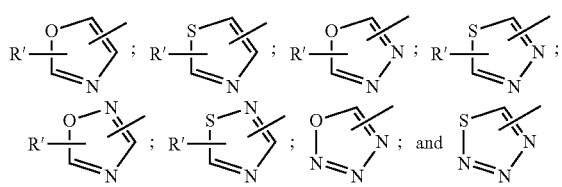

R' is hydrogen or optionally $C_1$-$C_2$ alkyl, $CF_3$, or halogen; or $R_x$ and $R_y$ together with the phenyl group to which they are attached form a 5 member aromatic ring selected from:

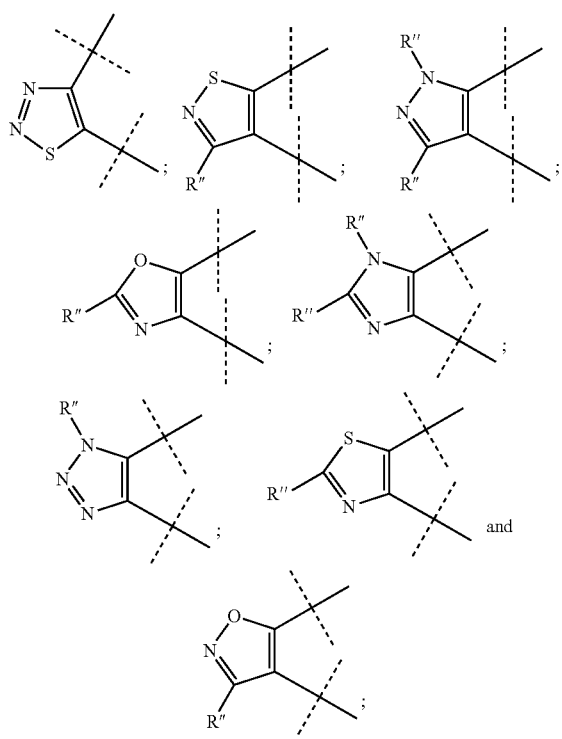

wherein each R'' is independently hydrogen or optionally $CF_3$, or $C_1$-$C_2$ alkyl;

$P_1$ is hydrogen or a metabolically labile group;

$R_a$ and $R_b$ are each independently selected from hydrogen or $C_1$-$C_3$ alkyl; and X is $CH_2$, O or $NR_c$; wherein $R_c$ is hydrogen or $C_1$-$C_3$ alkyl;

or pharmaceutically acceptable salts thereof.

DETAILED DESCRIPTION OF THE INVENTION

In certain embodiments, this invention describes a compound of formula I

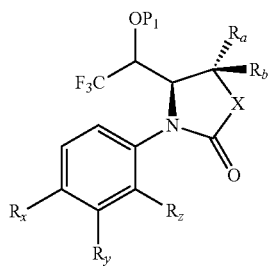

I wherein $R_x$ is CN, Cl, Br, $NO_2$ or $R_{x1}$;

$R_y$ is $CH_3$, $CF_3$, or halogen;

$R_z$ is hydrogen or optionally $C_{1-3}$ alkyl, $C_{2-3}$ alkenyl, $C_{1-3}$ hydroxyalkyl, $C_{1-3}$ haloalkyl, $NO_2$, $NH_2$, OMe, halogen or OH; or $R_y$ and $R_z$ together form

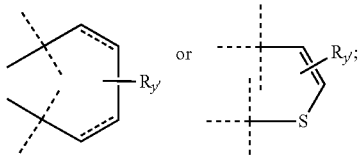

wherein $R_{y'}$ is optionally a substituent selected from the group consisting of halogen, $C_{1-3}$ alkyl, $C_{1-3}$ haloalkyl and OH;

$R_{x1}$ is a 5 member heteroaryl, said heteroaryl selected from

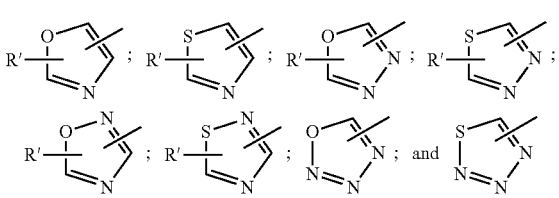

R' is hydrogen or optionally $C_1$-$C_2$ alkyl, $CF_3$, or halogen; or $R_x$ and $R_y$ together with the phenyl group to which they are attached form a 5 member aromatic ring selected from:

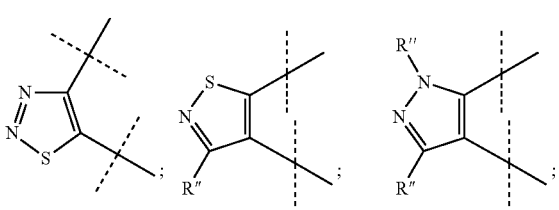

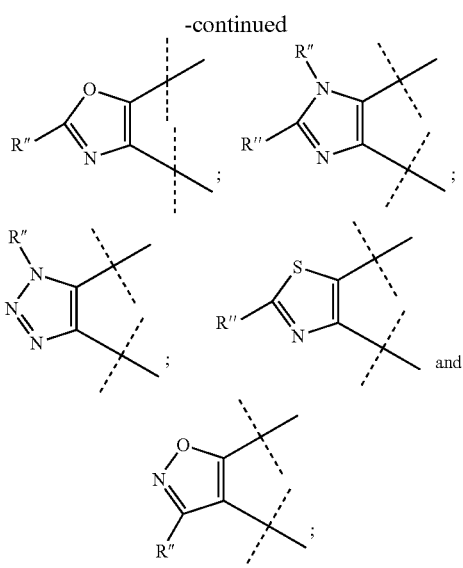

wherein each R″ is independently hydrogen or optionally CF$_3$, or C$_1$-C$_2$ alkyl;
P$_1$ is hydrogen or a metabolically labile group;
R$_a$ and R$_b$ are each independently selected from hydrogen or C$_1$-C$_3$ alkyl; and
X is CH$_2$, O or NR$_c$; wherein
R$_c$ is hydrogen or C$_1$-C$_3$ alkyl;
or pharmaceutically acceptable salts thereof.

In some embodiments of this invention, the compound of formula I is a compound of structure Ia:

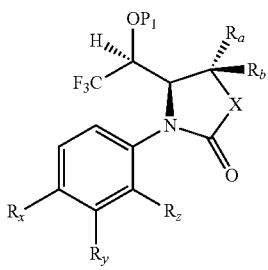

In certain embodiments of this invention, the compound of formula I is a compound of formula Ib:

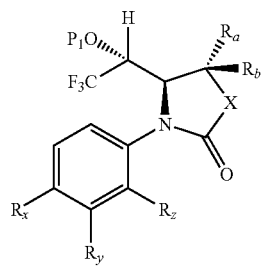

In certain embodiments, the animal to be administered the compound of formula I, Ia or Ib is a mammal. In some embodiments, that mammal is a human.

In certain embodiments of this invention, for the compound of formula I, Ia or Ib, R$_x$ is CN.

In certain embodiments of this invention, for the compound of formula I, Ia or Ib, R$_y$ is CF$_3$ or Cl.

In certain embodiments of this invention, for the compound of formula I, Ia or Ib, R$_z$ is C$_{1-3}$ alkyl, hydrogen, halogen, C$_{1-3}$ hydroxyalkyl or C$_2$ alkenyl.

In some embodiments of this invention, for the compound of formula I, Ia or Ib, R$_z$ is hydrogen.

In certain embodiments of this invention, for the compound of formula I, Ia or Ib, R$_x$ is CN, R$_y$ is CF$_3$ or Cl and R$_z$ is CH$_3$ or hydrogen.

In some embodiments, for the compound of formula I, Ia or Ib, X is CH$_2$.

In certain embodiments, for the compound of formula I, Ia or Ib, X is NCH$_3$.

In some embodiments, for the compound of formula I, Ia or Ib, X is O.

In certain embodiments, for the compound of formula I, Ia or Ib, R$_a$ is hydrogen and R$_b$ is hydrogen.

In some embodiments, for the compound of formula I, Ia or Ib, R$_a$ is CH$_3$ and R$_b$ is hydrogen.

In certain embodiments, for the compound of formula I, Ia or Ib, R$_a$ is hydrogen and R$_b$ is methyl.

In some embodiments, for the compound of formula I, Ia or Ib, R$_a$ and R$_b$ are each methyl.

In some embodiments, for the compound of formula I, Ia or Ib, P$_1$ is hydrogen or a metabolically labile group that after oral administration in a mammal leaves P$_1$ as hydrogen. In some embodiments, the mammal is a human.

In certain embodiments, for the compound of formula I, Ia or Ib, P$_1$ is an alkyl acyl group containing up to 20 carbons, aryl acyl group containing up to 18 carbons, alkyl ether containing up to 12 carbons, sulfate, or phosphate.

In certain embodiments, for the compound of formula I, Ia or Ib, P$_1$ is hydrogen, SO$_3^-$, PO$_3^{2-}$, C$_{1-3}$ alkyl, C(=O)—C$_{1-10}$ alkyl and C(=O)(O)-aryl.

In some embodiments, for the compound of formula I, Ia or Ib, P$_1$ is hydrogen or C(=O)—C$_{1-6}$ alkyl.

In some embodiments, P$_1$ is hydrogen.

In some embodiments of this invention, a compound of formula II, IIa and IIb are described:

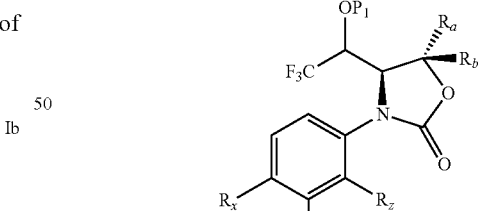

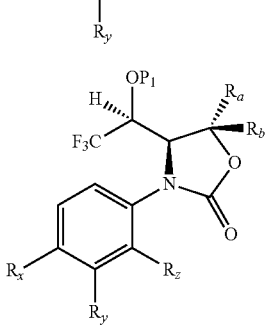

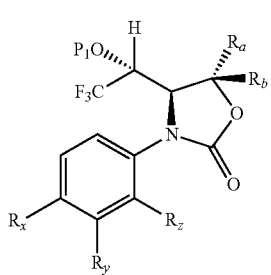

wherein $R_x$ is CN, $R_y$ is $CF_3$ or Cl and $R_z$ is hydrogen or $CH_3$;
$R_a$ is $CH_3$ and $R_b$ is hydrogen; and
$P_1$ is hydrogen.

In some embodiments, for the compound of formula II, IIa and IIb:
$R_x$ is CN, $R_y$ is $CF_3$ or Cl and $R_z$ is hydrogen or $CH_3$;
$R_a$ is hydrogen and $R_b$ is hydrogen; and
$P_1$ is hydrogen.

In some embodiments, this invention describes a compound of formula III, IIIa and IIIb

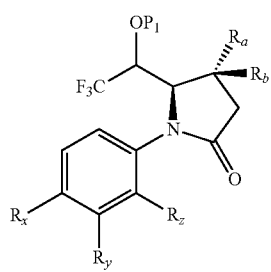

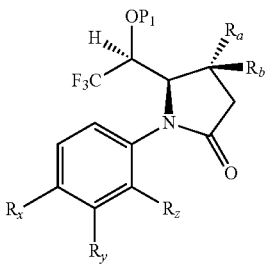

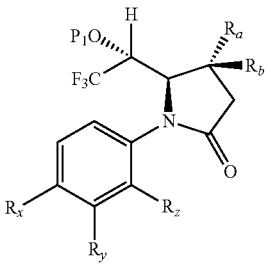

wherein $R_x$ is CN, $R_y$ is $CF_3$ or Cl and $R_z$ is hydrogen or $CH_3$;
$R_a$ is $CH_3$ and $R_b$ is hydrogen; and
$P_1$ is hydrogen.

In some embodiments, for the compound of formula III, IIIa and IIIb:

$R_x$ is CN, $R_y$ is $CF_3$ or Cl and $R_z$ is hydrogen or $CH_3$;
$R_a$ is hydrogen and $R_b$ is hydrogen; and
$P_1$ is hydrogen.

In some embodiments, for the compound of formula IV, IVa and IVb:

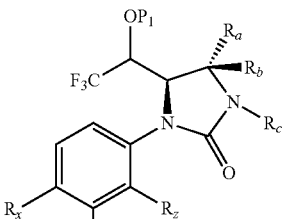

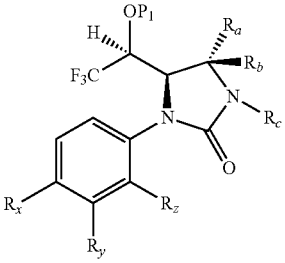

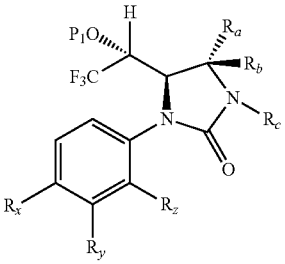

wherein $R_x$ is CN, $R_y$ is $CF_3$ or Cl and $R_z$ is hydrogen or $CH_3$;
$R_a$ is $CH_3$, $R_b$ is hydrogen and $R_c$ is $CH_3$; and
$P_1$ is hydrogen.

In some embodiments, for the compound of formula IV, IVa and IVb:
$R_x$ is CN, $R_y$ is $CF_3$ or Cl and $R_z$ is hydrogen or $CH_3$;
$R_a$ is hydrogen, $R_b$ is hydrogen and $R_c$ is $CH_3$; and
$P_1$ is hydrogen.

In certain embodiments, this invention includes a compound of formula I through IV wherein the compound of formula I through IV is predominately one diastereomer. In this context, the term "predominately" means the compound of formula I through IV is more than 50% of a single diastereomer.

In some embodiments, the compound of formula I through IV is more than 60% of a single diastereomer.

In some embodiments, the compound of formula I through IV is more than 70% of a single diastereomer.

In some embodiments, the compound of formula I through IV is more than 80% of a single diastereomer.

In some embodiments, the compound of formula I through IV is more than 90% of a single diastereomer.

In some embodiments, the compound of formula I through IV is more than 95% of a single diastereomer.

In some embodiments, the compound of formula I through IV is more than 98% of a single diastereomer.

In some embodiments, the compound of formula I through IV is more than 99% of a single diastereomer.

In some embodiments, the compound of formula I through IV is more than 99.9% of a single diastereomer.

In certain embodiments, this invention includes a compound of formula I through IV wherein the compound of formula I through IV is predominately one enantiomer. In this context, the term "predominately" means the compound of formula I through IV has an ee of greater than 50%.

In some embodiments, the compound of formula I through IV has an ee of greater than 60%.

In some embodiments, the compound of formula I through IV has an ee of greater than 70%.

In some embodiments, the compound of formula I through IV has an ee of greater than 80%.

In some embodiments, the compound of formula I through IV has an ee of greater than 90%.

In some embodiments, the compound of formula I through IV has an ee of greater than 95%.

In some embodiments, the compound of formula I through IV has an ee of greater than 98%.

In some embodiments, the compound of formula I through IV has an ee of greater than 99%.

In some embodiments, the compound of formula I through IV has an ee of greater than 99.9%.

In some embodiments of this invention, the compound of formula I through IV, is selected from the following list. (The compound names in the list were generated with the assistance of ChemDraw® versions 8.0, 9.0 and/or 11.0 (CambridgeSoft Corporation, 100 CambridgePark Drive, Cambridge, Mass. 02140 USA)). When the stereochemistry at a chiral center is not defined in the compound name this indicates that the sample prepared contained a mixture of isomers at this center.

4-((R)-2-oxo-5-((R)-2,2,2-trifluoro-1-hydroxyethyl)pyrrolidin-1-yl)-2-(trifluoromethyl)benzonitrile;
4-((R)-2-oxo-5-((S)-2,2,2-trifluoro-1-hydroxyethyl)pyrrolidin-1-yl)-2-(trifluoromethyl)benzonitrile;
3-methyl-4-((S)-2-oxo-5-((R)-2,2,2-trifluoro-1-hydroxyethyl)pyrrolidin-1-yl)-2-(trifluoromethyl)benzonitrile;
3-methyl-4-((S)-2-oxo-5-((S)-2,2,2-trifluoro-1-hydroxyethyl)pyrrolidin-1-yl)-2-(trifluoromethyl)benzonitrile;
(S)-1-(Benzo[d][1,2,3]thiadiazol-6-yl)-5-((R)-2,2,2-trifluoro-1-hydroxyethyl)pyrrolidin-2-one;
(S)-1-(Benzo[d][1,2,3]thiadiazol-6-yl)-5-((S)-2,2,2-trifluoro-1-hydroxyethyl)pyrrolidin-2-one;
4-((R)-2-oxo-4-((R)-2,2,2-trifluoro-1-hydroxyethyl)oxazolidin-3-yl)-2-(trifluoromethyl)benzonitrile;
4-((R)-2-oxo-4-((S)-2,2,2-trifluoro-1-hydroxyethyl)oxazolidin-3-yl)-2-(trifluoromethyl)benzonitrile;
2-chloro-4-((S)-2-oxo-4-((R)-2,2,2-trifluoro-1-hydroxyethyl)oxazolidin-3-yl)benzonitrile;
2-chloro-4-((S)-2-oxo-4-((S)-2,2,2-trifluoro-1-hydroxyethyl)oxazolidin-3-yl)benzonitrile;
2-chloro-3-methyl-4-((R)-2-oxo-4-((R)-2,2,2-trifluoro-1-hydroxy ethyl)oxazolidin-3-yl)benzonitrile;
2-chloro-3-methyl-4-((R)-2-oxo-4-((S)-2,2,2-trifluoro-1-hydroxy ethyl)oxazolidin-3-yl)benzonitrile;
3-methyl-4-((R)-2-oxo-4-((R)-2,2,2-trifluoro-1-hydroxyethyl)oxazolidin-3-yl)-2-(trifluoro methyl)benzonitrile;
3-Methyl-4-((R)-2-oxo-4-((S)-2,2,2-trifluoro-1-hydroxyethyl)oxazolidin-3-yl)-2-(trifluoro methyl)benzonitrile;
2-chloro-3-methyl-4-((4S,5R)-5-methyl-2-oxo-4-((S)-2,2,2-trifluoro-1-hydroxy ethyl)oxazolidin-3-yl)benzonitrile;
2-chloro-3-methyl-4-((4S,5R)-5-methyl-2-oxo-4-((R)-2,2,2-trifluoro-1-hydroxyethyl)oxazolidin-3-yl)benzonitrile;
2-chloro-3-methyl-4-((4S,5S)-5-methyl-2-oxo-4-((R)-2,2,2-trifluoro-1-hydroxyethyl)oxazolidin-3-yl)benzonitrile;
2-chloro-3-methyl-4-((4S,5S)-5-methyl-2-oxo-4-((S)-2,2,2-trifluoro-1-hydroxyethyl)oxazolidin-3-yl)benzonitrile;
4-((4S,5S)-5-methyl-2-oxo-4-((R)-2,2,2-trifluoro-1-hydroxyethyl)oxazolidin-3-yl)-2-(trifluoromethyl)benzonitrile;
4-((4S,5S)-5-methyl-2-oxo-4-((S)-2,2,2-trifluoro-1-hydroxyethyl)oxazolidin-3-yl)-2-(trifluoromethyl)benzonitrile;
2-Chloro-4-((4S,5S)-5-methyl-2-oxo-4-((R)-2,2,2-trifluoro-1-hydroxyethyl)oxazolidin-3-yl)benzonitrile;
2-chloro-4-((4S,5S)-5-methyl-2-oxo-4-((S)-2,2,2-trifluoro-1-hydroxyethyl)oxazolidin-3-yl)benzonitrile;
3-methyl-4-((4S,5S)-5-methyl-2-oxo-4-((R)-2,2,2-trifluoro-1-hydroxyethyl)oxazolidin-3-yl)-2-(trifluoromethyl)benzonitrile;
3-methyl-4-((4S,5S)-5-methyl-2-oxo-4-((S)-2,2,2-trifluoro-1-hydroxyethyl)oxazolidin-3-yl)-2-(trifluoromethyl)benzonitrile;
4-((R)-3-methyl-2-oxo-5-((R)-2,2,2-trifluoro-1-hydroxyethyl)imidazolidin-1-yl)-2-(trifluoromethyl)benzonitrile; and
4-((R)-3-methyl-2-oxo-5-((S)-2,2,2-trifluoro-1-hydroxyethyl)imidazolidin-1-yl)-2-(trifluoromethyl)benzonitrile.

In some embodiments of this invention, the compound of formula I through IV, is selected from the following list. (The compound names in the list were generated with the assistance of ChemDraw®versions 8.0, 9.0 and/or 11.0 (CambridgeSoft Corporation, 100 CambridgePark Drive, Cambridge, Mass. 02140 USA)). When the stereochemistry at a chiral center is not defined in the compound name this indicates that the sample prepared contained a mixture of isomers at this center.

4-((R)-2-oxo-5-((S)-2,2,2-trifluoro-1-hydroxyethyl)pyrrolidin-1-yl)-2-(trifluoromethyl)benzonitrile;
3-methyl-4-((R)-2-oxo-5-((S)-2,2,2-trifluoro-1-hydroxyethyl)pyrrolidin-1-yl)-2-(trifluoromethyl)benzonitrile;
4-((R)-2-oxo-4-((S)-2,2,2-trifluoro-1-hydroxyethyl)oxazolidin-3-yl)-2-(trifluoromethyl)benzonitrile;
2-chloro-4-((S)-2-oxo-4-((R)-2,2,2-trifluoro-1-hydroxyethyl)oxazolidin-3-yl)benzonitrile;
2-chloro-3-methyl-4-((R)-2-oxo-4-((S)-2,2,2-trifluoro-1-hydroxy ethyl)oxazolidin-3-yl)benzonitrile;
3-methyl-4-((R)-2-oxo-4-((S)-2,2,2-trifluoro-1-hydroxyethyl)oxazolidin-3-yl)-2-(trifluoro methyl)benzonitrile;
2-chloro-3-methyl-4-((4S,5S)-5-methyl-2-oxo-4-((S)-2,2,2-trifluoro-1-hydroxyethyl)oxazolidin-3-yl)benzonitrile;
4-((4S,5S)-5-methyl-2-oxo-4-((S)-2,2,2-trifluoro-1-hydroxyethyl)oxazolidin-3-yl)-2-(trifluoromethyl)benzonitrile;
4-((4S,5S)-5-methyl-2-oxo-4-((R)-2,2,2-trifluoro-1-hydroxyethyl)oxazolidin-3-yl)-2-(trifluoromethyl)benzonitrile;
2-Chloro-4-((4S,5S)-5-methyl-2-oxo-4-((R)-2,2,2-trifluoro-1-hydroxyethyl)oxazolidin-3-yl)benzonitrile; and
2-Chloro-4-((4S,5S)-5-methyl-2-oxo-4-((S)-2,2,2-trifluoro-1-hydroxyethyl)oxazolidin-3-yl)benzonitrile.

The invention also relates to pharmaceutical compositions comprising a compound of formula I-IV or any of the structural embodiments described herein and at least one pharmaceutically acceptable excipient.

The invention also provides a method of modulating an androgen receptor in a cell, comprising the administration of a compound to said cell wherein said compound has structural formula I-IV or any of the structural embodiments described herein, or a pharmaceutically acceptable salt thereof.

This invention provides a method of identifying a compound capable of modulating an androgen receptor comprising contacting a cell expressing an androgen receptor with a compound according to formula I-IV, and monitoring the effect of the compound on the cell.

This invention also provides a method of treating (e.g., preventing, or ameliorating the symptoms associated with, or reducing the incidence of, reducing the pathogenesis of, facilitating the recovery from or delaying the onset of) a disease, syndrome, illness, or symptom associated with insufficient androgen levels in a mammal in need thereof, wherein said method comprises the administration to said mammal of an effective amount of a compound of formula I-IV, or any one of the structural embodiments described herein or a pharmaceutically acceptable salt thereof, or a pharmaceutical composition comprising a compound of formula I-IV, or one of the structural embodiments described herein, or a pharmaceutically acceptable salt thereof and a pharmaceutically acceptable excipient. In a particular embodiment, the mammal is a human.

In some embodiments, this invention provides a method of treating (e.g., preventing, or ameliorating the symptoms associated with, or reducing the incidence of, reducing the pathogenesis of, facilitating the recovery from or delaying the onset of) sarcopenia, frailty, multiple sclerosis, osteoporosis, anemia, cognitive impairment, cachexia, muscular dystrophy, weak appetite, low body weight, anorexia nervosa, acne, seborrhea, polycystic ovarian syndrome, hair loss, AIDs wasting, chronic fatigue syndrome, short stature, low testosterone levels, diminished libido, benign prostate hypertrophy, infertility, erectile dysfunction, vaginal dryness, premenstrual syndrome, postmenopausal symptoms, female hormone replacement therapy, male hormone replacement therapy, depression, Type II diabetes, mood disorders, sleep disorders, memory disorders, neurodegenerative disorders, Alzheimer's dementia, attention deficit disorder, senile dementia, coronary artery disease, hirsutism, pain, myalgia, myocardial infarction, stroke, clotting disorders, thromboembolisms, congestive heart disorder, low insulin sensitivity, low glucose utilization, high blood sugar, organ transplant, metabolic syndrome, diabetes, glucose intolerance, hyperinsulinemia, insulin resistance, tooth injury, tooth disease, periodontal disease, liver disease, thrombocytopenia, fatty liver conditions, endometriosis, hot flushes, hot flashes, vasomotor disturbance, stress disorders, dwarfism, dyslipidemia, cardiovascular disease, coronary artery disease, renal disease, thin skin disorders, lethargy, osteopenia, dialysis, irritable bowel syndrome, Crohn's disease, Paget's disease, osteoarthritis, connective tissue disease or disorders, injury, burns, trauma, wounds, bone fracture, atherosclerosis, cachexia, cancer cachexia, and obesity, in a mammal in need thereof comprising the administration to said mammal of an effective amount of a compound according to a structure of formula I-IV or one of the structural embodiments described herein, or a pharmaceutically acceptable salt thereof, or a pharmaceutical composition comprising a compound of structural formula I-IV, or one of the structural embodiments described herein including pharmaceutically acceptable salts thereof and a pharmaceutically acceptable excipient. In a particular embodiment, the mammal is a human.

In certain aspects, this invention describes a method of treating (e.g., preventing, or ameliorating the symptoms associated with, or reducing the incidence of, reducing the pathogenesis of, facilitating the recovery from or delaying the onset of) prostate cancer, breast cancer, endometrial cancer, hepatocellular cancer, lymphoma, multiple endocrine neoplasia, vaginal cancer, renal cancer, thyroid cancer, testicular cancer, leukemia, and ovarian cancer in a mammal in need thereof comprising the administration to said mammal of a compound according to a structure of formula I-IV, or one of the structural embodiments described herein, or a pharmaceutically acceptable salt thereof, or a pharmaceutical composition comprising a compound of structural formula I-IV, or one of the structural embodiments described herein including pharmaceutically acceptable salts thereof and a pharmaceutically acceptable excipient. In a particular embodiment, the mammal is a human.

In the context of this disclosure, the phrase "formula I through IV" is meant to, in each instant, include compounds of formula I, Ia, Ib, II, IIa, IIb, III, IIIa, IIIb, IV, IVa and IVb In some embodiments, a process for the preparation of a compound of formula I, Ia and Ib wherein X is O, is described, wherein said process comprises a process for the preparation of a compound of formula B, comprising:

a) reacting a compound of formula A with a carbonylating reagent

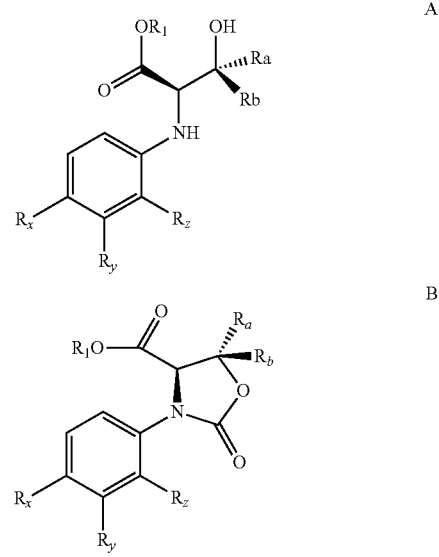

wherein:

$R_x$, $R_y$, $R_z$, $R_a$ and $R_b$ are each independently as defined for formula I or any of its related embodiments and;

$R_1$ is a hydrogen or a suitable carboxylic acid protecting group.

In certain embodiments of this invention, the process of preparing the compound of formula B is conducted in the presence of a base.

In some embodiments of the processes described herein, $R_1$ is $C_{1-6}$ alkyl, benzyl or an organosilane.

In certain embodiments of the processes described herein, said carbonylating agent is phosgene, triphosgene, N,N'-carbonyldiimadazole or a dialkylcarbonate.

In certain embodiments, a process for the production of a compound of formula II, IIa and IIb comprising the reaction of a compound of formula C with a reagent capable of generating a trifluoromethyl anion addition equivalent followed by a proton-donating work-up:

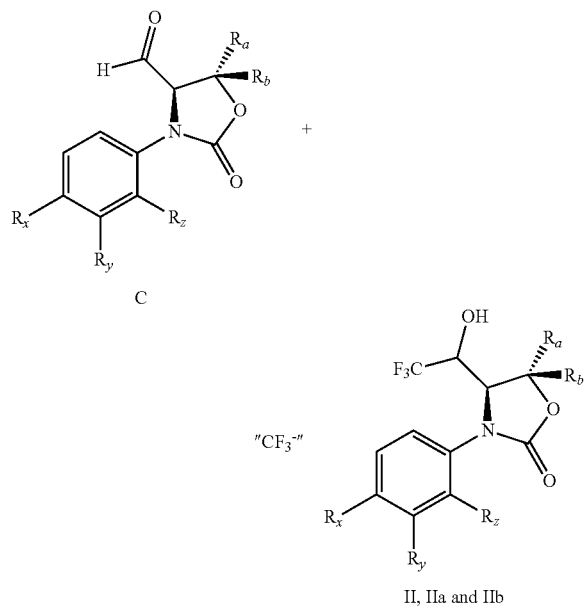

C

II, IIa and IIb

In some embodiments, the trifluoromethyl anion generating equivalent comprises a trifluoromethylsilane. In certain embodiments, the trifluoromethyl-containing silane is trimethylsilyltrifluoromethane.

In some embodiments, said trifluoromethyl anion is generated from a trifluoromethylsilane in the presence of a fluoride anion.

DETAILED DESCRIPTION OF THE INVENTION

The term "alkenyl" as used herein refers to a hydrocarbon backbone radical, having the number of carbon atoms falling within the specified range. For example, $C_{2-3}$ alkenyl means that a hydrocarbon radical is attached that may contain anywhere from 2 to 3 carbon atoms with the remaining valence filled in by hydrogen atoms unless specified otherwise. The term also includes each permutation as though it were separately listed. Thus, $C_{2-3}$ alkenyl includes ethenyl, 1-propenyl and 2-propenyl.

The term "alkyl" as used herein refers to both straight and branch chain hydrocarbon radicals, having the number of carbon atoms falling within the specified range. For example, $C_{1-4}$ alkyl means that a hydrocarbon radical is attached that may contain anywhere from 1 to 4 carbon atoms with the remaining valence filled in by hydrogen atoms. The definition also includes separately each permutation as though it were separately listed. Thus, $C_{1-2}$ alkyl includes methyl and ethyl. The term $C_{1-3}$ alkyl includes methyl, ethyl, propyl and 2-propyl. The term $C_{1-4}$ alkyl includes methyl, ethyl, n-propyl, 2-propyl, n-butyl, 2-butyl, iso-butyl and tert-butyl. The term $C_{1-5}$ alkyl includes methyl, ethyl, 2-propyl, n-butyl, 2-methylbutyl, tert-butyl, n-pentyl, pentan-2-yl, pentan-3-yl, and tert-pentyl, iso-pentyl.

The term "halogen" as used herein refers to a fluorine, chlorine, bromine or iodine radical.

The term "haloalkyl" refers to an alkyl radical wherein said alkyl radical is the same as defined for the term "alkyl" except that the alkyl radical additionally has from 1 to 5 halogen atoms attached to the alkyl chain. For example, $C_1$ haloalkyl includes —$CH_2F$, —$CHF_2$, —$CF_3$ and the like, $C_2$ haloalkyl includes —$CH_2F$, $CHF_2$, $CF_3$, —$CH_2CH_2F$, —$CH_2CHF_2$, —$CH_2CF_3$, —$CF_2CHF_2$, —$CF_2CF_3$ and the like. $C_{1-3}$ haloalkyl is defined to include —$CH_2F$, —$CHF_2$, —$CF_3$, —$CH_2CF_3$, —$CHFCF_3$, —$CF_2CF_3$, —$CHClCH_3$, —$CH_2CH_2Cl$, —$CH_2CH_2CF_3$, and the like. $C_{1-4}$ haloalkyl is defined to include —$CH_2F$, —$CHF_2$, —$CF_3$, —$CH_2CF_3$, —$CHFCF_3$, —$CF_2CF_3$, —$CHClCH_3$, —$CH_2CH_2Cl$, —$CH_2CH_2CF_3$, —$CH_2CH_2CH_2CF_3$, $CHClCF_2CH_2CH_3$, $CF_2CH_2CH_2CHF_2$, $CH_2CH_2CH_2CH_2F$, $CH_2CH_2CH_2CH_2Cl$, and the like, The term "hydroxyalkyl" refers to an alkyl radical wherein said alkyl radical is the same as defined for the term "alkyl" except that the alkyl radical additionally has from 1 or 2 hydroxyl groups attached to the alkyl chain. For example, $C_{2-4}$hydroxyalkyl includes 2-hydroxyethyl, 2-hydroxypropyl, 2,4-dihydroxybutyl and the like.

The term "5-member heteroaryl" refers to a heteroaryl ring system radical wherein said heteroaryl contains at least one heteroatom selected from the groups consisting of N, O and S and up to 3 additional heteroatoms selected from the group consisting of N, O and S. If not otherwise defined, the 5-member rings system is optionally substituted with 1-2 substituents selected from halogen, $C_{1-2}$ alkyl, $C_{1-2}$ haloalkyl, or CN. The points of attachment of the optional substituent(s) as well as the rest of the molecule maybe selected from any position wherein there is an open valence. Some examples of 5-member heteroaryls include:

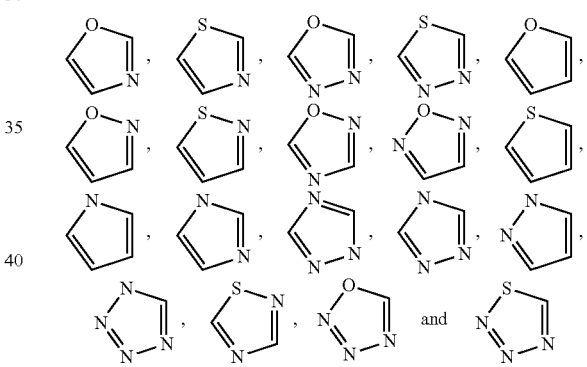

The term "metabolically labile group" refers to a group that some time after administration to an organism, is metabolized in such a way that the metabolically labile group becomes hydrogen. Many metabolic processes exist in organism whereby a chemical group is removed from the rest of the molecule. These metabolic processes include the actions of enzymes wherein esters can be hydrolytically removed at accelerated rates or alkyl groups or other functionalities that can be oxidized by various metabolizing enzymes leading to the ultimate removal of the metabolically labile group and its replacement by hydrogen. In the context of this invention, the metabolically labile group is attached to an oxygen so that when that group is metabolically removed within the target organism, it is eventually replaced by a hydrogen at some point in the metabolic scheme. The metabolism referred to here is typically enzyme assisted but does not have to be so. Therefore, the metabolically labile group can be removed chemically provided that chemical removal occurs after administration to an organism. For example, certain metabolically labile groups might be removed by simple chemical hydrolysis in the stomach, gut or blood. Metabolically labile groups relate to the concept of prodrugs for which those of ordinary skill in the art appreciate are well-known for secondary alcohols. These metabolically labile groups include esters, carbonates, carbamates, simple alkyl groups, phosphates, phosphites, sulfites, sulfates and the like. In certain embodiments of this invention, the organism referred to is a mammal. In some embodiments, the mammal is a human.

The compounds of this invention may be present as solids and when so present, may be in an amorphous form or they may be crystalline. When the compounds of this invention are in the crystalline form, they might be present as a single polymorph or a mixture of polymorphs or even as a mixture of amorphous material together with one or more distinct polymorphs—the invention is not limited according to any particular solid or liquid state form.

The compounds of this invention contain at least one stereocenter and therefore, exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. Thus, "R" and "S" denote the relative configurations of substituents around one or more chiral carbon atoms. When the stereochemistry of a disclosed compound is named or depicted by structure, the named or depicted stereoisomer is at least 50%, 60%, 70%, 80%, 90%, 95%, 98%, 99% or 99.9% by weight pure relative to the other stereoisomers. When a single enantiomer is named or depicted by structure, the depicted or named enantiomer is at least 50%, 60%, 70%, 80%, 90%, 95%, 98%, 99% or 99.9% by weight optically pure. Percent optical purity by weight is the ratio of the weight of the enantiomer over the weight of the enantiomer plus the weight of its optical isomer.

The compounds of the invention may be prepared as individual isomers by incorporating or starting with a specific isomer, isomer-specific synthesis, separation of diastereomers or resolution from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

Where compounds of this invention include one or more basic sites such as amines, acid addition salts can be made and this invention includes such acid addition salts. Some representative (non-limiting) acid addition salts include hydrochloride, hydrobromide, hydroiodide, acetate, benzenesulfonate, mesylate, besylate, benzoate, tosylate, citrate, tartrate, sulfate, bisulfate, lactate, maleate, mandelate, valerate, laurate, caprylate, propionate, succinate, phosphate, salicylate, napsylate, nitrate, tannate, resorcinate and the like, including multiprotic salts as well as mixtures of the acid addition salts. In cases where an amine is present, this invention also embraces quaternized ammonium salts of those amines. It should be appreciated that N-oxides of amines are also embraced within the definition of the compounds of this invention. Likewise, where compounds of this invention include one or more acid sites such as carboxylic acids, phenols and the like, basic addition salts can be made and this invention includes such basic addition salts. For example, some representative (non-limiting) acidic compounds of this invention may be present as their lithium, sodium, potassium, ammonium, trialkyammonium, calcium, magnesium, barium and the like.

The compounds of this invention can also be present as solvates and such solvates are embraced within the scope of this invention even where not explicitly described. Such solvates are preferably hydrates but can be solvates comprised of other solvents, preferably where those solvents are considered to be non-toxic or at least acceptable for administration to mammals, preferably humans. The solvates can be stoichiometric or non-stoichiometric, singular or in combination. Some exemplary solvates include water, ethanol, acetic acid and the like.

The therapeutic utility of these compounds includes "treating" a mammal, preferably a human where treating is understood to include treating, preventing, or ameliorating the symptoms associated with, or reducing the incidence of, reducing the pathogenesis of, facilitating the recovery from or delaying the onset of the syndrome, illness, malady or condition being considered. The compounds of this invention can also be useful in states or conditions where no clear deficit, illness or malady per se is perceived but rather, where a preferred condition, sensation, performance, capability or state is obtainable through therapeutic intervention with a compound of this invention.

The compounds of this invention, when used as therapeutics can be administered by any method known to one of skill in the art such as orally, bucally, intravenously, subcutaneously, intramuscularly, transdermally, intradermally, intravascularly, intranasally, sublingually, intracranially, rectally, intratumorally, intravaginally, intraperitonealy, pulmonary, ocularly and intratumorally.

As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

When administered, the compounds and compositions of this invention maybe given once daily or with multiple daily doses such as twice per day, three times per day and four times per day.

In one embodiment of this invention, the compound is administered orally where it can be formulated for solid dosage administration or liquid dosage administration. Solid dosage administration can be in the form of a tablet, granule, capsule, pill, pellet, powder and the like. Liquid dosage formulations include syrups, solutions, gels, suspensions, elixirs, emulsions, colloids, oils, and the like.

As mentioned previously, the compounds of this invention may be solids and when present as solids, they maybe of defined particle size. Where the compound of this invention is not particularly water soluble, it is sometimes preferable to administer the compound with a certain particle size—a particle size with a preferred range where the average mean particle size diameter is under 100 microns, or 75 microns, or 50 microns, or 35 microns, or 10 microns or 5 microns.

Solid dosage formulations will comprise at least one compound of this invention together with one or more pharmaceutical excipients. Those excipients are known to one of skill in the art and include, by way of non-limiting example diluents (monosaccharides, disaccharides and polyhydric alcohols including starch, mannitol, dextrose, sucrose, microcrystalline cellulose, maltodextrin, sorbitol, xylitol, fructose and the like), binders (starch, gelatin, natural sugars, gums, waxes and the like), disintegrants (alginic acid, carboxymethylcellulose (calcium or sodium), cellulose, crocarmellose, crospovidone, microcrystalline cellulose, sodium starch glycolate, agar and the like), acidic or basic buffering agents (citrates, phoshphates, gluconates, acetates, carbonates, bicarbonates and the like), chelating agents (edetic acid, edetate calcium, edetate disodium and the like), preservatives (benzoic acid, chlorhexidine gluconate, potassium benzoate, potassium sorbate, sorbic acid, sodium benzoate and the like), glidants and lubricants (calcium stearate, oils, magnesium stearate, magnesium trisilicate, sodium fumarate, colloidal silica, zinc stearate, sodium oleate, stearic acid, and the like), antioxidants and/or preservatives (tocopherols, ascorabtes, phenols, and the like) and acidifying agents (citric acid, fumaric acid, malic acid, tartaric acid and the like) as well as coloring agents, coating agents, flavoring agents, suspending agents, dessicants, humectants and other excipients known to those of skill in the art.

The solid dosage formulations of this invention can be prepared in different forms including most commonly, tablets and capsules. The tablets can be formulated by a wide variety of methods known to one of skill in the art including, for example, preparing a dry powder mixture of the drug substance in combination with one or more of the excipients granulating the mixture and pressing to together into a tablet and optionally coating the tablet with an enteric or non-enteric coating. The final coat typically includes a light protective pigment such as titanium oxide and a shellac or wax to keep the tablet dry and stable. While not intending to be limited by theory or example, in some instances it might be preferred to prepare the tablets by wet granulating the drug with one or more of the excipients and then extruding the granulated material.

The solid dosage forms of this invention also include capsules wherein the drug is enclosed inside the capsule either as a powder together with optional excipients or as granules containing usually including one or more excipients together with the drug and wherein the granule in turn can be optionally coated, for example, enterically or non-enterically.

In certain embodiments of this invention, the solid dosage formulations of this invention are formulated in a sustained release formulation. Such formulations are known to those of skill in the art and generally rely on the co-formulation of the drug with one or more matrix forming substances that slow the release of the androgen receptor modulator thus extending the compound's lifetime in the digestive track and thereby extend the compounds half-life. Some non-limiting matrix forming substances include hydroxypropyl methylcellulose, carbopol, sodium carboxymethylcellulose and the like.

In some embodiments of this invention, the compounds are formulated for delivery other than via a solid oral dosage form. For example, in certain instances it might be preferable to deliver a compound of this invention by a pulmonary route. A pulmonary route of administration typically means that the compound of this invention is inhaled into the lung where it is absorbed into the circulation. Such a route of administration has the advantage of avoiding a first pass liver effect thereby possibly increasing bioavailability as well as decreasing or eliminating undesirable androgen agonist effects on the liver such as increasing liver enzymes and/or decreasing HDL. Formulating a compound of the invention for pulmonary delivery can be accomplished by micronizing the compound of the invention to a very fine size particle, typically with a mean average diameter of less than 20 microns, or less than 10 microns or between 2 and 5 microns. The powder may then be inhaled by itself or more likely mixed with one or more excipients such as lactose or maltose. The powder can then be inhaled in a dry powder inhaling device either once or multiple times per day depending on the particular compound and the patients need. Other types of pulmonary dosage forms are also embraced by this invention. In an alternative to the dry powder delivery, the compound of this invention may be suspended in an aerosolizing medium and inhaled as a suspension through a meter dosed inhaler or a nebulizer.

The compounds of this invention can be formulated for transdermal delivery. Effective advantage of these compounds can be taken through a wide variety of transdermal options. For example, the compounds of this invention maybe formulated for passive diffusion patches where they are preferably embedded in a matrix that allows for slow diffusion of the compound into the treated subject's circulation. For this purpose, the compound is preferably dissolved or suspended in solvents including by way of non-limiting examples one or more of ethanol, water, propylene glycol, and Klucel HF. In some instances, a polymer matrix (e.g. acrylate adhesive) will comprise the bulk of the transdermal formulation. In some instances, the transdermal formulations maybe designed to be compatible with alternate transdermal delivery technologies. For example, some transdermal technologies achieve greater and/or more consistent delivery by creating micropores in the skin using radio frequency, heat, ultrasound or electricity. In some cases, the compounds of this invention can be used with microneedle technology wherein the compound is loaded into or onto very small needles which do not need to penetrate the dermis to be effective.

The compounds of this invention may be employed alone or in combination with other therapeutic agents. By way of non-limiting example, the compounds of this invention can be used in combination with anti-lipidemics (statins, fibrates, omega-3 oils, niacinates and the like), bone anti-resorptives (bisphosphonates, estrogens, selective estrogen receptor modulators (SERMs), calcitonin, and the like), bone anabolic agents (PTH and fragments e.g teriparatide, PTHRP and analogues e.g. BaO58), anti-diabetics (e.g. insulin sensitizers, glucose absorption and synthesis inhibitors (e.g. metformin)), anti-anxiety agents, antidepressants, anti-obesity agents, contraceptive agents, anti-cancer agents, PPARγ agonists (e.g. pioglitazone), and the like. When used in combination, the compounds of this invention may be co-formulated or co-administered wherein said co-administration does not require dosing at exactly the same time but rather indicates that the patient is undergoing treatment with one or more of the additional agents during the timeframe of treatment with the selective androgen modulators of this invention. Thus, the additional drug(s) for combination treatment can be administered concomitantly, sequentially or separately from the compounds of this invention.

The compounds of this invention may be administered according to different dosage scheduling and the dosage may be adjusted as deemed necessary by the subject or preferably by the subject in consultation with a qualified practitioner of medicine. Dosing of the compounds of this invention can take place by multiple routes and consequently, the dosing schedule and amounts are dependent not only on the particular subject's weight, sex, age, therapy contemplated, etc but also by the route of the drug chosen.

By way of non-limiting example, the compounds of this invention may be considered for dosing by the oral route in a once daily, twice daily, three times daily or more than three times per day depending on the particular needs of that subject, the formulation of the drug, etc. The dosage will typically be from about 0.01 mg to 500 mg of drug per daily dosage, for example from about 0.1 mg to about 10 mg, such as from about 0.1 mg to about 3 mg, or from about 0.1 mg to about 250 mg of drug per daily dosage, or from about 1 mg to about 150 mg of drug per daily dosage, or from about 5 mg to about 100 mg of drug per daily dosage.

It is understood that the amount of compound dosed per day can be administered every day, every other day, every 2 days, every 3 days, every 4 days, every 5 days, etc. For example, with every other day administration, a 5 mg per day dose can be initiated on Monday with a first subsequent 5 mg per day dose administered on Wednesday, a second subsequent 5 mg per day dose administered on Friday, etc. In one embodiment, a compound of this invention is dosed once every seven days.

The compounds of this invention can also be dosed on a monthly basis meaning that administration is done once per month. In addition, the compounds of this invention can be dosed on a weekly basis (once a week), every other week, every three weeks or every four weeks for a single day or multiple days.

It should be appreciated that the dose interval for the compounds of this invention can be adjusted according to the particular compound used, its dosage, the indication being treated and the patient and/or physician's judgment.

The compounds of this invention can also be dosed on an as needed or "pro re nata" "prn" schedule, and "on demand". In this type of dosing, the compounds of this invention are administered in a therapeutically effective dose at some time prior to commencement of an activity wherein the therapeutic effect of the compounds of this invention is desirable. Administration can be immediately prior to such an activity, including about 0 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, or about 10 hours prior to such an activity, depending on the formulation.

The compounds of this invention can be prepared by a variety of synthetic routes and techniques known to those of skill in the art. The processes disclosed herein should not be construed as limiting the examples or scope of the invention in any way but rather are provided as just some of the representative ways that the compounds of this invention can be or were prepared.

In some cases, protective groups are employed in the synthesis of the compounds of this invention and it should be appreciated that there are a diverse array of protective groups and strategies that can be employed in organic synthesis (T. W. Green and P. G. M. Wuts (2006) Greene's Protective Groups in Organic Synthesis, herein incorporated by reference in its entirety) and that where a protective group is referred to generically, any appropriate protective group should be considered.

In some instances, leaving groups are employed in the synthesis of compounds of this invention. Where a specific leaving group is referred to, it should be appreciated that other leaving groups might also be used. Leaving groups typically include those groups that can stabilize an anion. In the case of nucleophilic aromatic substitutions, the leaving group may be an anion or a neutrally charged group. In some cases, the leaving group for nucleophilic aromatic substitution may be a group that is not typically considered to be a stabilized anion (e.g. fluoride or hydride). While not intending to be bound by theory or the examples, some typical nucleophilic leaving groups include halogens, sulfonates (O-mesylates, O-tosylates, etc), hydrides, quaternized amines, nitro, and the like. Additional discussion and examples can be found in leading textbooks on organic chemistry including, for example, March's Advanced Organic Chemistry: Reactions, Mechanisms, and Structure, 5$^{th}$ Edition, which is herein incorporated in its entirety.

Assignment of stereochemistry—The examples of this invention described herein have at least two stereocenters. Due to the nature of the chemical syntheses used for the preparation of the specific examples of this invention, a set of diastereomers was obtained for each compound synthesized. It was observed that these diastereomers separated fairly readily by silica gel chromatography using EtOAc and hexanes.

The absolute stereochemistry of the diastereomers were assigned by analogy to the single X-Ray crystal solution obtained for one diastereomer (the compound of Example 20) from one of the diastereomeric pairs (compounds of Examples 19 and 20).

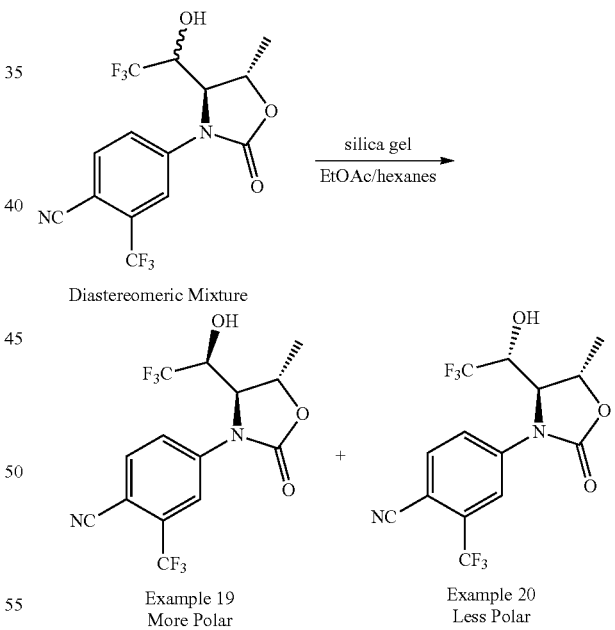

Example 20 was the less polar isomer and was shown to have the structure shown, having 4(R) side chain stereochemistry in accordance with the Cahn-Ingold-Prelog priority rules. Since Example 20 had the 4(R) side chain stereochemistry, Example 19 was assigned as the other diastereomer with 4(S) stereochemistry in accordance with the Cahn-Ingold-Prelog priority rules. In addition, Example 20 also demonstrated lower androgen receptor binding affinity than Example 19:

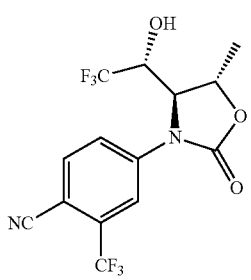 [SMILES: C[C@@H]1OC(=O)N(c2ccc(C#N)c(C(F)(F)F)c2)[C@H]1[C@@H](O)C(F)(F)F]

Example 20

Less Polar Isomer (SiO₂ 50% EtOAc/hexanes; $R_f$=0.5)

(Structure Established by Single Crystal X-Ray)

AR Binding $IC_{50}$=72 nM

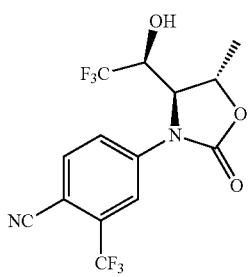 [SMILES: C[C@@H]1OC(=O)N(c2ccc(C#N)c(C(F)(F)F)c2)[C@H]1[C@H](O)C(F)(F)F]

Example 19

More Polar Isomer (SiO₂ 50% EtOAc/hexanes; $R_f$=0.2)

AR binding $IC_{50}$=4 nM

For all of the specific examples of this invention, each diastereomeric pair included one isomer that was clearly less polar than the other (EtOAc/hexanes on silica gel thin layer chromatography). The less polar isomer also had weaker affinity for the androgen receptor as measured by assays described herein. Accordingly, the less polar isomer which was also, in every case, the less active isomer was assigned the same 4(R) side chain stereochemistry as the compound of Example 20.

Despite the efforts to determine the actual structural formula for each pair of diatereomers as described above, it is possible that one or more pairs could be inadvertently assigned the wrong absolute stereochemistry. One of ordinary skill in the art appreciates that both possible diastereomers can be produced after addition of the CF₃ group and that these diastereomers can be separated. One diastereomer will have from slightly better to significantly better affinity for the androgen receptor than the other, though in many cases both have demonstrable activity in in vitro binding and/or in vivo experiments such as the rat Herschberger assay. Both isomers are included under various embodiments of this invention.

EXPERIMENTAL PROCEDURES

Examples 1 and 2

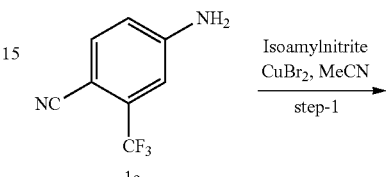

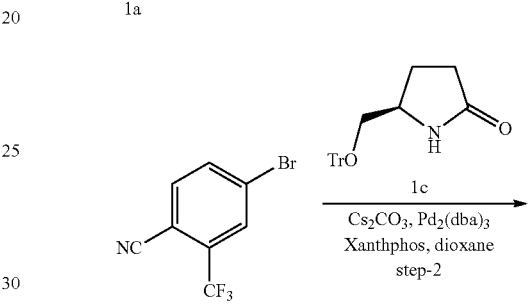

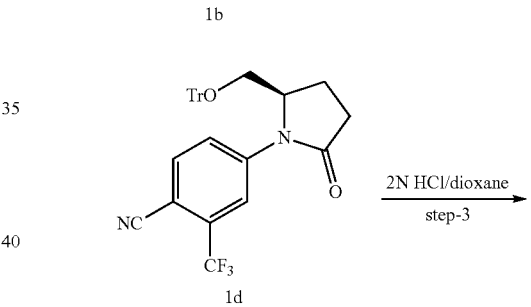

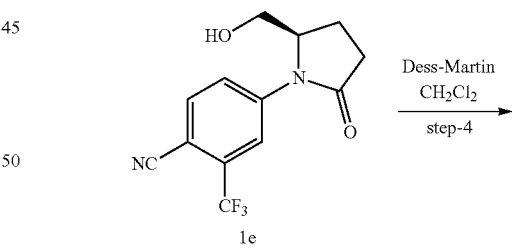

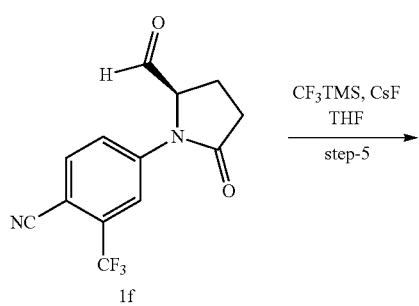

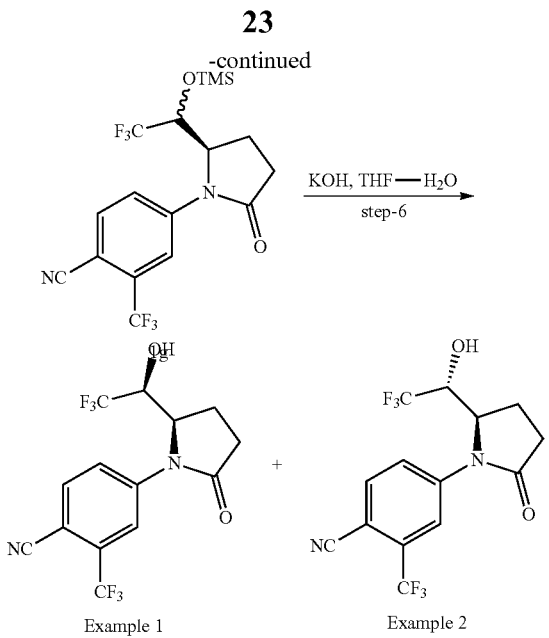

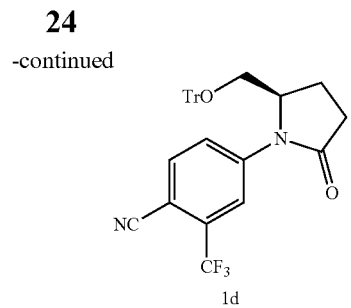

To a solution of bromo 1b (3 g, 12.0 mmol) dissolved in 1,4-Dioxane (40 mL), (R)-5-((trityloxy)methyl)pyrrolidin-2-one 1c (4 g, 11.2 mmol) was added at room temperature followed by $Cs_2CO_3$ (4.2 g, 13 mmol) and Argon gas was purged for 30 min. To the reaction mixture $Pd_2(dba)_3$ (0.5 g, 0.55 mmol) and Xanthphos (0.8 g, 1.38 mmol) were added at room temperature. The resulting reaction mixture was then heated to 100° C. for 16 h. After completion of the reaction (by TLC), the reaction mixture was filtered through celite bed. The celite bed was washed with EtOAc (5 mL) and the filtrates were combined, dried over $Na_2SO_4$ and concentrated under reduced pressure to give the crude compound. The crude material was purified by column chromatography to furnish the Trityl ether 1d (3.1 g, 50%) as off white solid.

TLC: 40% EtOAc/Hexane ($R_f$: 0.3)

$^1$H NMR (500 MHz, $CDCl_3$, δ in ppm): 8.30 (s, 1H), 8.09 (d, J=9.0 Hz, 1H), 7.88 (t, J=8.5 Hz, 1H), 7.22-7.19 (m, 10H), 7.15-7.14 (m, 5H), 4.81 (d, J=6.0 Hz, 1H), 3.21 (dd, J=10.5 Hz, 3.0 Hz, 1H), 3.13 (dd, J=10.5 Hz, 3.5 Hz, 1H), 2.83-2.76 (m, 1H), 2.56-2.54 (m, 1H), 2.36-2.25 (m, 1H), 2.03-1.99 (m, 1H).

Mass (ESI): 527.2 [M$^+$+1].

(R)-4-(2-(hydroxymethyl)-5-oxopyrrolidin-1-yl)-2-(trifluoromethyl)benzonitrile 1e

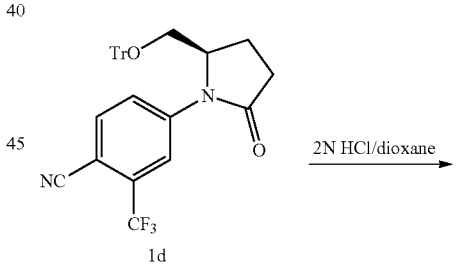

4-bromo-2-(trifluoromethyl)benzonitrile Intermediate 1b

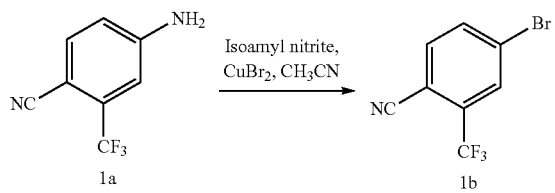 [SMILES: N#Cc1ccc(N)cc1C(F)(F)F ; N#Cc1ccc(Br)cc1C(F)(F)F]

To a solution of 4-amino-2-(trifluoromethyl)benzonitrile (1a) (5.0 g, 26.9 mmol) in $CH_3CN$ (50 mL), cooled to 0° C., Isoamyl nitrite (6 mL, 40.9 mmol) was added and stirred for 30 min. Then $CuBr_2$ (7.1 g, 32.0 mmol) was added portion wise to the reaction mixture maintaining the temperature at 0° C. The reaction mixture was slowly warmed to room temperature and stirred for further 4 h. After completion of reaction (by TLC), the reaction mixture was poured into saturated NaCl solution and extracted with EtOAc (3×70 mL). The combined organic extracts were dried over $Na_2SO_4$ and concentrated under reduced pressure to provide the crude residue which was purified by column chromatography to afford the bromo 1b (5 g, 74%) as a syrup.

TLC: 30% EtOAc/Hexane ($R_f$: 0.8)

$^1$H NMR (500 MHz, $CDCl_3$, δ in ppm): 7.95 (s, 1H), 7.85 (d, J=8.5 Hz, 1H), 7.71 (d, J=8.5 Hz, 1H).

(R)-4-(2-oxo-5-((trityloxy)methyl)pyrrolidin-1-yl)-2-(trifluoromethyl)benzonitrile (1c)

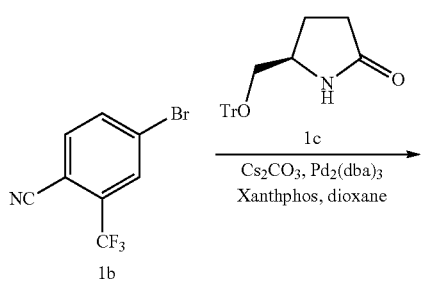

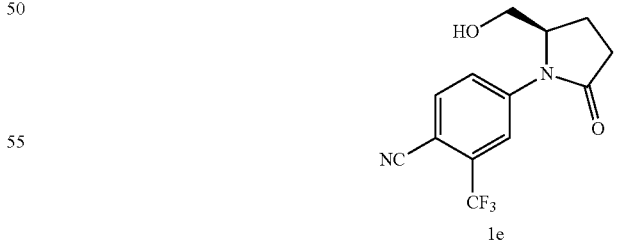

To a solution of (R)-4-(2-oxo-5-((trityloxy)methyl)pyrrolidin-1-yl)-2-(trifluoro methyl)benzonitrile 1d (3 g, 5.69 mmol) in 1,4-dioxane (30 mL), cooled to 0° C., 2M HCl in dioxane (30 mL) was added. The reaction mixture was then warmed up to room temperature and stirred for 16 h. After completion (by TLC), the reaction mixture was diluted with $H_2O$ (20 mL) and extracted with EtOAc (3×75 mL). The combined organic extracts were dried over $Na_2SO_4$ and concentrated under reduced pressure. The crude material was purified by column chromatography to afford the alcohol 1e (1.6 g, 93%) as a white solid.

TLC: 50% EtOAc/Hexane ($R_f$: 0.2)

$^1$H NMR (500 MHz, $CDCl_3$, δ in ppm): 8.48 (s, 1H), 8.16 (d, J=8.5 Hz, 1H), 7.98 (dd, J=8.5 Hz, 2.0 Hz, 1H), 4.93 (t, J=5.5 Hz, 1H), 4.63-4.60 (dd, J=8.5, 4.0 Hz, 1H), 3.58-3.53 (m, 1H), 3.48-3.44 (m, 1H), 2.75-2.68 (m, 1H), 2.46-2.40 (m, 1H), 2.25-2.17 (m, 1H), 2.05-1.99 (m, 1H).

4-((R)-2-oxo-5-((S)-2,2,2-trifluoro-1-hydroxyethyl) pyrrolidin-1-yl)-2-(trifluoromethyl)benzonitrile (Example 1) &

4-((R)-2-oxo-5-((R)-2,2,2-trifluoro-1-hydroxyethyl) pyrrolidin-1-yl)-2-(trifluoromethyl)benzonitrile (Example 2)

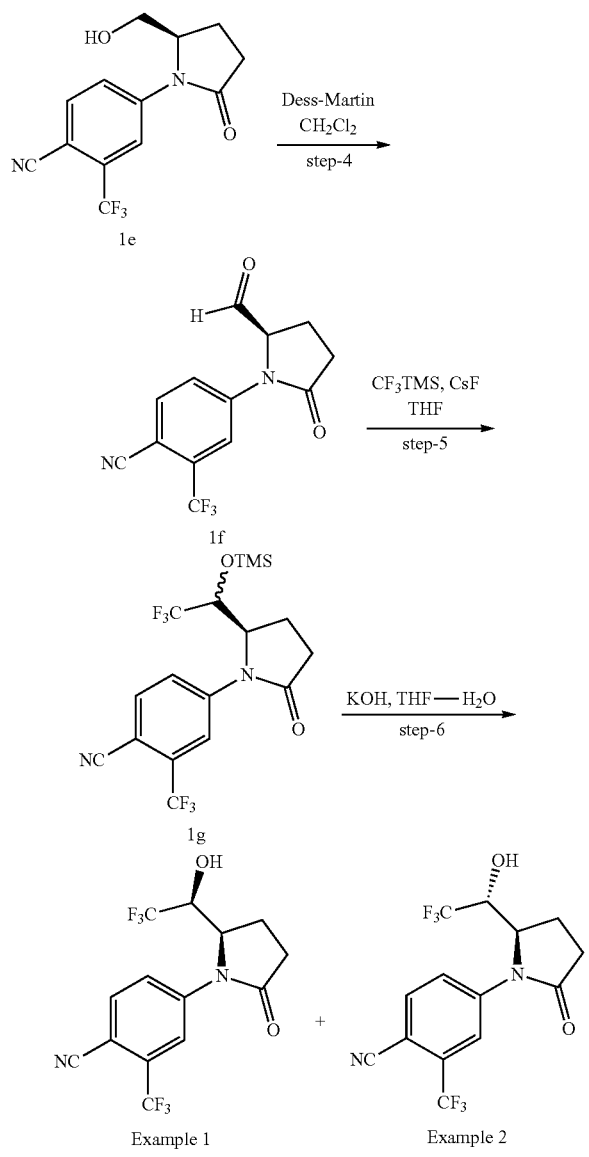

Examples 1 and 2

To a solution of (R)-4-(2-(hydroxymethyl)-5-oxopyrrolidin-1-yl)-2-(trifluoro methyl)benzonitrile (1e) (1.0 g, 3.53 mmol) in $CH_2Cl_2$ (50 mL), cooled to 0° C., Dess-Martin periodinane (2.9 g, 7.0 mmol) was added. The reaction mixture was slowly warmed to room temperature, stirred for 6 h and quenched with saturated $NaHCO_3$ solution (50 mL) and extracted with EtOAc (3×75 mL). The combined organic extracts were dried over $Na_2SO_4$ and concentrated under reduced pressure to provide the aldehyde 1f (1.0 g, crude) which was carried forward to the next step without any purification.

TLC: 50% EtOAc/Hexane ($R_f$: 0.5)

The crude aldehyde 1f (1.0 g, 3.56 mmol) was dissolved in dry THF (50 mL), cooled to 0° C., and CsF (0.6 g, 3.97 mmol) followed by $CF_3TMS$ (6 mL, 35.0 mmol) was added and stirred for 6 h. After completion of reaction (by TLC), the reaction mixture was quenched with aqueous $NH_4Cl$ and extracted with EtOAc (3×75 mL). The combined organic extracts were dried over $Na_2SO_4$ and concentrated under reduced pressure to furnish the crude silyl ether 1g (1.2 g) as a mixture of diastereomers. The crude material was used for the next step without purification.

TLC: 50% EtOAc/Hexane $R_f$: (0.7 & 0.8)

The crude silyl ether 1g (1.2 g, 2.83 mmol) was taken in THF (50 mL) and KOH (0.46 g, 8.36 mmol) dissolved in $H_2O$ (50 mL) was added at 0° C. and stirred for 1 h. After completion of reaction (by TLC), the reaction mixture was diluted with $H_2O$ (20 mL) and extracted with EtOAc (3×75 mL). The combined organic extracts were dried over $Na_2SO_4$ and concentrated under reduced pressure to give the crude residue which was purified by column chromatography to afford Example 1 (0.1 g) and Example 2 (0.4 g) both as white solids.

TLC: 50% EtOAc/Hexane $R_f$: (0.2 (Example 1) & 0.4 (Example 2)

Example 1

$^1$H NMR (500 MHz, $CDCl_3$, δ in ppm) (Example 1): 8.22 (d, J=1.5 Hz, 1H), 8.16 (t, J=8.5 Hz, 1H), 8.02 (dd, J=8.5 Hz, 2.0 Hz, 1H), 6.69 (d, J=6.5 Hz, 1H), 4.97 (t, J=6.0 Hz, 1H), 4.31-4.27 (m, 1H), 2.81-2.76 (m, 1H), 2.45-2.35 (m, 2H), 2.07-2.03 (m, 1H).

Mass (ESI): 351.0 [M$^+$–1]

HPLC purity: 98.26%

Example 2

$^1$H NMR (500 MHz, $CDCl_3$, δ in ppm): 8.29 (s, 1H), 8.24 (d, J=8.0 Hz, 1H), 7.93 (d, J=9.0 Hz, 1H), 6.74 (d, J=6.5 Hz, 1H), 4.98 (d, J=5.5 Hz, 1H), 4.09 (t, J=7.5 Hz, 1H), 2.70-2.65 (m, 1H), 2.50-2.48 (m, 1H), 2.24-2.19 (m, 2H).

Mass (ESI): 351.0 [M$^+$–1]

HPLC purity: 97.1%

Example 3 & Example 4

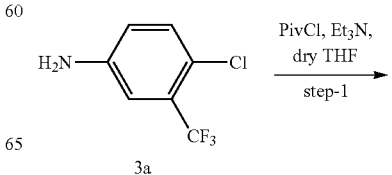

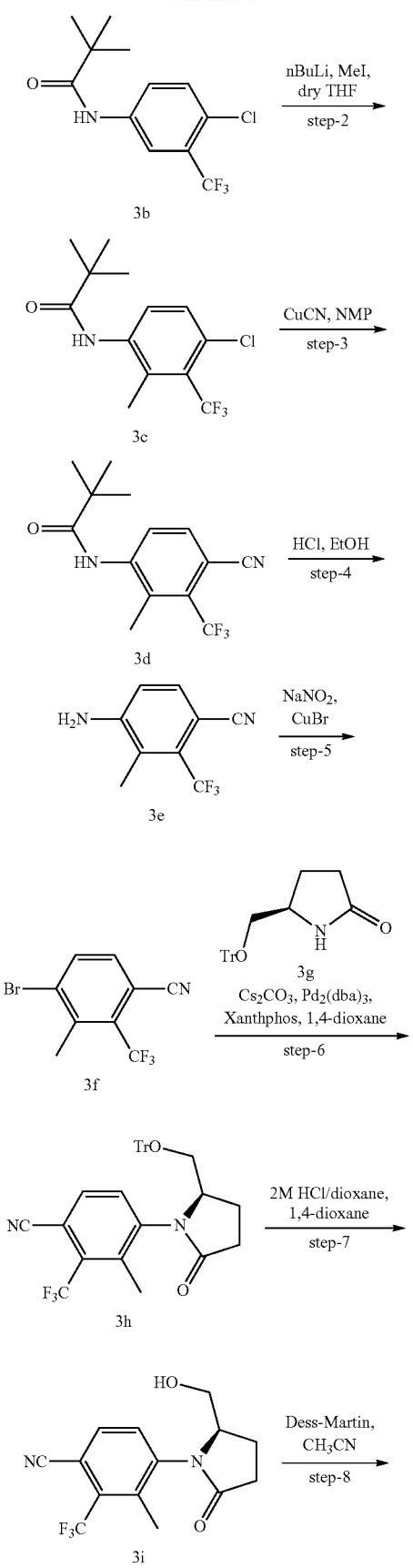
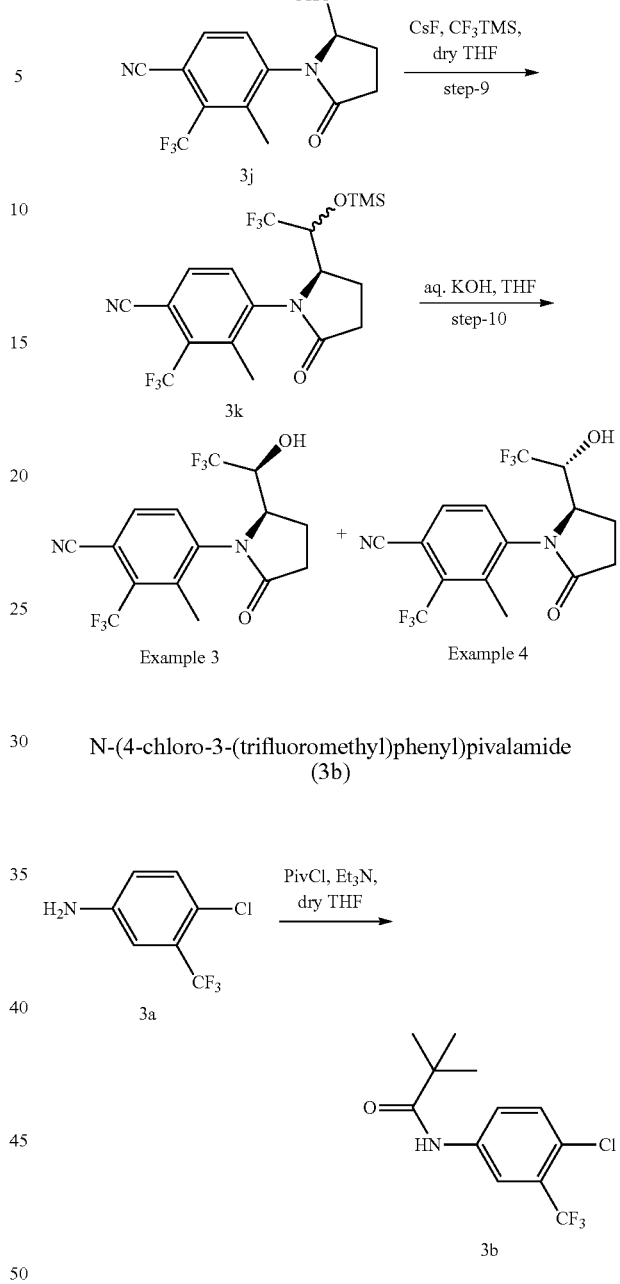

N-(4-chloro-3-(trifluoromethyl)phenyl)pivalamide (3b)

To a solution of 4-chloro-3-(trifluoromethyl) aniline (3a) (0.5 g, 2.55 mmol) in dry THF (8 mL), cooled to 0° C., Et₃N (0.4 mL, 2.76 mmol) followed by PivCl (0.34 mL, 2.8 mmol) were added. The reaction mixture was stirred at room temperature for 4 h. After completion of reaction (by TLC), the reaction mixture was diluted with water (20 mL) and extracted with EtOAc (3×15 mL). The combined organic extracts were washed with water (30 mL). The organic layer was separated dried over Na₂SO₄ and concentrated under reduced pressure to give the crude material which was triturated with n-hexane to afford the desired amide 3b (0.45 g, 60%) as a white solid.

TLC: 35% EtOAc/Hexane ($R_f$: 0.4)

$^1$H NMR (200 MHz, CDCl₃, δ in ppm): 7.87 (d, J=2.6 Hz, 1H), 7.74 (dd, J=8.8 Hz, 2.6 Hz, 1H), 7.44 (d, J=8.6 Hz, 2H), 1.33 (s, 9H).

Mass (ESI): 280.1 [M⁺]

N-(4-chloro-2-methyl-3-(trifluoromethyl)phenyl) pivalamide (3c)

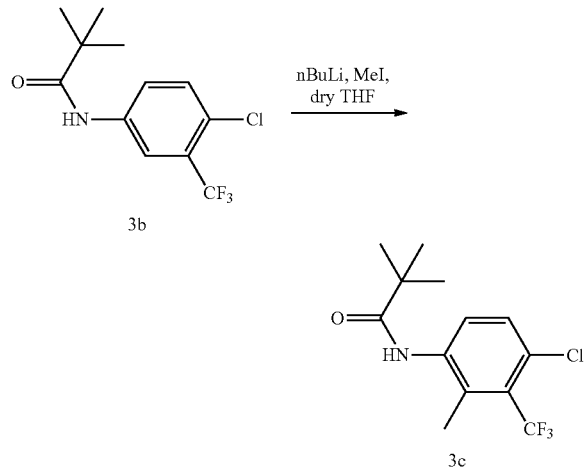

N-(4-chloro-3-(trifluoromethyl)phenyl)pivalamide (3b) (3 g, 10.7 mmol) was dissolved in dry THF (30 mL), cooled to 0° C., and n-BuLi (15.6 mL, 25.7 mmol) was added. After 3 h, a solution of MeI (0.66 mL, 10.56 mmol) in THF (7 mL) was added to the reaction mixture maintaining the temperature at 0° C. and stirred for further 3 h. and quenched with aqueous NH$_4$Cl solution. The reaction mixture was extracted with EtOAc (3×30 mL). The combined organic extracts were dried over Na$_2$SO$_4$ and concentrated under reduced pressure to give the crude material which was purified by column chromatography to afford N-(4-chloro-2-methyl-3-(trifluoromethyl) phenyl)pivalamide (3c) (2.0 g, 64%) as off white solid.
TLC: 40% EtOAc/Hexane (R$_f$: 0.5)
$^1$H NMR (200 MHz, CDCl$_3$, δ in ppm): 7.76 (d, J=8.8 Hz, 1H), 7.35 (d, J=8.6 Hz, 1H), 7.21 (br s, 1H), 2.38-2.34 (m, 3H), 1.35 (s, 9H).
Mass (ESI): 293.9 [M$^+$+1]

N-(4-cyano-2-methyl-3-(trifluoromethyl)phenyl) pivalamide (3d)

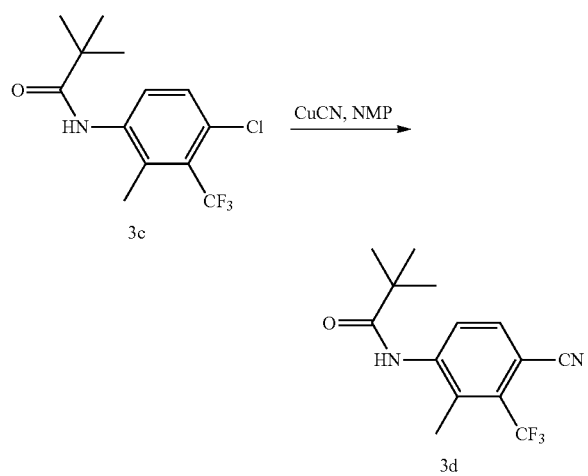

To a solution of N-(4-chloro-2-methyl-3-(trifluoromethyl) phenyl) pivalamide (3c) (0.4 g, 1.36 mmol) in NMP (5 mL) CuCN (0.3 g, 34.0 mmol) was added at room temperature under nitrogen atmosphere and heated to 220° C. for 36 h. The reaction mixture was slowly brought to room temperature, diluted with water (10 mL) and extracted with EtOAc (3×15 mL). The combined organic extracts were dried over Na$_2$SO$_4$ and concentrated under reduced pressure to give the crude compound which was purified by column chromatography to furnish the nitrile 3d (0.2 g, 52%) as a white solid.
TLC: 30% EtOAc/Hexane (R$_f$: 0.5)
$^1$H NMR (200 MHz, CDCl$_3$, δ in ppm): 8.43 (d, J=8.4 Hz, 1H), 7.69 (d, J=8.4 Hz, 1H), 7.51 (br s, 1H), 2.39 (d, J=1.2 Hz, 3H), 1.36 (s, 9H).
Mass (ESI): 284.9 [M$^+$+1]

4-amino-3-methyl-2-(trifluoromethyl)benzonitrile (3e)

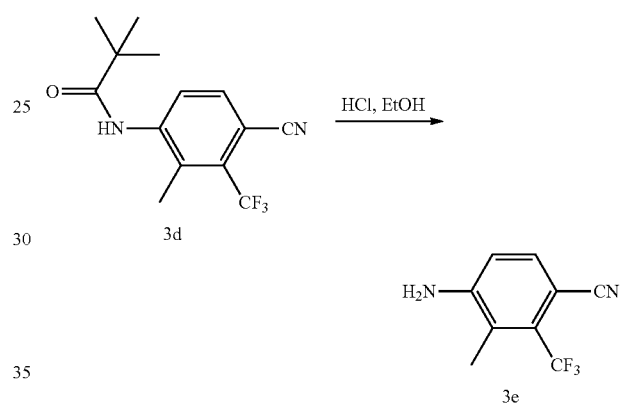

N-(4-cyano-2-methyl-3-(trifluoromethyl)phenyl)pivalamide (3d) (1.5 g, 5.28 mmol) was taken in EtOH/HCl (30 mL, 1:1) and heated to 80° C. for 12 h. The reaction was slowly brought to room temperature and poured into ice cold water (30 mL) during which white solid precipitated which was filtered. The solid was washed with hexane (3×20 mL) and dried under vacuum to provide the amine 3e (0.9 g, 90%) as a white solid.
TLC: 40% EtOAc/Hexane (R$_f$: 0.3)
$^1$H NMR (200 MHz, DMSO-d$_6$, δ in ppm): 7.51 (d, J=8.2 Hz, 1H), 6.91 (d, J=8.6 Hz, 1H), 6.45 (br s, 2H), 2.15-2.12 (m, 3H).
Mass (ESI): 198.9 [M$^+$-]

4-bromo-3-methyl-2-(trifluoromethyl)benzonitrile (3f)

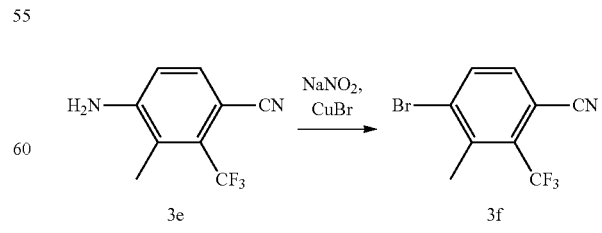

To a solution of 4-amino-3-methyl-2-(trifluoromethyl) benzonitrile (3e) (0.8 g, 4.0 mmol) in water (2 mL), cooled to 0° C., 48% aqueous HBr (10 mL, 18.5 mmol) was added followed by NaNO₂ (0.33 g, 4.8 mmol) taken in water (2 mL) and stirred for 10 min. To the reaction mixture a solution of CuBr (2.7 g, 18.8 mmol) in HBr (10 mL) was added at 0° C. and slowly warmed to room temperature and then heated to 50° C. for 1 h. The reaction mixture was brought to room temperature, diluted with water (50 mL) and extracted with EtOAc (3×20 mL). The combined organic extracts were washed with water (2×20 mL), dried over Na₂SO₄ and concentrated under reduced pressure to give the crude compound which was purified by column chromatography to provide the bromo 3f (0.6 g, 60%) as a tan colored solid.

TLC: 10% EtOAc/Hexane R_f: (0.6)

¹H NMR (500 MHz, CDCl₃, δ in ppm): 7.88 (d, J=9.0 Hz, 1H), 7.52 (d, J=8.0 Hz, 1H), 2.62 (s, 3H).

(R)-3-methyl-4-(2-oxo-5-((trityloxy)methyl)pyrrolidin-1-yl)-2-(trifluoromethyl)benzonitrile (3h)

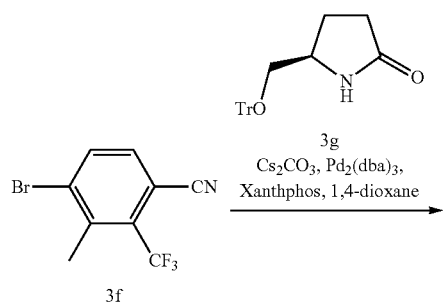

The bromo-compound 3f (0.5 g, 1.89 mmol) was dissolved in 1,4-dioxane (10 mL) and (R)-5-((trityloxy)methyl)pyrrolidin-2-one (3g) (0.54 g, 1.51 mmol) was added followed by Cs₂CO₃ (1.2 g, 3.78 mmol) at room temperature. The reaction mixture was degassed with Argon gas for 30 min, Pd₂(dba)₃ (0.17 g, 0.18 mmol) and Xanthphos (0.21 g, 0.37 mmol) were added and heated to 80° C. for 12 h. After completion of reaction (by TLC), the reaction mixture was diluted with water (20 mL), filtered through celite bed and the filtrate was washed with water (2×20 mL). The organic layer was separated, dried over Na₂SO₄ and concentrated under reduced pressure to give the crude compound which was purified by column chromatography to afford (R)-3-methyl-4-(2-oxo-5-((trityloxy)methyl)pyrrolidin-1-yl)-2-(trifluoromethyl)benzonitrile (3h) (0.26 g, 26%) as a brown solid.

TLC: 50% EtOAc/Hexane R_f: (0.2)

¹H NMR (500 MHz, DMSO-d₆, δ in ppm): 8.07 (d, J=7.5 Hz, 1H), 7.87 (d, J=8.0 Hz, 1H), 7.23 (s, 10H), 7.02 (s, 5H), 4.62 (br s, 1H), 3.09-2.07 (m, 1H), 2.99-2.97 (m, 1H), 2.46-2.45 (m, 1H), 2.29 (br s, 2H), 2.07 (s, 3H), 1.99-1.95 (m, 1H).

Mass (ESI): 541.3 [M⁺+1]

(R)-4-(2-(hydroxymethyl)-5-oxopyrrolidin-1-yl)-3-methyl-2-(trifluoromethyl)benzonitrile (3i)

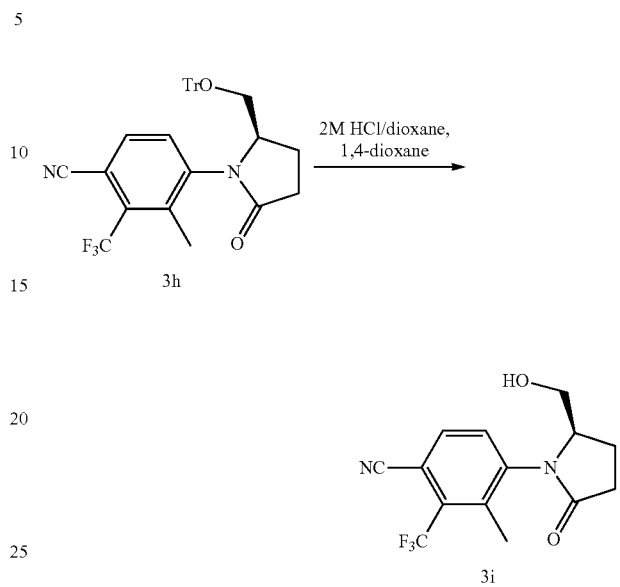

To a solution of (R)-3-methyl-4-(2-oxo-5-((trityloxy)methyl)pyrrolidin-1-yl)-2-(trifluoromethyl)benzonitrile (3h) (0.48 g, 0.93 mmol) in 1,4-dioxane (15 mL), 2M HCl in 1,4-dioxane (5 mL) was added at 0° C. and stirred for 4 h. After completion of reaction (by TLC), the reaction mixture was diluted with water (20 mL) and extracted with EtOAc (2×15 mL). The combined organic extracts were washed with water (2×30 mL), dried over Na₂SO₄ and concentrated under reduced pressure to obtain the crude compound was purified by column chromatography to provide the alcohol 3i (0.22 g, 79%) as a white solid.

TLC: 80% EtOAc/Hexane R_f: (0.2)

¹H NMR (500 MHz, DMSO-d₆, δ in ppm): 8.02 (d, J=7.5 Hz, 1H), 7.83 (br s, 1H), 4.82 (br s, 1H), 4.34 (br s, 1H), 3.39-3.33 (m, 2H), 2.56-2.53 (m, 1H), 2.46-2.41 (m, 1H), 2.31 (s, 3H), 2.28-2.25 (m, 1H), 2.08-2.01 (m, 1H).

3-methyl-4-((R)-2-oxo-5-((S)-2,2,2-trifluoro-1-hydroxyethyl)pyrrolidin-1-yl)-2-(trifluoromethyl)benzonitrile 3 &

3-methyl-4-((R)-2-oxo-5-((R)-2,2,2-trifluoro-1-hydroxyethyl)pyrrolidin-1-yl)-2-(trifluoromethyl)benzonitrile 4

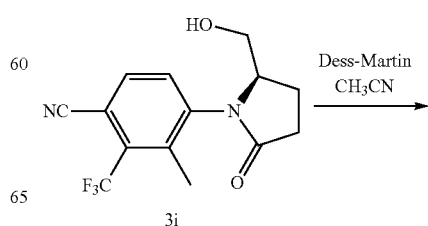

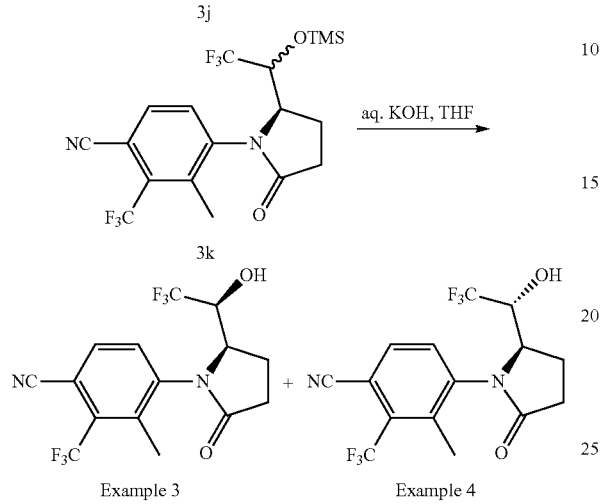

Example 3 Example 4

3i to 3j

The alcohol 3i (0.29 g, 0.97 mmol) was dissolved in $CH_3CN$ (10 mL), cooled to 0° C., and Dess-Martin periodinane (0.62 g, 1.46 mmol) was added and stirred for 3 h. After completion of reaction (by TLC), the reaction mixture was quenched with aqueous $NaHCO_3$ solution (20 mL) and extracted with EtOAc (2×15 mL). The combined organic extracts were washed with water (2×20 mL), separated, dried over $Na_2SO_4$ and concentrated under reduced pressure to furnish the aldehyde 3j (0.22 g, crude) as a white solid which was taken to the next step without purification.

TLC: 10% $MeOH/CH_2Cl_2$ $R_f$: (0.5)

3j to 3k

The aldehyde 3j (0.22 g, 0.87 mmol) was dissolved in dry THF (10 mL), cooled to 0° C., CsF (0.13 g, 0.87 mmol) followed by $CF_3TMS$ (1.2 mL, 8.43 mmol) were added and stirred for 1 h. After completion of reaction (by TLC), the reaction mixture was quenched with aqueous $NH_4Cl$ solution and extracted with EtOAc (2×20 mL). The combined organic extracts were washed with water (2×10 mL), separated, dried over $Na_2SO_4$ and concentrated under reduced pressure to give the crude silyl ether 3k as a mixture of diastereomers (0.23 g, crude). The crude material was carried further without purification.

TLC: 60% EtOAc/Hexane $R_f$: (0.4 & 0.6)

3k to Example 3 and 4

The silyl ether 3k (0.23 g, 0.52 mmol) was taken in dry THF (5 mL), cooled to 0° C., and a solution of KOH (0.088 g, 1.57 mmol) in $H_2O$ (2 mL) was slowly added and stirred for 1 h. After completion of reaction (by TLC), the reaction mixture was diluted with $H_2O$ (20 mL) and extracted with EtOAc (3×15 mL). The combined organic extracts were dried over $Na_2SO_4$ and concentrated under reduced pressure to give the crude residue which was purified by column chromatography to afford Example 3 (0.022 g) and Example 4 (0.018 g) both as white solids.

TLC: 80% EtOAc/Hexane $R_f$: (0.2 Example 3 & 0.6 Example 4).

Example 3

$^1H$ NMR (500 MHz, DMSO-$d_6$, δ in ppm): 7.99 (d, J=8.0 Hz, 1H), 7.90 (d, J=8.0 Hz, 1H), 6.64 (d, J=6.0 Hz, 1H), 4.60 (m, 1H), 4.27-4.26 (m, 1H), 2.68-2.64 (m, 1H), 2.50-2.36 (m, 2H), 2.31 (s, 3H), 2.08 (m, 1H).

Mass (ESI): 365.3 [M$^+$−1]

HPLC purity: 98.10%

Example 4

$^1H$ NMR (500 MHz, DMSO-$d_6$, δ in ppm): 8.07 (d, J=8.0 Hz, 1H), 7.93 (d, J=8.0 Hz, 1H), 6.69 (d, J=6.5 Hz, 1H), 4.69 (br s, 1H), 3.91-3.82 (m, 1H), 2.36-2.29 (m, 6H), 2.16 (br s, 1H).

Mass (ESI): 365.1 [M$^+$−1]

HPLC purity: 96.33%

Examples 5 and 6

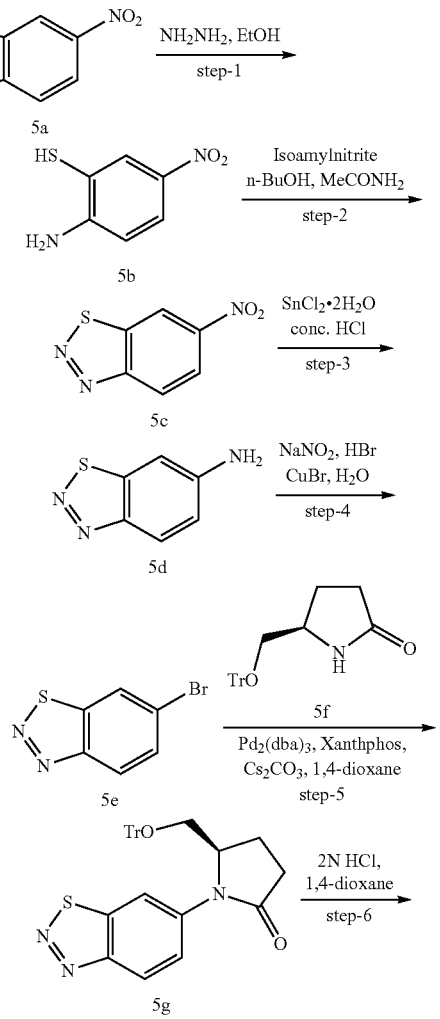

-continued

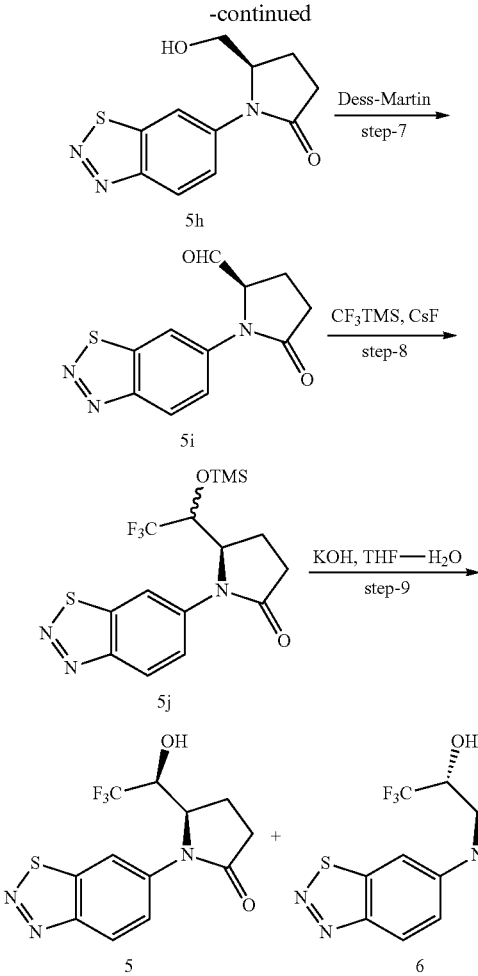

5a to 5b

2-Amino-5-nitrobenzenethiol

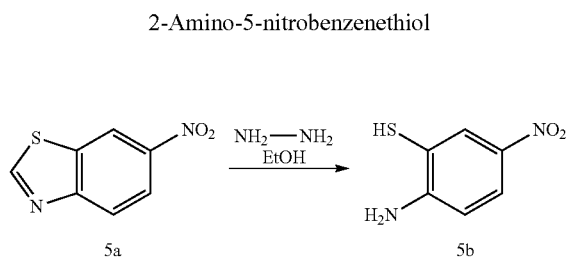

To a solution of 6-Nitrobenzo[d]thiazole (5a) (10 g, 55.5 mmol) in EtOH (100 mL), Hydrazine hydrate (39 g, 77.9 mmol) was added at room temperature under nitrogen atmosphere. The reaction mixture was stirred at room temperature for 4 h. After completion of the reaction (by TLC) the volatiles were removed under reduced pressure, the residue was neutralized with 1N HCl (100 mL) and extracted with EtOAc (3×150 mL). The combined organic extracts were dried over Na₂SO₄ and concentrated under reduced pressure to afford 2-Amino-5-nitrobenzenethiol (5b) (7.0 g, crude). The crude material was taken to the next step without purification.

TLC: 30% EtOAc/Hexane ($R_f$: 0.2)

5b to 5c

6-Nitrobenzo[d][1,2,3]thiadiazole

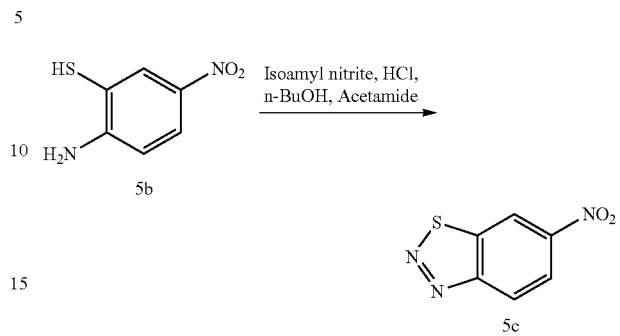

To a solution of 2-Amino-5-nitrobenzenethiol (5b) (6.0 g, 35.3 mmol) in n-BuOH (30 mL), cooled to 0° C., a solution of Isoamyl nitrite (5.0 mL, 37.1 mmol) in n-BuOH (30 mL) was added followed by conc. HCl (5.0 ml). The reaction mixture was warmed to room temperature and stirred for 5 h. To the resulting reaction mixture Acetamide (0.4 ml) was added and stirred for another 30 min at room temperature. After completion of reaction (by TLC), the reaction mixture was diluted with H₂O (80 mL) and extracted with EtOAc (3×150 mL). The combined organic extracts were washed with brine solution (100 mL), dried over Na₂SO₄ and concentrated under reduced pressure to obtain the crude material which was purified by column chromatography to afford 6-Nitrobenzo[d][1,2,3]thiadiazole (5c) (3.5 g, 54%) as a yellow solid.

TLC: 30% EtOAc/Hexane ($R_f$: 0.8)

¹H NMR (200 MHz, CDCl₃, δ in ppm): 9.05 (d, J=1.8 Hz, 1H), 8.80 (d, J=9.0 Hz, 1H), 8.51 (dd, J=9.2 Hz, 2.2 Hz, 1H).

5c to 5d

Benzo[d][1,2,3]thiadiazol-6-amine

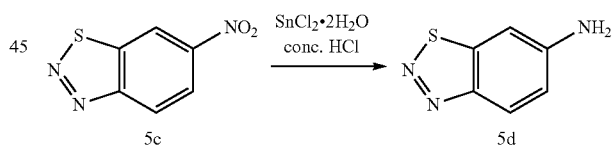

6-Nitrobenzo[d][1,2,3]thiadiazole (5c) (4.0 g, 22.1 mmol) was taken in conc. HCl (100 mL), cooled to 0° C., and SnCl₂.H₂O (15 g, 66.5 mmol) dissolved in conc. HCl (80 mL) was added. The resulting reaction mixture was slowly brought to room temperature and stirred for 5 h. After completion of reaction (by TLC), the reaction mixture was diluted with water (50 mL), neutralized with saturated NaHCO₃ solution (pH~8-9) and extracted with EtOAc (3×150 mL). The combined organic extracts were dried over Na₂SO₄ and concentrated under reduced pressure to give the crude compound which was purified by column chromatography to furnish the amine 5d (2.8 g, 82%).

TLC: 30% EtOAc/Hexane ($R_f$: 0.2)

¹H NMR (200 MHz, CDCl₃, δ in ppm): 8.34 (d, J=9.0 Hz, 1H), 7.14 (d, J=2.2 Hz, 1H), 6.93 (dd, J=8.8 Hz, 2.0 Hz, 1H), 4.23 (br s, 2H).

Mass (ESI): 152.0 [M⁺+1]

5d to 5e

6-Bromobenzo[d][1,2,3]thiadiazole

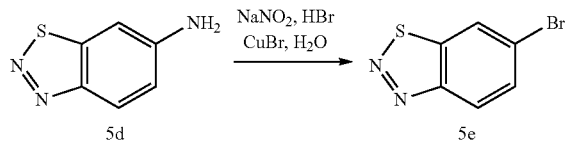 [SMILES: Nc1ccc2nnsc2c1 ; Brc1ccc2nnsc2c1]

To a solution of Benzo[d][1,2,3]thiadiazol-6-amine (5d) (0.5 g, 3.31 mmol) in H$_2$O (10 mL), cooled to 0° C., HBr (13 mL) was added drop-wise followed by a solution of NaNO$_2$ (252 mg, 3.65 mmol) in H$_2$O (4 mL). After 1 h, a solution of CuBr (0.62 g, 4.33 mmol) in HBr (13 mL) was added to the reaction mixture maintaining the temperature at 0° C. The resulting reaction mixture was heated to 80° C. for 2 h. After completion of reaction (by TLC), the reaction mixture was diluted with water (30 mL) neutralized with saturated NaHCO$_3$ solution and extracted with Et$_2$O (3×35 mL). The combined organic extracts were dried over Na$_2$SO$_4$ and concentrated under reduced pressure to give the crude compound was purified by column chromatography to give the bromo 5e (0.25 g, 35%).

TLC: 30% EtOAc/Hexane (R$_f$: 0.8)

$^1$H NMR (500 MHz, CDCl$_3$, δ in ppm): 8.49 (d, J=8.5 Hz, 1H), 8.28 (d, J=1.5 Hz, 1H), 7.76 (d, J=8.0 Hz, 1H).

5e to 5g

(R)-1-(benzo[d][1,2,3]thiadiazol-6-yl)-5-(trityloxymethyl)pyrrolidin-2-one

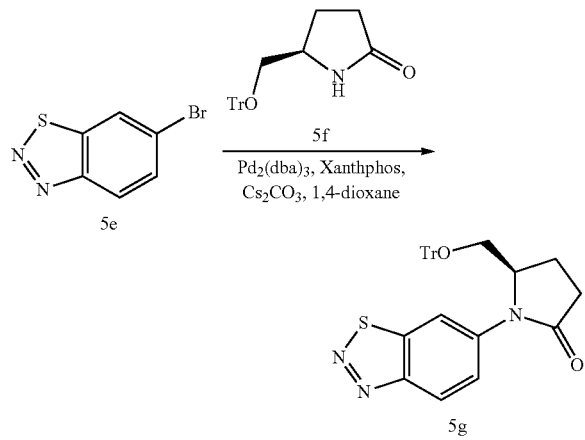

To a solution of 6-Bromobenzo[d][1,2,3]thiadiazole (5e) (175 mg, 0.81 mmol) and (R)-5-(trityloxymethyl)pyrrolidin-2-one (5f) (290 mg, 0.81 mmol) in 1,4-dioxane (20 mL), Cs$_2$CO$_3$ (0.292 g, 0.89 mmol) was added at room temperature and degassed with Argon for 30 min. To the reaction mixture Pd$_2$(dba)$_3$ (0.040 g, 0.04 mmol) and Xanthphos (0.057 g, 0.09 mmol) were added at room temperature and heated to 90° C. for 16 h. After completion of reaction (by TLC), the reaction mixture was filtered through celite bed and the filtrate was concentrated under reduced pressure to give the crude compound which was purified by column chromatography to provide the Trityl ether 5g (0.3 g, 75%).

TLC: 50% EtOAc/Hexane R$_f$: (0.6)

$^1$H NMR (500 MHz, DMSO-d$_6$, δ in ppm): 8.64 (d, J=9.0 Hz, 1H), 8.51 (s, 1H), 7.95 (d, J=9.5 Hz, 1H), 7.19-7.12 (m, 15H), 4.76-4.74 (m, 1H), 3.22 (dd, J=10.0 Hz, 2.5 Hz, 1H), 3.05 (dd, J=10.0 Hz, 3.0 Hz, 1H), 2.80-2.74 (m, 1H), 2.57-2.53 (m, 1H), 2.36-2.28 (m, 1H), 1.99 (t, J=10.5 Hz, 1H).

5g to 5h

(R)-1-(benzo[d][1,2,3]thiadiazol-6-yl)-5-(hydroxymethyl)pyrrolidin-2-one

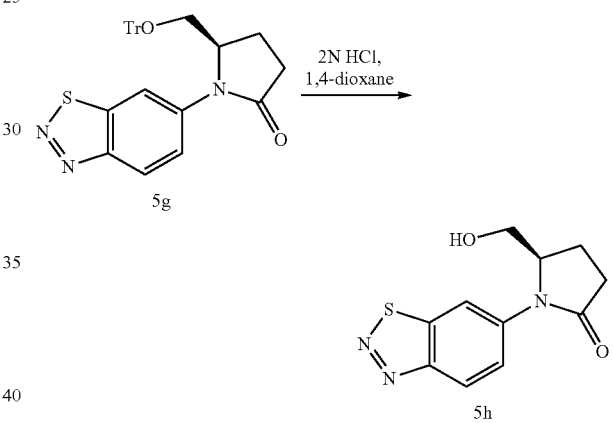

To a solution of (R)-1-(benzo[d][1,2,3]thiadiazol-6-yl)-5-(trityloxymethyl)pyrrolidin-2-one (5g) (0.3 g, 0.61 mmol) in dry THF (10 mL), cooled to 0° C., 2M HCl taken in 1,4-dioxane (1 mL) was added. The resulting reaction mixture was warmed up to room temperature and stirred for 2 h. After completion of reaction (by TLC), the reaction mixture was diluted with water (10 mL), basified with saturated NaHCO$_3$ solution (pH~8-9) and extracted with EtOAc (3×35 mL). The combined organic extracts were dried over Na$_2$SO$_4$ and concentrated under reduced pressure to furnish the alcohol 5h (0.12 g, 80%) which was taken to the next step without purification.

TLC: 60% EtOAc/Hexane R$_f$: (0.2)

$^1$H NMR (500 MHz, DMSO-d$_6$, δ in ppm): 8.68 (d, J=9.0 Hz, 1H), 8.59 (d, J=1.5 Hz, 1H), 8.03 (dd, J=9.0 Hz, 2.0 Hz, 1H), 4.89 (t, J=5.5 Hz, 1H), 4.55-4.54 (m, 1H), 3.57-3.52 (m, 1H), 3.49-3.46 (m, 1H), 2.72-2.65 (m, 1H), 2.47-2.41 (m, 1H), 2.29-2.21 (m, 1H), 2.09-2.04 (m, 1H).

Mass (ESI): 249.9 [M$^+$+1]

5h to Examples 5 and 6

(R)-1-(Benzo[d][1,2,3]thiadiazol-6-yl)-5-((S)-2,2,2-trifluoro-1-hydroxyethyl)pyrrolidin-2-one 5

(R)-1-(Benzo[d][1,2,3]thiadiazol-6-yl)-5-((R)-2,2,2-trifluoro-1-hydroxyethyl)pyrrolidin-2-one 6

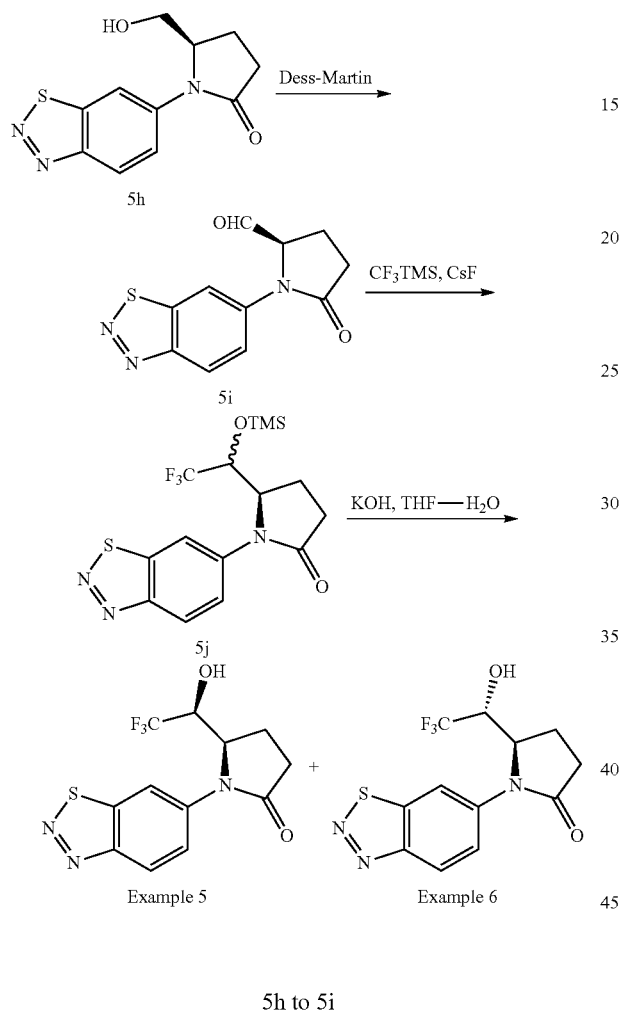

5h to 5i

To a solution of alcohol 5h (0.12 g, 0.48 mmol) in dry CH$_2$Cl$_2$ (10 mL), cooled to 0° C., Dess-Martin periodinane (0.23 g, 0.54 mmol) was added. The resulting reaction mixture was warmed to room temperature and stirred for 4 h. After completion of reaction (by TLC), the reaction mixture was diluted with water (20 mL) and extracted with CH$_2$Cl$_2$ (3×35 mL). The combined organic extracts were dried over Na$_2$SO$_4$ and concentrated under reduced pressure. The crude residue was purified by column chromatography to provide the aldehyde 5i (0.1 g, 83%).

TLC: 50% EtOAc/Hexane R$_f$: (0.6)

5i to 5j

The crude aldehyde 5i (0.15 g, 0.6 mmol) was dissolved in dry THF (10 mL), cooled to 0° C., CsF (90 mg, 0.6 mmol) followed by CF$_3$TMS (0.8 mL, 60.0 mmol) were added. The resulting reaction mixture was warmed to room temperature and stirred for 1 h. After completion of reaction (by TLC), the reaction mixture was quenched with aqueous NH$_4$Cl solution (20 mL) and extracted with EtOAc (3×20 mL). The combined organic extracts were dried over Na$_2$SO$_4$ and concentrated under reduced pressure to provide the silyl ether 5j as a mixture of diastereomers (0.15 g, crude) which was taken to the next step without purification.

TLC: 50% EtOAc/Hexane R$_f$: (0.7 & 0.8)

5j to Examples 5 and 6

The silyl ether 10 (0.15 g, 0.38 mmol) was taken in THF (10 mL), cooled to 0° C., and a solution of KOH (60 mg, 1.1 mmol) in H$_2$O (5 mL) was added and stirred for 2 h. After completion of the reaction (by TLC), the reaction mixture was diluted with H$_2$O (10 mL) and extracted with EtOAc (3×15 mL). The combined organic extracts were dried over Na$_2$SO$_4$ and concentrated under reduced pressure to give the crude compound which was purified by column chromatography to afford Example 5 (0.020 g) and Example 6 (0.011 g) both as white solids.

TLC: 50% EtOAc/Hexane R$_f$: (0.3 (Example 5) & 0.6 (Example 6)).

Example 5

$^1$H NMR (500 MHz, CDCl$_3$, δ in ppm) 5: 8.67 (d, J=9.0 Hz, 1H), 8.53 (d, J=1.5 Hz, 1H), 7.88 (dd, J=9.0 Hz, 2.0 Hz, 1H), 6.66 (d, J=6.5 Hz, 1H), 4.92 (m, 1H), 4.27-4.20 (m, 1H), 2.77-2.68 (m, 1H), 2.46-2.39 (m, 2H), 2.12 (t, J=11.0 Hz, 1H).

Mass (ESI): 318.0 [M$^+$+1]

HPLC purity: 98.58%

Example 6

$^1$H NMR (500 MHz, CDCl$_3$, δ in ppm) 6: 8.75 (d, J=9.0 Hz, 1H), 8.53 (d, J=1.5 Hz, 1H), 7.90 (dd, J=9.0 Hz, 1.5 Hz, 1H), 6.73 (d, J=6.5 Hz, 1H), 4.89-4.87 (dd, J =8.0, 3.5 Hz, 1H), 4.07-4.0 (m, 1H), 2.68-2.61 (m, 1H), 2.47-2.46 (m, 1H), 2.29-2.20 (m, 2H).

Mass (ESI): 318.1 [M$^+$+1]

HPLC purity: 95.39%

Examples 7 and 8

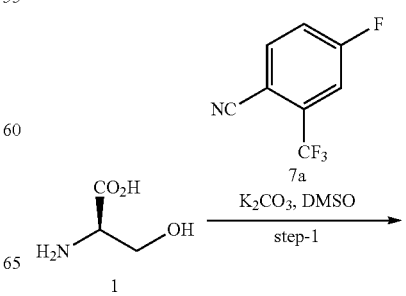

-continued

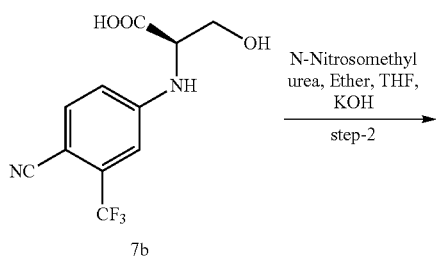
7b

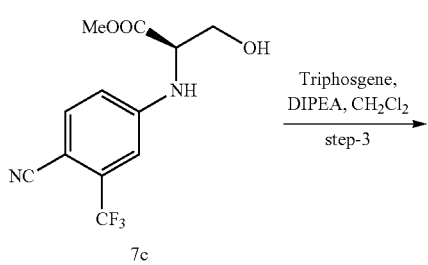
7c

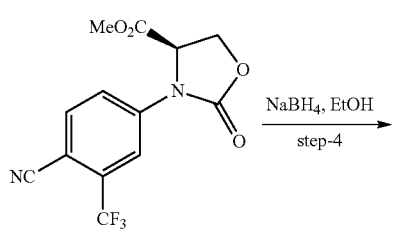

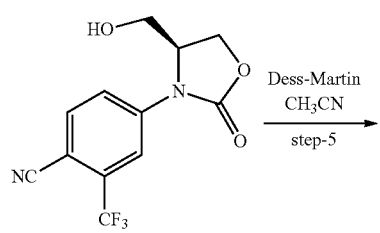
7e

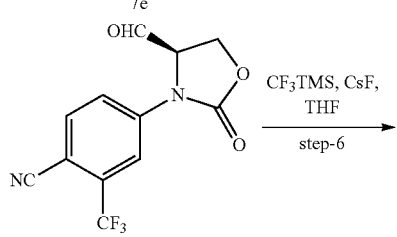
7f

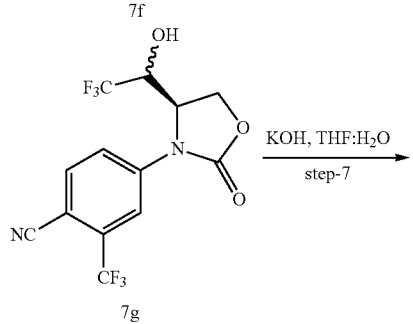
7g

-continued

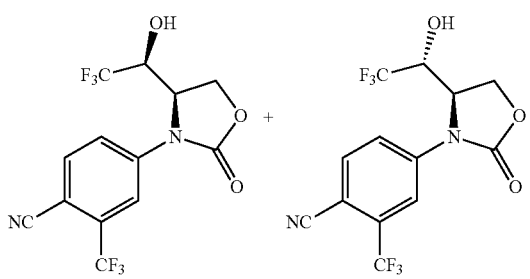

Example 7      Example 8

(R)-2-(4-Cyano-3-(trifluoromethyl)phenyl amino)-3-hydroxypropanoic acid

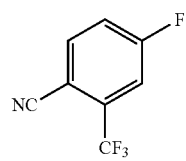
7a

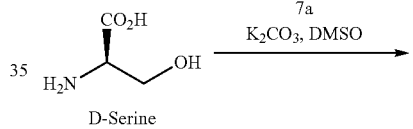

D-Serine

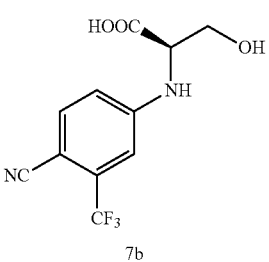
7b

To a solution of D-Serine (1) (3.65 gm, 34.8 mmol) in DMSO (30 mL), $K_2CO_3$ (4.36 gm, 31.6 mmol) followed by 4-Fluoro-2-(trifluoromethyl)benzonitrile (7a) (3.0 gm, 15.8 mmol) was added and the reaction was heated to 80° C. for 4 h. After completion of reaction (by TLC), the reaction mixture was diluted with water (100 mL) and extracted with EtOAc (150 mL). The aqueous layer was acidified with citric acid and extracted with EtOAc (2×100 mL). The combined organic extracts were dried over $Na_2SO_4$ and concentrated under reduced pressure to afford the crude compound which was triturated with Hexane/EtOAc to afford the acid 7b (2.1 gm, 48%) as a crystalline solid.

TLC: 30% MeOH/DCM ($R_f$: 0.3)

$^1$H NMR (500 MHz, DMSO-d$_6$, δ in ppm): 7.72 (d, J=9.0 Hz, 1H), 7.32 (d, J=8.0 Hz, 1H), 7.20 (s, 1H), 6.90 (d, J=8.0 Hz, 1H), 4.28-4.25 (m, 1H), 3.81-3.74 (m, 2H).

7b to 7c (R)-Methyl-2-(4-cyano-3-(trifluoromethyl)phenylamino)-3-hydroxypropanoate

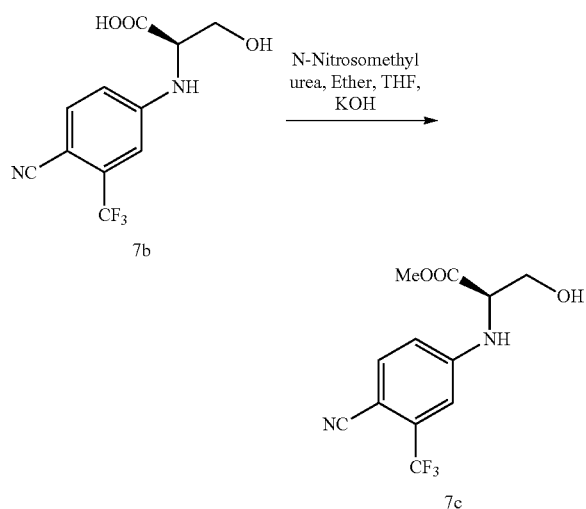

(R)-2-(4-cyano-3-(trifluoromethyl)phenyl amino)-3-hydroxypropanoic acid (7b) (2.1 gm, 7.66 mmol) was dissolved in THF (20 mL), cooled to 0° C., and diazomethane [prepared from N-Nitrosomethyl urea (2.32 gm, 22.9 mmol) and 40% KOH solution (100 mL) in ether (60 mL)] was added to the reaction mixture and stirred for 1 h. After completion of reaction (by TLC), the reaction mixture was poured into water (80 mL) and extracted with EtOAc (2×100 mL). The combined organic extracts were dried over Na$_2$SO$_4$ and concentrated under reduced pressure to give the crude compound which was purified by column chromatography to afford the ester 7c (2.0 gm, 90%).

TLC: 50% EtOAc/Hexane (R$_f$: 0.7)
$^1$H NMR (500 MHz, DMSO-d$_6$, δ in ppm): 7.74 (d, J=8.5 Hz, 1H), 7.41 (d, J=8.5 Hz, 1H), 7.23 (s, 1H), 6.91 (d, J=8.0 Hz, 1H), 5.19 (t, J=5.0 Hz, 1H), 4.43-4.40 (m, 1H), 3.85-3.80 (m, 1H), 3.77-3.73 (m, 1H), 3.67 (s, 3H).

7c to 7d (R)-Methyl-3-(4-cyano-3-(trifluoromethyl)phenyl)-2-oxooxazolidine-4-carboxylate

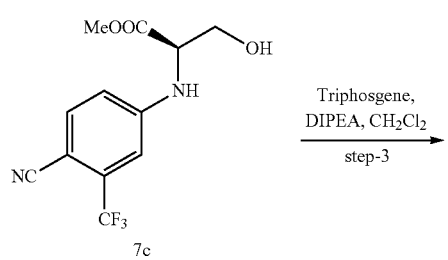

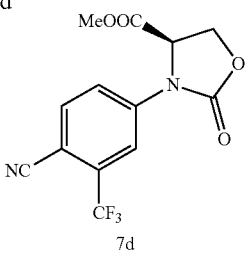

To a stirred solution of (R)-Methyl-2-(4-cyano-3-(trifluoromethyl)phenylamino)-3-hydroxypropanoate (7c) (1.0 g, 3.47 mmol) in dry CH$_2$Cl$_2$ (20 mL), cooled to −78° C., DIPEA (1.71 mL, 10.4 mmol) was added followed by Triphosgene (1.54 gm, 5.2 mmol) in dissolved in CH$_2$Cl$_2$ (10 mL) under nitrogen atmosphere. The resulting reaction mixture was slowly warmed to room temperature and stirred for 16 h. After completion of reaction (by TLC), the reaction mixture was poured into ice-cold water (60 mL) and extracted with CH$_2$Cl$_2$ (2×100 mL). The combined organic extracts were dried over Na$_2$SO$_4$ and concentrated under reduced pressure to give the crude compound which was purified by column chromatography to afford the oxazolidinone 7d (0.091 g, 84%) as syrup.

TLC: 10% MeOH/DCM (R$_f$: 0.6)
$^1$H NMR (500 MHz, DMSO-d$_6$, δ in ppm): 8.31 (d, J=1.5 Hz, 1H), 8.20 (d, J=8.0 Hz, 1H), 7.85 (dd, J=9.0, 2.0 Hz, 1H), 5.60 (dd, J=9.0, 2.5 Hz, 1H), 4.75-4.66 (m, 2H), 3.73 (s, 3H).

7d to 7e (R)-4-(4-(hydroxymethyl)-2-oxooxazolidin-3-yl)-2-(trifluoromethyl)benzonitrile

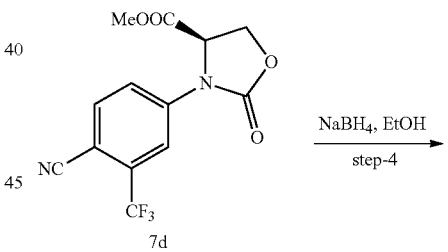

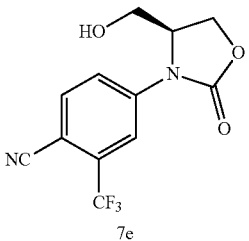

To a stirred solution of (R)-Methyl-3-(4-cyano-3-(trifluoromethyl)phenyl)-2-oxooxazolidine-4-carboxylate (7d) (1.3 gm, 4.14 mmol) in EtOH (50 mL), NaBH$_4$ (172 mg, 4.55 mmol) was added at 0° C. under nitrogen atmosphere. The resulting reaction mixture was warmed to room temperature and stirred for 1 h. After completion of reaction (by TLC), the volatiles were evaporated under reduced pressure and the residue was diluted with saturated NH$_4$Cl solution (100 mL) and extracted with EtOAc (2×100 mL). The combined organic extracts were dried over Na$_2$SO$_4$ and concentrated under reduced pressure to give the crude compound, The crude material was purified by column chromatography to afford the alcohol 7e (0.65 g, 55%) as a white solid.

TLC: 50% EtOAc/Hexane (R$_f$: 0.2)

$^1$H NMR (500 MHz, DMSO-d$_6$, δ in ppm): 8.38 (d, J=1.5 Hz, 1H), 8.18 (d, J=9.0 Hz, 1H), 7.97 (dd, J=9.0, 2.0 Hz, 1H), 5.14 (t, J=5.5 Hz, 1H), 4.87-4.84 (m, 1H), 4.53 (t, J=9.0 Hz, 1H), 4.38-4.35 (m, 1H), 3.67-3.63 (m, 1H), 3.51-3.47 (m, 1H).

7e to Examples 7 and 8

4-((R)-2-oxo-4-((S)-2,2,2-trifluoro-1-hydroxyethyl)oxazolidin-3-yl)-2-(trifluoromethyl)benzonitrile 7 &

4-((R)-2-oxo-4-((R)-2,2,2-trifluoro-1-hydroxyethyl)oxazolidin-3-yl)-2-(trifluoromethyl)benzonitrile 8

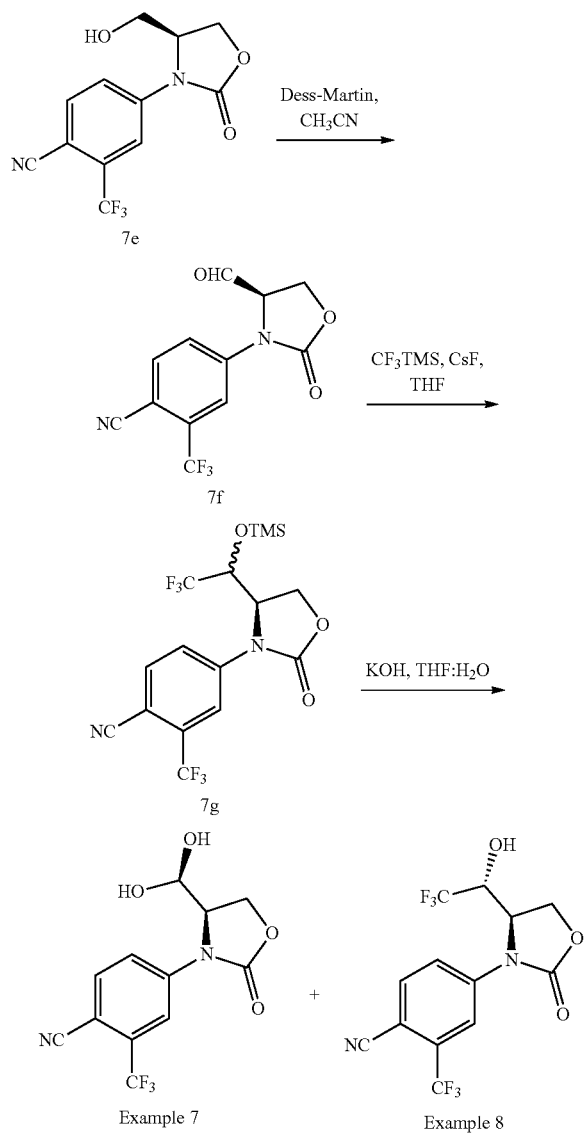

7e to 7f

To a solution of (S)-4-(4-(hydroxymethyl)-2-oxooxazolidin-3-yl)-2-(trifluoromethyl)benzonitrile (7e) (0.4 g, 1.4 mmol) in CH$_3$CN (30 mL) Dess-Martin periodinane (1.19 g, 2.8 mmol) was added at 0° C. under nitrogen atmosphere. The resulting reaction mixture was stirred for 10 h at 0° C. After completion of reaction (by TLC), saturated NaHCO$_3$ solution (40 mL) was added to the reaction mixture and extracted with EtOAc (2×50 mL). The combined organic extracts were dried over Na$_2$SO$_4$, filtered and concentrated under reduced pressure to afford the aldehyde 7f (0.3 g, crude). The crude material was taken for the next step without any purification.

TLC: 10% MeOH/DCM (R$_f$: 0.6)

7f to 7g

The crude aldehyde 7f (0.3 gm, 1.05 mmol) was dissolved in THF (10 mL), CsF (0.16 g, 1.05 mmol) was added followed by CF$_3$TMS (1.5 g, 10.5 mmol) at 0° C. under nitrogen atmosphere. The resulting reaction mixture was stirred for 3 h at 0° C. After completion of reaction (by TLC), the reaction mixture was quenched with 0.1N NH$_4$Cl solution (30 mL) and extracted with EtOAc (2×80 mL). The combined organic extracts were dried over Na$_2$SO$_4$ and concentrated under reduced pressure to afford the silyl ether 7g as a mixture of diastereomers (0.3 g, crude). The crude residue was taken for the next step without further purification.

TLC: 50% EtOAc/Hexane (R$_f$: 0.6).

7g to Examples 7 and 8

To a stirred solution of the crude silyl ether 7g (0.3 gm, 0.7 mmol) in THF (10 mL), KOH (118 mg, 2.11 mmol) dissolved in water (5 mL) was added at 0° C. and stirred for 30 min. The reaction mixture was diluted with water (30 mL) and extracted with EtOAc (2×60 mL). The combined organic extracts were dried over Na$_2$SO$_4$ and concentrated under reduced pressure to give the crude residue. The crude product was purified by column chromatography to afford 7 (18.7 mg) and 8 (10.0 mg) both as white solids.

TLC: 50% EtOAc/Hexane (R$_f$: 0.3 (7) & 0.7 (8))

Example 7

$^1$H NMR (500 MHz, DMSO-d$_6$, δ in ppm): 8.20 (d, J=8.5 Hz, 2H), 8.02 (t, J=8.5 Hz, 1H), 6.98 (d, J=7.0 Hz, 1H), 5.24 (t, J=5.5 Hz, 1H), 4.59 (t, J=8.5 Hz, 1H), 4.46-4.42 (m, 2H).

Mass (ESI) 353.2 [M$^-$−1]

HPLC purity: 97.56%

Example 8

$^1$H NMR (500 MHz, DMSO-d$_6$, δ in ppm): 8.25 (d, J=6.0 Hz, 2H), 7.90 (d, J=9.0 Hz, 1H), 7.08 (d, J=6.5 Hz, 1H), 5.26 (t, J=6.0 Hz, 1H), 4.56 (d, J=6.5 Hz, 2H), 4.30 (t, J=7.5 Hz, 1H).

Mass (ESI): 353.6[M$^-$−1]

HPLC purity: 98.06%

Examples 9 and 10
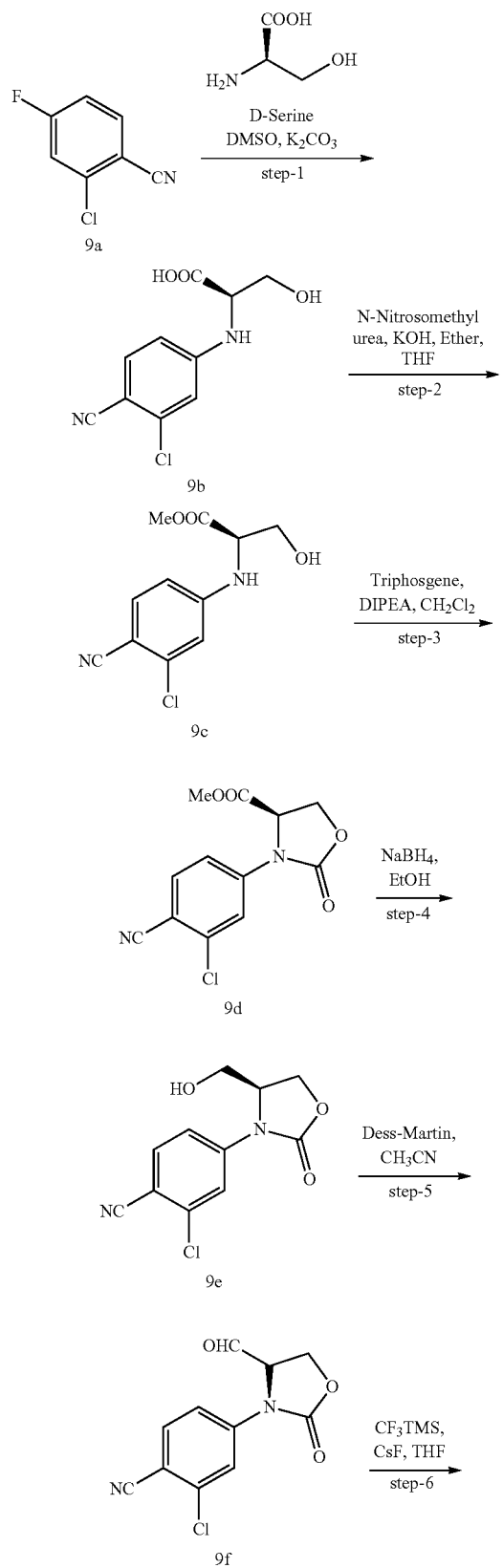
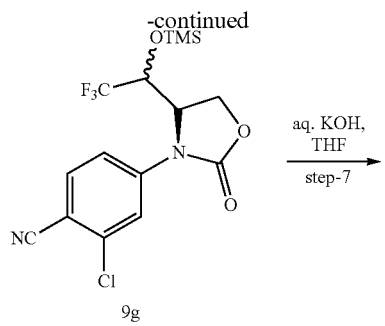
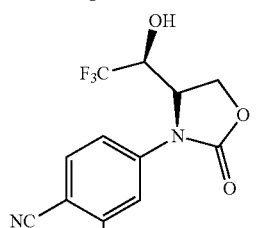
9a to 9b
(R)-2-(3-chloro-4-cyanophenylamino)-3-hydroxypropanoic acid
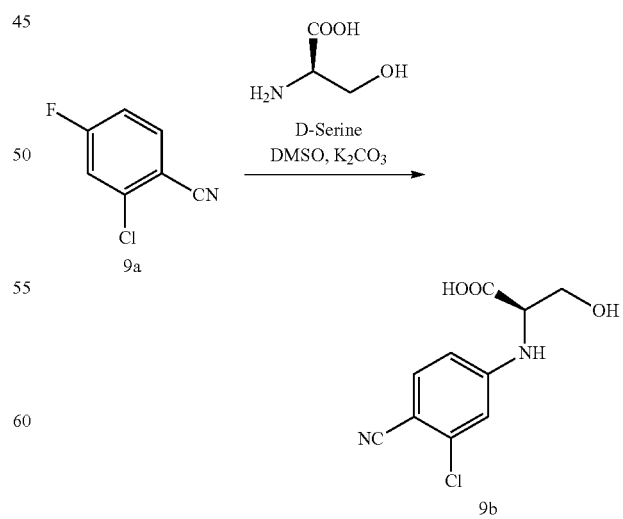
To a stirred solution of D-Serine (2.98 gm, 28.4 mmol) in DMSO (30 mL), K$_2$CO$_3$ (3.5 gm, 25.3 mmol) followed by 2-chloro-4-fluorobenzonitrile (9a) (2.0 gm, 12.8 mmol) was added at room temperature under nitrogen atmosphere. The resulting reaction mixture was heated to 80° C. and stirred for 12 h. After completion of reaction (by TLC), the reaction mixture was diluted with water (50 mL) and extracted with EtOAc (20 mL). The aqueous layer was acidified with citric acid and extracted with EtOAc (3×30 mL). The combined organic extracts were washed with water (2×30 mL) dried over $Na_2SO_4$ and concentrated under reduced pressure to afford the acid 9b (1.7 gm, crude) as a white solid which was taken for the next step without purification.

TLC: 10% MeOH/DCM ($R_f$: 0.4)

$^1$H NMR (200 MHz, DMSO-$d_6$, δ in ppm): 7.54 (d, J=8.4 Hz, 1H), 7.09 (d, J=8.4 Hz, 1H), 6.86 (d, J=1.8 Hz, 1H), 6.69 (dd, J=8.8, 2.2 Hz, 1H), 4.21-4.12 (m, 1H), 3.74 (dd, J=4.6, 2.6 Hz, 2H).

9b to 9c (R)-methyl 2-(3-chloro-4-cyanophenylamino)-3-hydroxypropanoate

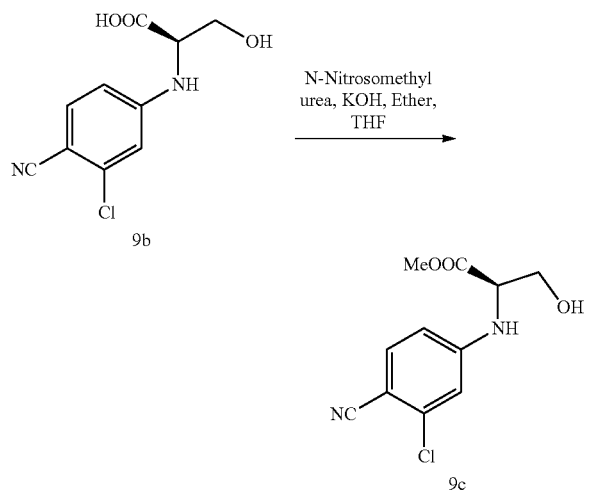

(R)-2-(3-chloro-4-cyanophenylamino)-3-hydroxypropanoic acid (9b) (3.1 gm, 12.9 mmol) was dissolved in THF (30 mL) and Diazomethane [prepared by N-Nitrosomethyl urea (6.5 gm, 64.3 mmol) and 40% KOH solution (40 mL) in ether (30 mL)] was added at 0° C. under nitrogen atmosphere. The resulting reaction mixture was stirred for 3 h at 0° C. After completion of the reaction (by TLC), the reaction mixture was diluted with water (30 mL) and extracted with EtOAc (2×50 mL). The combined organic extracts were washed with water (2×25 mL), dried over $Na_2SO_4$ and concentrated under reduced pressure to give the crude residue which was purified by column chromatography to afford the ester 9c (3.0 gm, 93%) as a white solid.

TLC: 50% EtOAc/Hexane ($R_f$: 0.6)

$^1$H NMR (200 MHz, DMSO-$d_6$, δ in ppm): 7.55 (d, J=8.8 Hz, 1H), 7.18 (d, J=8.6 Hz, 1H), 6.89 (d, J=2.2 Hz, 1H), 6.70 (dd, J=8.6, 2.0 Hz, 1H), 5.18 (t, J=5.4 Hz, 1H), 4.38-4.23 (m, 1H), 3.84-3.72 (m, 2H), 3.66 (s, 3H).

Mass (ESI): 255 [M$^+$+1]

9c to 9d (R)-methyl 3-(3-chloro-4-cyanophenyl)-2-oxooxazolidine-4-carboxylate

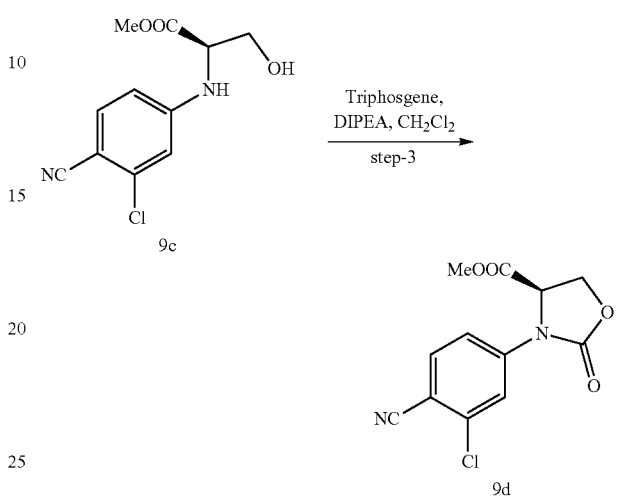

To a stirred solution of (R)-methyl 2-(3-chloro-4-cyanophenylamino)-3-hydroxypropanoate (9c) (1.0 gm, 4.44 mmol) in dry $CH_2Cl_2$ (25 mL), cooled to −78° C., DIPEA (2.1 mL, 13.2 mmol) followed by Triphosgene (1.9 gm, 6.4 mmol) in $CH_2Cl_2$ (10 mL) was added under nitrogen atmosphere. The resulting reaction mixture was slowly warmed to room temperature and stirred for 12 h. After completion of reaction (by TLC), the reaction mixture was diluted with water (20 mL) and extracted with $CH_2Cl_2$ (20 mL). The organic extract was washed with saturated brine solution (2×15 mL), separated, dried over $Na_2SO_4$ and concentrated under reduced pressure to provide the crude compound. The crude material was purified by column chromatography to afford the oxazolidinone 9d (0.95 gm, 79%) as a white solid.

TLC: 50% EtOAc/Hexane ($R_f$: 0.7)

$^1$H NMR (200 MHz, DMSO-$d_6$, δ in ppm): 8.02-7.98 (m, 2H), 7.62 (dd, J=8.8, 2.2 Hz, 1H), 5.52 (dd, J=8.8, 3.4 Hz, 1H), 4.75-4.56 (m, 2H), 3.73 (s, 3H).

9d to 9e (S)-2-chloro-4-(4-(hydroxymethyl)-2-oxooxazolidin-3-yl)benzonitrile

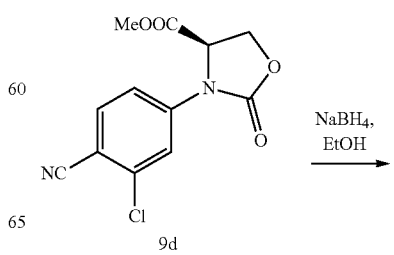

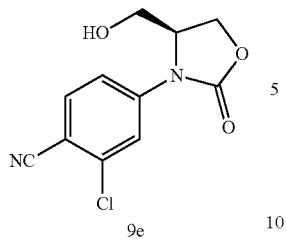

To a stirred solution of (R)-Methyl-3-(3-chloro-4-cyanophenyl)-2-oxooxazolidine-4-carboxylate (9d) (0.6 gm, 2.14 mmol) in EtOH (15 mL), cooled to 0° C., NaBH$_4$ (84 mg, 2.22 mmol) was added under nitrogen atmosphere. The resulting reaction mixture was brought to room temperature and stirred for additional 4 h. After completion of reaction (by TLC), the volatiles were evaporated under reduced pressure and the residue was diluted with aqueous NH$_4$Cl (10 mL) and extracted with EtOAc (2×20 mL). The combined organic extracts were washed with water (2×20 mL), separated, dried over Na$_2$SO$_4$ and concentrated under reduced pressure to give the crude compound. The crude residue was triturated with hexane to provide the alcohol 9e (0.2 gm, 37%) as a white solid.

TLC: 40% EtOAc/Hexane (R$_f$: 0.3)

$^1$H NMR (500 MHz, DMSO-d$_6$, δ in ppm): 8.05 (s, 1H), 7.98 (d, J=8.5 Hz, 1H), 7.75 (d, J=8.5 Hz, 1H), 5.13 (t, J=5.5 Hz, 1H), 4.78-4.76 (m, 1H), 4.50 (t, J=8.5 Hz, 1H), 4.35 (dd, J=8.5, 3.0 Hz, 1H), 3.65-3.61 (m, 1H), 3.48-3.45 (m, 1H).

9e to Examples 9 and 10

2-chloro-4-((S)-2-oxo-4-((S)-2,2,2-trifluoro-1-hydroxyethyl)oxazolidin-3-yl)benzonitrile 9 &

2-chloro-4-((S)-2-oxo-4-((R)-2,2,2-trifluoro-1-hydroxyethyl)oxazolidin-3-yl)

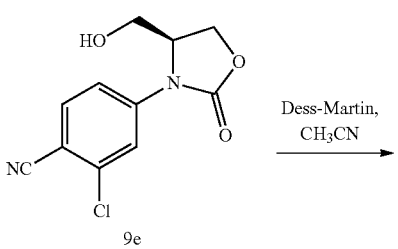

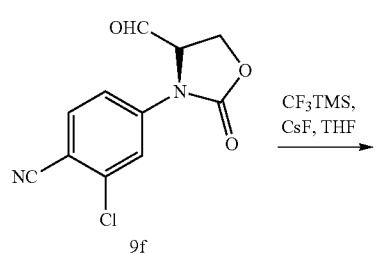

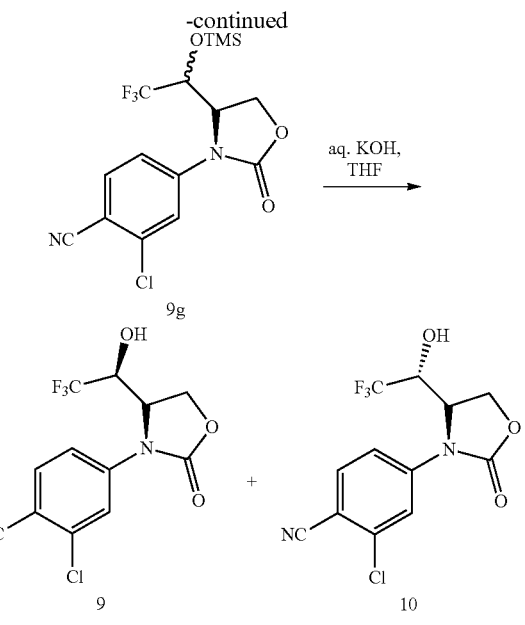

9e to 9f

To a stirred solution of (S)-2-Chloro-4-(4-(hydroxymethyl)-2-oxooxazolidin-3-yl)benzonitrile (9e) (0.5 gm, 1.78 mmol) in CH$_3$CN (20 mL) Dess-Martin periodinane (1.1 gm, 2.6 mmol), was added at 0° C. under nitrogen atmosphere. The resulting reaction mixture was brought to room temperature and stirred for 2 h. After completion of reaction (by TLC), saturated NaHCO$_3$ solution (40 mL) was added to the reaction mixture and extracted with EtOAc (2×20 mL). The combined organic extracts were washed with water (2×20 mL), separated, dried over Na$_2$SO$_4$, filtered and concentrated under reduced pressure to afford the aldehyde 9f (0.35 gm, crude). The crude material was taken for the next step without any purification.

TLC: 10% MeOH/DCM (R$_f$: 0.7)

9f to 9g

The crude aldehyde 9f (0.3 gm, 1.01 mmol) was dissolved in THF (10 mL), cooled to 0° C., and CsF (0.15 gm, 1.0 mmol) followed by CF$_3$TMS (1.4 gm, 9.8 mmol) was added. The reaction mixture was stirred at 0° C. for 1 h. After completion of reaction (by TLC), the reaction mixture was quenched with saturated NH$_4$Cl solution (20 mL) and extracted with EtOAc (2×20 mL). The combined organic extracts were washed with water (2×20 mL). The organic layer was separated, dried over Na$_2$SO$_4$ and concentrated under reduced pressure to afford the silyl ether 9g as a mixture of diastereomers (0.2 gm, crude) which was used for the next step without purification.

TLC: 50% EtOAc/Hexane (R$_f$: 0.8 & 0.9)

9g to Example 9 and 10

To a stirred solution of the silyl ether 9g (0.2 gm, 0.5 mmol) in THF (5 mL), KOH (85 mg, 1.5 mmol) taken in water (5 mL) was added at 0° C. The resulting reaction mixture was stirred at 0° C. for 1 h. After completion of reaction (by TLC), the reaction mixture was diluted with water (5 mL) and extracted with EtOAc (2×10 mL). The combined organic extracts were washed with water (2×10 mL) and the organic layer was separated, dried over Na₂SO₄ and concentrated under reduced pressure to provide the crude mixture. The crude residue was purified by column chromatography during which 9 and 10 were separated but were still contaminated with impurities. Impure 9 was purified by preparative HPLC to afford 0.016 g of pure compound as a white solid. On the other hand, impure 10 was further purified by column chromatography and triturated with n-pentane to provide 0.020 g of pure compound as a white solid.

TLC: 60% EtOAc/Hexane ($R_f$: 0.3 9 & 0.5 10)

Example 9

¹H NMR (500 MHz, DMSO-$d_6$, δ in ppm): 8.00 (d, J=9.0 Hz, 1H), 7.96 (s, 1H), 7.72 (d, J=8.5 Hz, 1H), 6.96 (d, J=7.0 Hz, 1H), 5.15 (br s, 1H), 4.56 (t, J=8.5 Hz, 1H), 4.46-4.40 (m, 2H).

Mass (ESI) 320.1 [M⁺]
HPLC purity: 95.7%

Example 10

¹H NMR (500 MHz, DMSO-$d_6$, δ in ppm): 8.06 (d, J=9.0 Hz, 1H), 7.98 (s, 1H), 7.61 (dd, J=8.5, 2.0 Hz, 1H), 7.10 (d, J=7.0 Hz, 1H), 5.18 (t, J=6.0 Hz, 1H), 4.56-4.52 (m, 2H), 4.25 (t, J=7.5 Hz, 1H).

Mass (ESI): 319.8 [M⁻−1]
HPLC purity: 98.0%

Examples 11 and 12

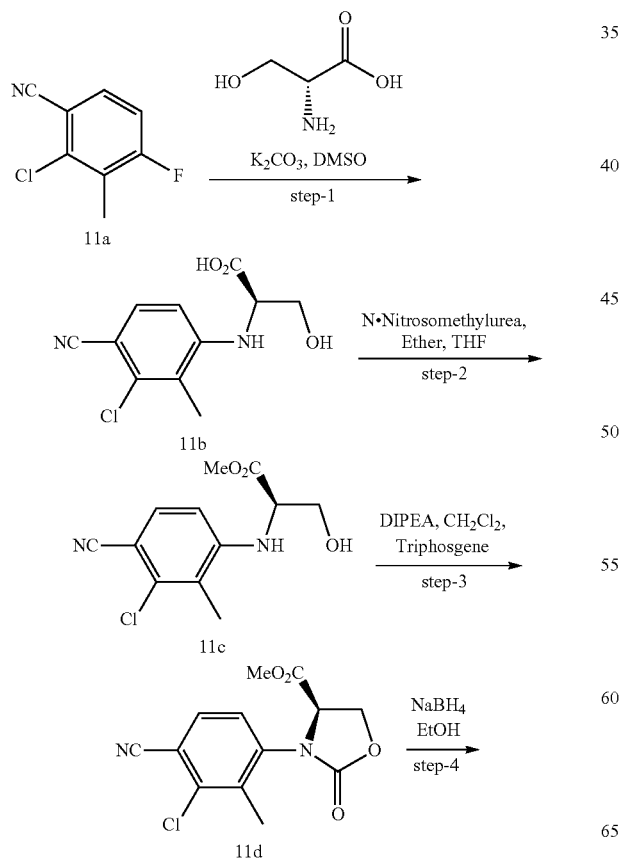

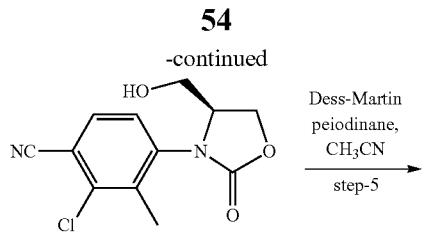

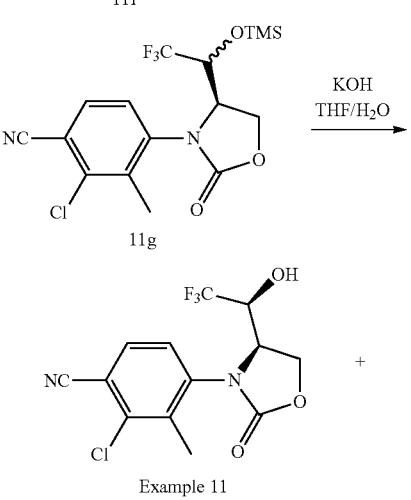

11a to 11b (R)-2-(3-chloro-4-cyano-2-methylphenylamino)-3-hydroxypropanoic acid

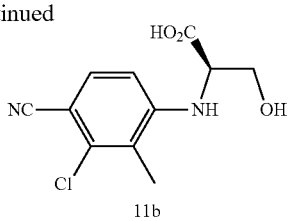

To a stirred solution of 2-chloro-4-fluoro-3-methylbenzonitrile (11a) (1.0 gm, 5.8 mmol) in DMSO (10 mL), D-Serine (1.4 gm, 13.3 mmol) was added followed by $K_2CO_3$ (1.7 gm, 12.3 mmol) at room temperature. The resulting reaction mixture was heated to 90° C. for 12 h. After completion of reaction (by TLC), the reaction mixture was poured into ice-cold water (300 mL) and extracted with EtOAc (100 mL). The aqueous layer was acidified with citric acid (pH~3) and extracted with EtOAc (2×100 mL). The combined organic extracts were dried over $Na_2SO_4$, and concentrated under reduced pressure to afford the acid 11b (0.3 gm, crude) as off-white solid. The crude material was taken for the next step without purification.

TLC: 10% MeOH/DCM ($R_f$: 0.2)

$^1$H NMR (500 MHz, DMSO-$d_6$, δ in ppm): 8.2-10.2 (br s, 1H), 7.54 (d, J=8.5 Hz, 1H), 6.57 (d, J=9.0 Hz, 1H), 5.79 (d, J=7.5 Hz, 1H), 4.20 (t, J=3.0 Hz, 1H), 3.86-3.79 (m, 2H), 3.22 (br s, 1H), 2.25 (s, 3H).

11b to 11c (R)-Methyl 2-(3-chloro-4-cyano-2-methylphenylamino)-3-hydroxypropanoate

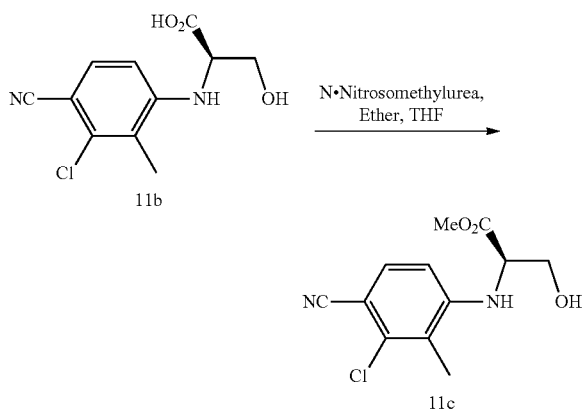

To a solution of (R)-2-(3-chloro-4-cyano-2-methylphenylamino)-3-hydroxy propanoic acid (11b) (0.3 g, 1.1 mmol) in THF (20 mL), diazomethane [prepared by N-Nitrosomethyl urea (0.35 g, 3.4 mmol) and 40% KOH solution (20 mL) in ether (30 mL)] was added at 0° C. and the resulting reaction mixture was stirred at 0° C. for 3 h. After completion of reaction (by TLC), the reaction mixture was diluted with water (30 mL) and extracted with EtOAc (2×50 mL). The combined organic extracts were dried over $Na_2SO_4$ and concentrated under reduced pressure to give the crude compound which was purified by column chromatography to afford the ester 11c (0.25 g, 80%) as a white solid.

TLC: 50% EtOAc/Hexane ($R_f$: 0.6)

$^1$H NMR (500 MHz, DMSO-$d_6$, δ in ppm): 7.54 (d, J=9.0 Hz, 1H), 6.57 (d, J=9.0 Hz, 1H), 5.83 (d, J=8.5 Hz, 1H), 5.24 (t, J=6.0 Hz, 1H), 4.39-4.37 (m, 1H), 3.88-3.84 (m, 2H), 3.66 (s, 3H), 2.26 (s, 3H).

11c to 11d (R)-Methyl 3-(3-chloro-4-cyano-2-methylphenyl)-2-oxooxazolidine-4-carboxylate

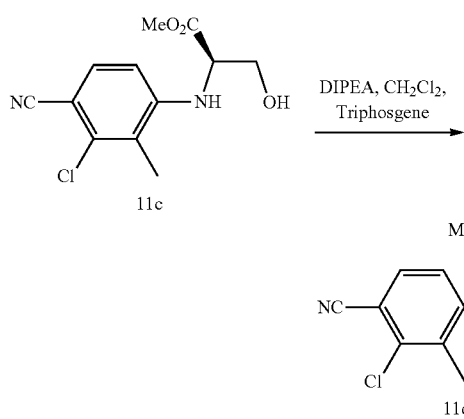

To a solution of (R)-Methyl 2-(3-chloro-4-cyano-2-methyl phenyl amino)-3-hydroxypropanoate (11c) (250 mg, 0.92 mmol) in dry $CH_2Cl_2$ (10 mL), cooled to −78° C., DIPEA (0.5 mL, 3.0 mmol) followed by Triphosgene (0.4 g, 1.3 mmol) in $CH_2Cl_2$ (5 mL) was added under nitrogen atmosphere. The resulting reaction mixture was slowly brought to room temperature and stirred for 12 h. After completion of reaction (by TLC), the reaction mixture was diluted with water (30 mL) and extracted with $CH_2Cl_2$ (2×50 mL). The combined organic extracts were dried over $Na_2SO_4$, filtered and concentrated under reduced pressure to give the crude compound. The crude material was purified by column chromatography to afford oxazolidinone 11d (0.150 g, 55%).

TLC: 10% MeOH/DCM ($R_f$: 0.5)

$^1$H NMR (500 MHz, DMSO-$d_6$, δ in ppm): 7.92 (d, J=8.5 Hz, 1H), 7.64 (d, J=8.5 Hz, 1H), 5.31-5.28 (m, 1H), 4.82 (t, J=9.0 Hz, 1H), 4.60-4.58 (m, 1H), 3.63 (s, 3H), 2.34 (s, 3H).

11d to 11e (S)-2-chloro-4-(4-(hydroxymethyl)-2-oxo oxazolidin-3-yl)-3-methylbenzonitrile

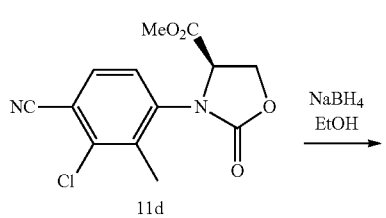

-continued

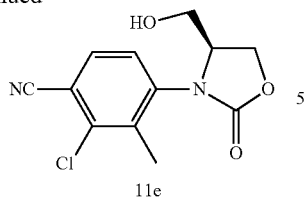
11e

To a stirred solution of (R)-Methyl 3-(3-chloro-4-cyano-2-methylphenyl)-2-oxo oxazolidine-4-carboxylate (11d) (0.15 g, 0.5 mmol) in EtOH (20 mL), cooled to 0° C., NaBH$_4$ (21 mg, 0.56 mmol) was added. The resulting reaction mixture was allowed to warm up to room temperature and stirred for further 4 h. After completion of reaction (by TLC), the volatiles were evaporated under reduced pressure and the residue was diluted with water (40 mL) and extracted with EtOAc (2×50 mL). The combined organic extracts were dried over Na$_2$SO$_4$, filtered and concentrated under reduced pressure to give the crude compound which was purified by column chromatography to provide the alcohol 11e (0.085 g, 65%).

TLC: 10% MeOH/DCM (R$_f$: 0.3)

$^1$H NMR (500 MHz, DMSO-d$_6$, δ in ppm): 7.92 (d, J=8.5 Hz, 1H), 7.59 (d, J=8.5 Hz, 1H), 5.08 (t, J=5.0 Hz, 1H), 4.60 (t, J=9.0 Hz, 1H), 4.46 (bs, 1H), 4.34-4.32 (m, 1H), 3.42-3.38 (m, 1H), 3.34-3.31 (m, 1H), 2.31 (s, 3H).

11e to Example 11 and 12

2-chloro-3-methyl-4-((R)-2-oxo-4-((S)-2,2,2-trifluoro-1-hydroxy ethyl)oxazolidin-3-yl)benzonitrile
11

2-chloro-3-methyl-4-((R)-2-oxo-4-((R)-2,2,2-trifluoro-1-hydroxy ethyl)oxazolidin-3-yl)benzonitrile
12

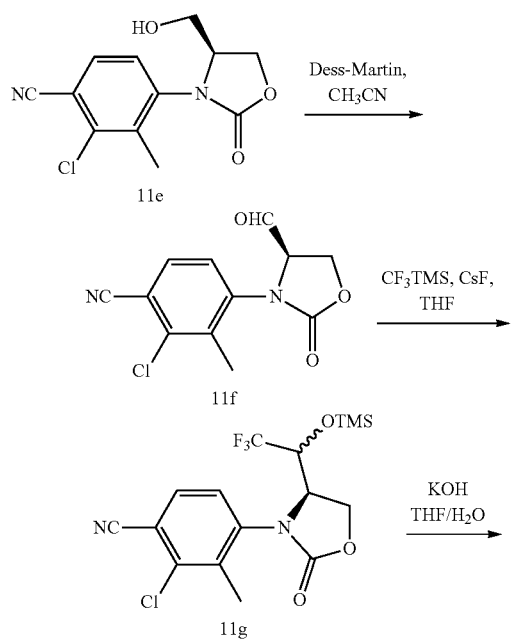

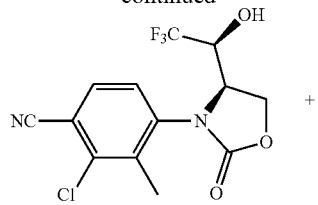
Example 11

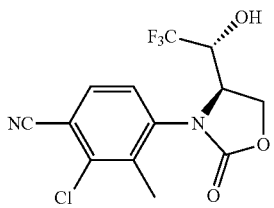
Example 12

11e to 11f

To a stirred solution of (S)-2-chloro-4-(4-(hydroxymethyl)-2-oxo oxazolidin-3-yl)-3-methylbenzonitrile (11e) (0.8 g, 3.0 mmol) in CH$_3$CN (100 mL), cooled to 0° C., Dess-Martin periodinane (2.5 gm, 6.0 mmol) was added and the resulting reaction mixture was slowly brought to room temperature and stirred for additional 2 h. After completion of reaction (by TLC), saturated NaHCO$_3$ solution (80 mL) was added to the reaction mixture and extracted with EtOAc (2×100 mL). The combined organic extracts were dried over Na$_2$SO$_4$ and concentrated under reduced pressure to afford the aldehyde 11f (0.45 g, crude) as a solid which was taken for the next step without purification.

TLC: 10% MeOH/DCM (R$_f$: 0.6)

11f to 11g

To a solution of the aldehyde 11f (0.45 gm, 1.5 mmol) in THF (10 mL), cooled to 0° C., CsF (0.22 g, 1.5 mmol) was added followed by CF$_3$TMS (0.22 g, 1.5 mmol) and stirred for 2 h at 0° C. After completion of reaction (by TLC), the reaction mixture was quenched with saturated NH$_4$Cl solution (40 mL) and extracted with EtOAc (2×100 mL). The combined organic extracts were dried over Na$_2$SO$_4$ and concentrated under vacuo to afford the silyl ether 11g as a mixture of diastereomers (0.5 g, crude). The crude material was carried forward without purification.

TLC: 50% EtOAc/Hexane (R$_f$: 0.8 & 0.9)

11g to Example 11 and 12

The crude silyl ether 1g (0.5 g, 1.2 mmol) was dissolved in THF (20 mL), cooled to 0° C., KOH (0.2 g, 3.6 mmol) taken in water (20 mL) was added. The resulting reaction mixture was stirred at 0° C. for 2 h. After completion of reaction (by TLC), the reaction mixture was diluted with water (50 mL) and extracted with EtOAc (2×100 mL). The combined organic extracts were dried over Na$_2$SO$_4$ and concentrated under reduced pressure to give the crude mixture which was purified by column chromatography followed by preparative HPLC to afford 11 (0.040 g) and 12 (0.130 g) both as off-white solids.

TLC: 50% EtOAc/Hexane (R$_f$: 0.3 11 & 0.6 12)

Example 11
$^1$H NMR (500 MHz, DMSO-$d_6$, δ in ppm): 7.88 (d, J=8.0 Hz, 1H), 7.68 (d, J=8.5 Hz, 1H), 6.86 (d, J=7.0 Hz, 1H), 4.82 (br s, 1H), 4.69 (t, J=9.0 Hz, 1H), 4.37-4.32 (m, 2H), 2.33 (s, 3H).
HPLC purity: 95.82%
Example 12
$^1$H NMR (500 MHz, DMSO-$d_6$, δ in ppm): 7.97 (d, J=8.5 Hz, 1H), 7.66 (br s, 1H), 7.10 (br s, 1H), 4.85 (br s, 1H), 4.61 (t, J=8.5 Hz, 1H), 4.53 (t, J=7.0 Hz, 1H), 3.99-3.95 (m, 1H), 2.31 (s, 3H).
HPLC purity: 98
Example 13 and 14
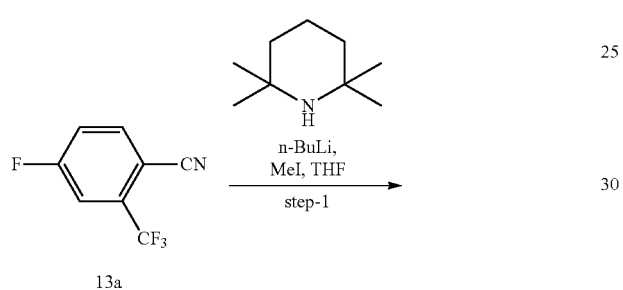
13a
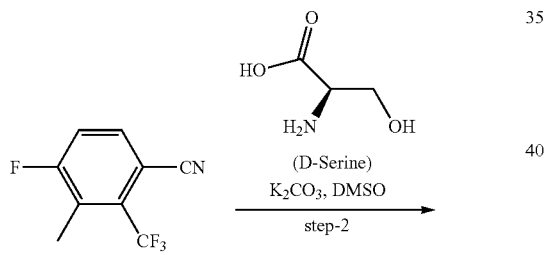
13b
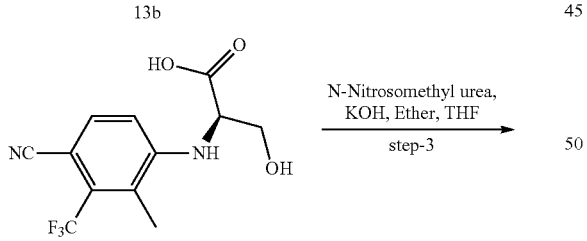
13c
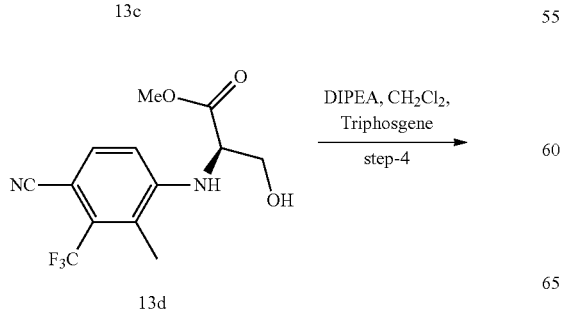
13d
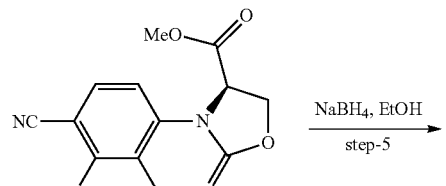
13e
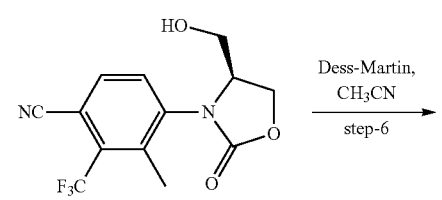
13f
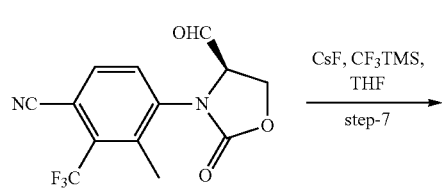
13g
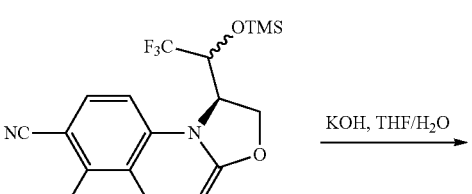
13h
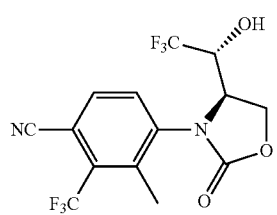
Example 13
Example 14

13a to 13b

4-Fluoro-3-methyl-2-(trifluoromethyl)benzo nitrile

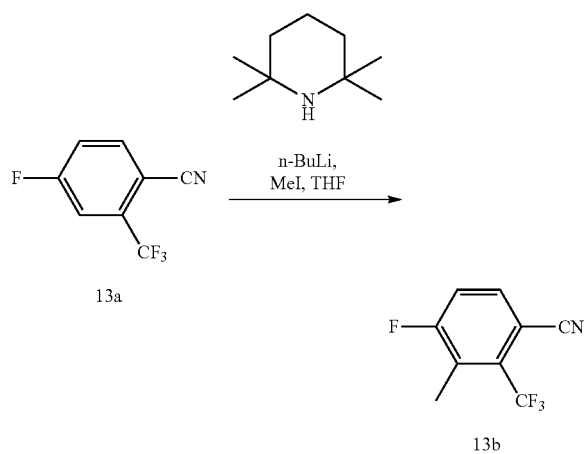

To a solution of 2,2,6,6-tetramethylpiperidine (1.4 mL, 8.2 mmol) in dry THF (4 mL), cooled to −78° C., n-BuLi (2.9 mL, 2.5M solution in hexane, 8.2 mmol) was added drop wise under nitrogen atmosphere. After being stirred for 30 min at −78° C., the resulting solution was brought to −20° C. and stirred for additional 30 min. 4-fluoro-2-(trifluoromethyl) benzonitrile (13a) (1.0 g, 5.2 mmol) was dissolved in dry THF (8 mL), cooled to −78° C., and the above prepared lithiated piperidine solution was added under nitrogen atmosphere. After 5 h, MeI (0.6 mL, 9.3 mmol) was added to the reaction mixture maintaining the temperature at −78° C. The resulting reaction mixture was slowly brought to room temperature and stirred for 16 h. After completion of reaction (by TLC), aqueous NH$_4$Cl (20 mL) was added to the reaction mixture and extracted with EtOAc (2×20 mL). The combined organic extracts were dried over Na$_2$SO$_4$ and concentrated under reduced pressure to give the crude compound. The crude material was purified by column chromatography to afford the nitrile 13b (0.25 g, 25%) as a yellow oil.

TLC: 7% EtOAc/Hexane (R$_f$: 0.5)

$^1$H NMR (500 MHz, CDCl$_3$, δ in ppm): 7.69 (dd, J=8.0 Hz, 5.5 Hz, 1H), 7.34 (d, J=8.5 Hz, 1H), 2.45 (s, 3H).

13b to 13c (R)-2-((4-cyano-2-methyl-3-(trifluoromethyl)phenyl) amino)-3-hydroxypropanoic acid

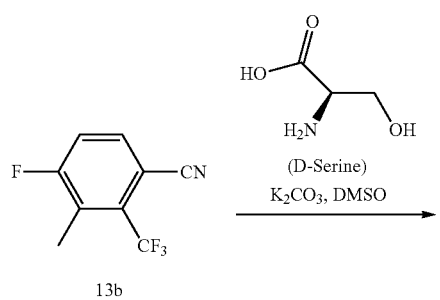

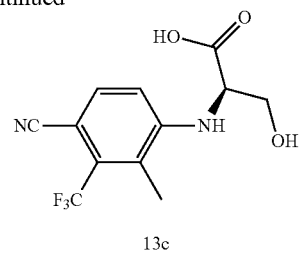

To a solution of D-Serine (0.85 g, 4.2 mmol) in DMSO (20 mL), at room temperature, K$_2$CO$_3$ (1.13 g, 8.3 mmol) was added followed by 4-fluoro-3-methyl-2-(trifluoromethyl) benzo nitrile (13b) (0.88 g, 8.3 mmol). The resulting reaction mixture was then heated to 80° C. for 16 h, diluted with water (20 mL) and acidified to pH~3 using citric acid. The aqueous layer was extracted with EtOAc (3×20 mL). The combined organic extracts were dried over Na$_2$SO$_4$ and concentrated under reduced pressure to give the crude compound which was triturated with 10% EtOAc/hexane to afford the acid 13c (0.65 g, 54%) as an off-white solid.

TLC: 30% EtOAc/Hexane (R$_f$: 0.3)

$^1$H NMR (500 MHz, DMSO-d$_6$, δ in ppm): 8.30-9.50 (br s, 1H), 7.66 (d, J=9.0 Hz, 1H), 6.87 (d, J=9.0 Hz, 1H), 5.92 (d, J=7.5 Hz, 1H), 4.28-4.26 (m, 1H), 3.89-3.84 (m, 2H), 3.30-3.50 (br s, 1H), 2.26 (s, 3H).

Mass (ESI): 286.9 [M$^+$−1]

13c to 13d (R)-methyl 2-((4-cyano-2-methyl-3-(trifluoromethyl) phenyl)amino)-3-hydroxypropanoate

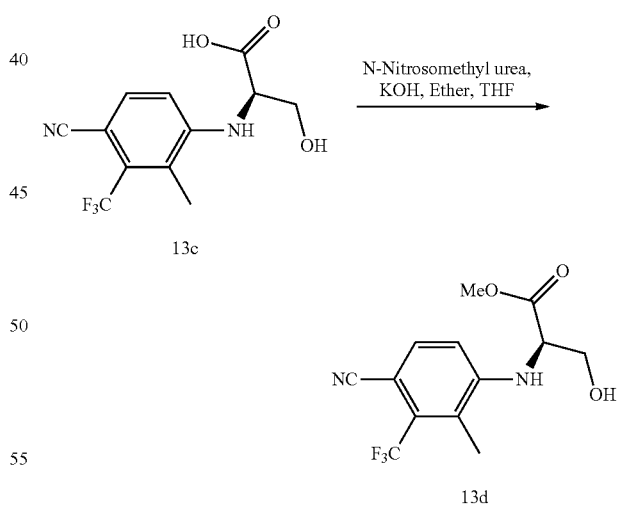

To a solution of (R)-2-((4-cyano-2-methyl-3-(trifluoromethyl)phenyl)amino)-3-hydroxypropanoic acid (13c) (0.8 g, 2.7 mmol) in THF (20 mL), cooled to 0° C., diazomethane [prepared by N-Nitrosomethyl urea (0.84 g, 8.3 mmol) and 40% KOH solution (20 mL) in ether (20 mL)] was added under nitrogen atmosphere and stirred for 15 min. After completion of the reaction (by TLC), the reaction mixture was diluted with water (20 mL) and extracted with EtOAc (3×20 mL). The combined organic extracts were dried over Na₂SO₄ and concentrated under reduced pressure to afford the ester 13d (0.7 g, crude) as a white solid which was carried forward to the next step without purification.

TLC: 50% EtOAc/Hexane (R_f: 0.7)

¹H NMR (500 MHz, CDCl₃, δ in ppm): 7.53 (d, J=8.5 Hz, 1H), 6.71 (d, J=8.5 Hz, 1H), 5.30 (d, J=7.0 Hz, 1H), 4.29-4.26 (m, 1H), 4.13-4.09 (m, 1H), 4.08-4.00 (m, 1H), 3.84 (s, 3H), 2.33 (s, 3H), 1.98 (t, J=6.0 Hz, 1H).

Mass (ESI): 303.9 [M⁺+1]

13d to 13e (R)-methyl 3-(4-cyano-2-methyl-3-(trifluoromethyl)phenyl)-2-oxooxazolidine-4-carboxylate

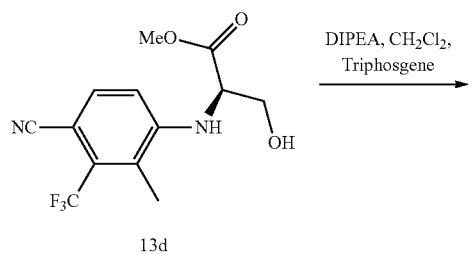

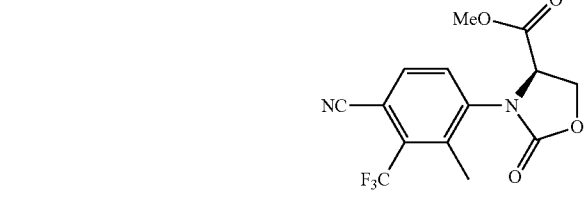

To a solution of (R)-methyl 2-((4-cyano-2-methyl-3-(trifluoromethyl)phenyl)amino)-3-hydroxypropanoate (13d) (0.7 g, 2.3 mmol) in dry CH₂Cl₂ (20 mL), cooled to −78° C., DIPEA (1.1 mL, 6.9 mmol) followed by Triphosgene (1.1 g, 3.6 mmol) dissolved in dry CH₂Cl₂ (5 mL) was added under nitrogen atmosphere. The resulting reaction mixture was brought to room temperature and stirred for 16 h. After completion of reaction (by TLC), the reaction mixture was diluted with water (30 mL) and extracted with CH₂Cl₂ (3×15 mL). The combined organic extracts were dried over Na₂SO₄ and concentrated under reduced pressure to give the crude compound. The crude material was purified by column chromatography to provide the oxazolidinone 13e (0.65 g, 85%) as a white solid.

¹H NMR (500 MHz, CDCl₃, δ in ppm): 7.73 (d, J=8.5 Hz, 1H), 7.66 (d, J=7.5 Hz, 1H), 4.83-4.77 (m, 2H), 4.56 (dd, J=9.0, 4.5 Hz, 1H), 3.74 (s, 3H), 2.49 (d, J=1.5 Hz, 3H).

TLC: 5% CH₃OH/CH₂Cl₂ (R_f: 0.8)

13e to 13f (S)-4-(4-(hydroxymethyl)-2-oxooxazolidin-3-yl)-3-methyl-2-(trifluoromethyl)benzonitrile

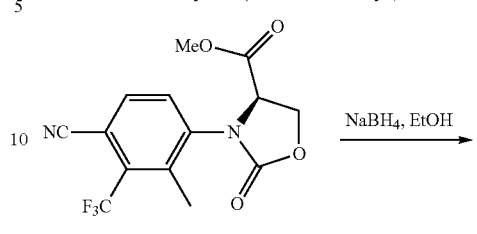

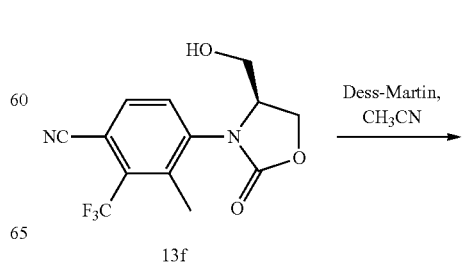

To a solution of (R)-methyl 3-(4-cyano-2-methyl-3-(trifluoromethyl)phenyl)-2-oxooxazolidine-4-carboxylate (13e) (0.6 g, 1.8 mmol) in EtOH (10 mL), cooled to 0° C., NaBH₄ (0.084 g, 2.2 mmol) was added under nitrogen atmosphere. The resulting reaction mixture was warmed to room temperature and stirred for 3 h. After completion of reaction (by TLC), the volatiles were removed under reduced pressure and the residue was diluted with saturated NH₄Cl solution (20 mL) and extracted with EtOAc (3×15 mL). The combined organic extracts were dried over Na₂SO₄ and concentrated under reduced pressure to give the crude compound which was purified by column chromatography to furnish the alcohol 13f (0.35 g, 64%) as white syrupy mass.

TLC: 100% EtOAc (R_f: 0.45)

¹H NMR (500 MHz, DMSO-d₆, δ in ppm): 8.07 (d, J=8.0 Hz, 1H), 7.91 (d, J=8.0 Hz, 1H), 5.11 (s, 1H), 4.61 (t, J=9.0 Hz, 1H), 4.34 (t, J=8.0 Hz, 1H), 3.42-3.40 (m, 2H), 2.39 (d, J=2.0 Hz, 3H).

13f to Examples 13 and 14

3-methyl-4-((R)-2-oxo-4-((S)-2,2,2-trifluoro-1-hydroxyethyl)oxazolidin-3-yl)-2-(trifluoromethyl)benzonitrile 13

& 3-Methyl-4-((R)-2-oxo-4-((R)-2,2,2-trifluoro-1-hydroxyethyl)oxazolidin-3-yl)-2-(trifluoromethyl)benzonitrile 14

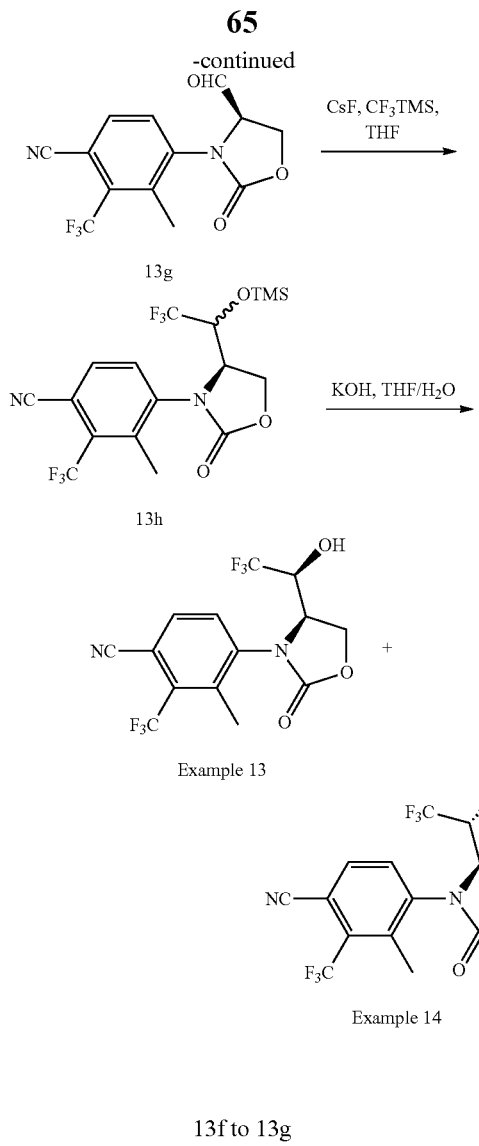

Example 13

Example 14

13f to 13g

To a solution of (S)-4-(4-(hydroxymethyl)-2-oxooxazolidin-3-yl)-3-methyl-2-(trifluoromethyl)benzonitrile (13f) (0.45 g, 1.5 mmol) in CH₃CN (20 mL), cooled to 0° C., Dess-Martin periodinane (1.27 g, 3.0 mmol) was added. The reaction was stirred at 0° C. for 16 h, quenched with saturated NaHCO₃ solution (20 mL) and extracted with CH₂Cl₂ (3×15 mL). The combined organic extracts were dried over Na₂SO₄ and concentrated under reduced pressure to provide the aldehyde 13g (0.36 g, crude). The crude material was used for the next step without purification.

TLC: 10% MeOH/CH₂Cl₂ (eluted twice) (R$_f$: 0.65)

13g to 13h

The crude aldehyde 13g (0.36 g, 1.2 mmol) was dissolved in THF (20 mL), cooled to 0° C., and CsF (174 mg, 1.15 mmol) followed by CF₃TMS (1.8 mL, 12.0 mmol) was added. The reaction mixture was stirred at 0° C. for 4 h. After the completion of reaction (by TLC), the reaction mixture was quenched with saturated NH₄Cl solution (20 mL) and extracted with EtOAc (3×20 mL). The combined organic extracts were dried over Na₂SO₄ and concentrated under reduced pressure to provide the silyl ether 13h as a mixture of diastereomers (0.3 g, crude). The crude material was taken to the next step without purification.

TLC: 100% EtOAc (R$_f$: 0.7 & 0.8)

13h to Examples 13 and 14

The crude silyl ether 13h (0.3 g, 0.68 mmol) was taken in THF (10 mL), cooled to 0° C., and KOH (0.112 g, 2.03 mmol) dissolved in water (10 mL) was added. The reaction mixture was stirred at 0° C. for 1 h, diluted with water (20 mL) and extracted with EtOAc (3×10 mL). The combined organic extracts were dried over Na₂SO₄ and concentrated under vacuo to provide the crude residue which was purified by column chromatography followed by preparative HPLC to furnish 13 (0.050 g) and 14 (0.018 g) both as white solids.

TLC: 60% EtOAc/Hexane (R$_f$: 13 0.3 & 0.7 14)

Example 13

$^1$H NMR (500 MHz, CDCl₃, δ in ppm): 7.73 (d, J=8.0 Hz, 1H), 7.60 (br s, 1H), 4.74 (t, J=9.5 Hz, 1H), 4.65 (m, 1H), 4.50-4.47 (t, J=9.0 Hz, 1H), 4.17 (m, 1H), 2.61 (s, 1H), 2.50 (s, 3H).

HPLC purity: 98.13%

Mass (ESI): 367.7[M$^+$−1]

Example 14

$^1$H NMR (500 MHz, DMSO-d₆, δ in ppm): 8.12 (d, J=8.0 Hz, 1H), 8.07 (br s, 1H), 7.13 (s, 1H), 5.05 (br s, 1H), 4.62-4.53 (m, 2H), 4.02 (t, J=8.0 Hz, 1H), 2.38 (s, 3H).

HPLC purity: 92.98%

Mass (ESI): 481.1 [M$^+$+TFA]

Examples 15 and 16

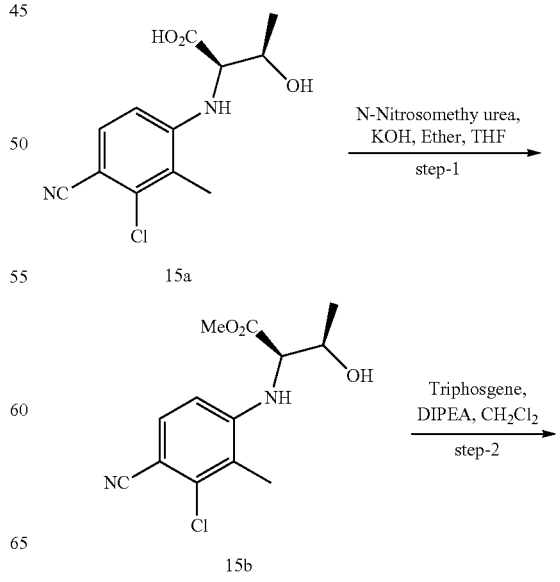

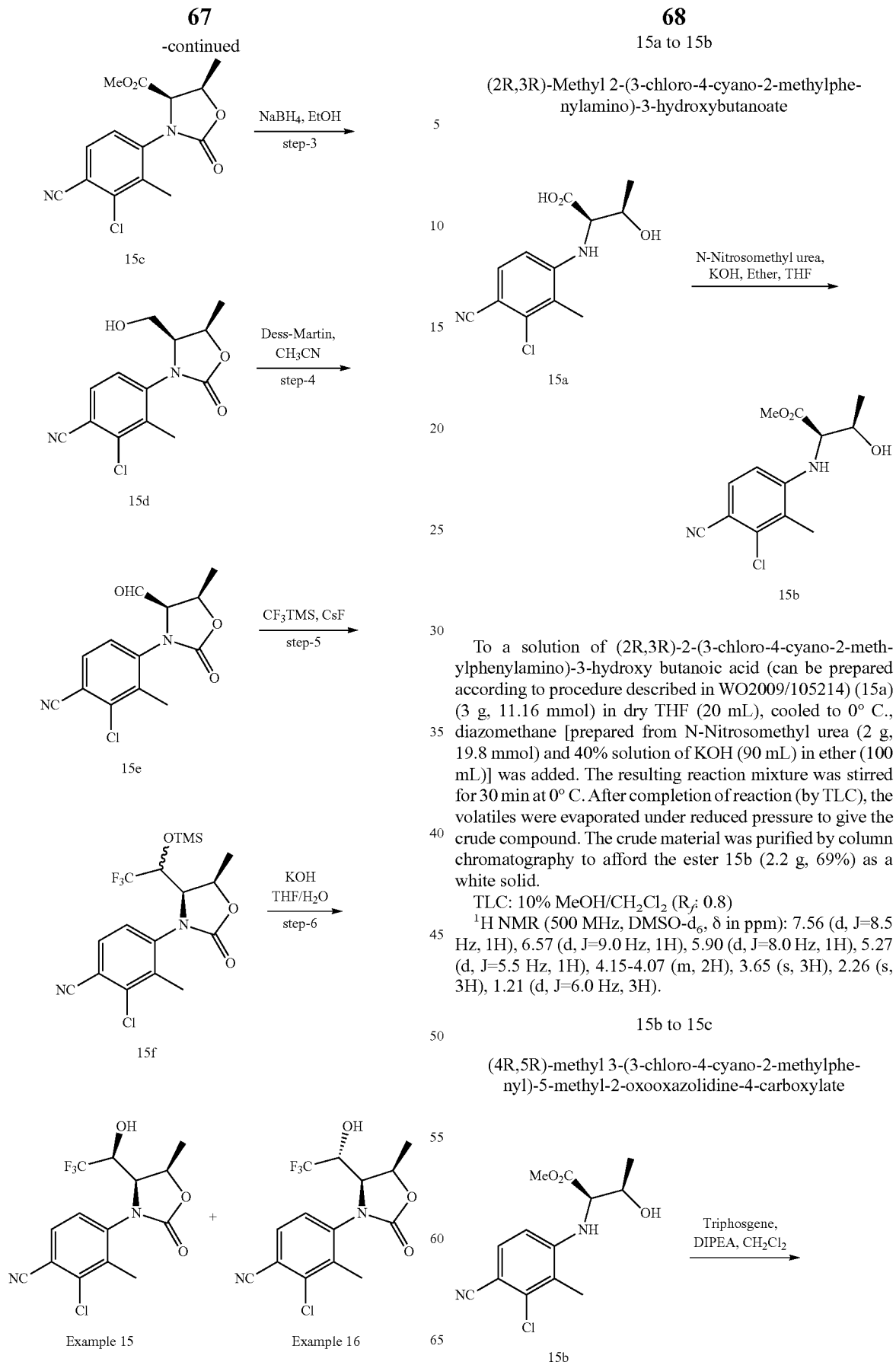

15a to 15b (2R,3R)-Methyl 2-(3-chloro-4-cyano-2-methylphenylamino)-3-hydroxybutanoate To a solution of (2R,3R)-2-(3-chloro-4-cyano-2-methylphenylamino)-3-hydroxy butanoic acid (can be prepared according to procedure described in WO2009/105214) (15a) (3 g, 11.16 mmol) in dry THF (20 mL), cooled to 0° C., diazomethane [prepared from N-Nitrosomethyl urea (2 g, 19.8 mmol) and 40% solution of KOH (90 mL) in ether (100 mL)] was added. The resulting reaction mixture was stirred for 30 min at 0° C. After completion of reaction (by TLC), the volatiles were evaporated under reduced pressure to give the crude compound. The crude material was purified by column chromatography to afford the ester 15b (2.2 g, 69%) as a white solid.

TLC: 10% MeOH/CH$_2$Cl$_2$ (R$_f$: 0.8)

$^1$H NMR (500 MHz, DMSO-d$_6$, δ in ppm): 7.56 (d, J=8.5 Hz, 1H), 6.57 (d, J=9.0 Hz, 1H), 5.90 (d, J=8.0 Hz, 1H), 5.27 (d, J=5.5 Hz, 1H), 4.15-4.07 (m, 2H), 3.65 (s, 3H), 2.26 (s, 3H), 1.21 (d, J=6.0 Hz, 3H).

15b to 15c (4R,5R)-methyl 3-(3-chloro-4-cyano-2-methylphenyl)-5-methyl-2-oxooxazolidine-4-carboxylate

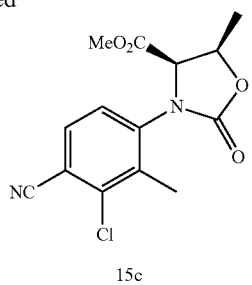

15c

To a solution of (2R,3R)-Methyl 2-(3-chloro-4-cyano-2-methylphenylamino)-3-hydroxy butanoate (15b) (1.7 g, 6.0 mmol) in dry $CH_2Cl_2$ (30 mL), cooled to −78°C., DIPEA (3.0 mL, 18.2 mmol) was added followed by Triphosgene (2.66 g, 9.0 mmol) dissolved in $CH_2Cl_2$ (10 mL). The resulting reaction mixture was allowed to warm to room temperature and stirred for 16 h. After completion of reaction (by TLC), the reaction mixture was diluted with ice-cold water (40 mL) and extracted with $CH_2Cl_2$ (2×50 mL). The combined organic extracts were dried over $Na_2SO_4$, filtered and concentrated under reduced pressure to give the crude compound. The crude material was purified by silica gel column chromatography to afford the oxazolidinone 15c (1.5 g, 81%) as a white solid.

TLC: 5% $MeOH/CH_2Cl_2$ ($R_f$: 0.8)

$^1$H NMR (500 MHz, DMSO-$d_6$, δ in ppm): 7.90 (d, J=8.5 Hz, 1H), 7.60 (d, J=9.0 Hz, 1H), 5.35 (d, J=8.0 Hz, 1H), 5.23-5.20 (m, 1H), 3.70 (s, 3H), 2.38 (s, 3H), 1.26 (d, J=5.5 Hz, 3H).

15c to 15d 2-chloro-4-((4S,5R)-4-(hydroxymethyl)-5-methyl-2-oxooxazolidin-3-yl)-3-methylbenzonitrile

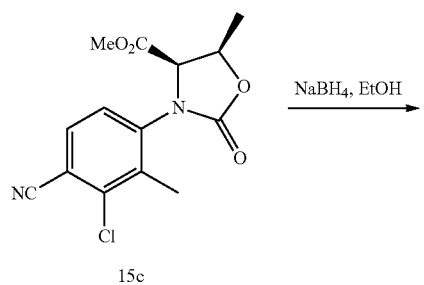

To a stirred solution of (4R,5R)-methyl 3-(3-chloro-4-cyano-2-methyl phenyl)-5-methyl-2-oxooxazolidine-4-carboxylate (15c) (1.5 g, 4.8 mmol) in EtOH (100 mL), cooled to 0°C., $NaBH_4$ (0.2 g, 5.3 mmol) was added and the resulting reaction mixture was stirred for further 2 h. After completion of reaction (by TLC), the volatiles were removed under reduced pressure and the residue was diluted with cold water (30 mL) and extracted with EtOAc (2×50 mL). The combined organic extracts were dried over $Na_2SO_4$ and concentrated under reduced pressure to give the crude compound which was purified by column chromatography to provide the alcohol 15d (1.1 g, 80%) as syrup.

TLC: 50% EtOAc/Hexane ($R_f$: 0.4)

$^1$H NMR (500 MHz, DMSO-$d_6$, δ in ppm): 7.92 (d, J=8.5 Hz,1H), 7.59 (d, J=8.0 Hz, 1H), 5.05-5.01 (m, 1H), 4.70-4.65 (m, 1H), 4.05 (br s, 1H), 3.47-3.39 (m, 1H), 3.35-3.31 (m, 1H), 2.33 (s, 3H), 1.49 (d, J=6.5 Hz, 3H).

Mass (ESI): 279.4 [M$^+$−1]

15d to Examples 15 and 16

2-chloro-3-methyl-4-((4S,5R)-5-methyl-2-oxo-4-((S)-2,2,2-trifluoro-1-hydroxy ethyl)oxazolidin-3-yl)benzonitrile 15 &

2-chloro-3-methyl-4-((4S,5R)-5-methyl-2-oxo-4-((R)-2,2,2-trifluoro-1-hydroxyethyl)oxazolidin-3-yl)benzonitrile 16

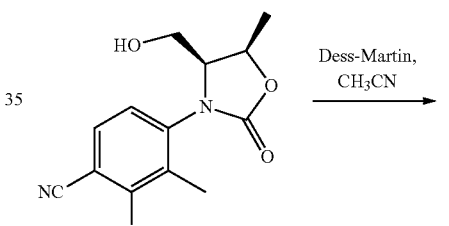

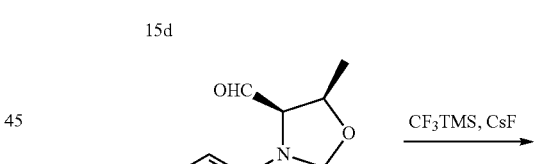

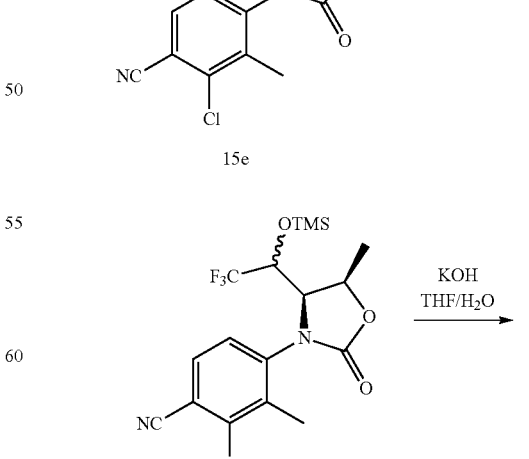

-continued

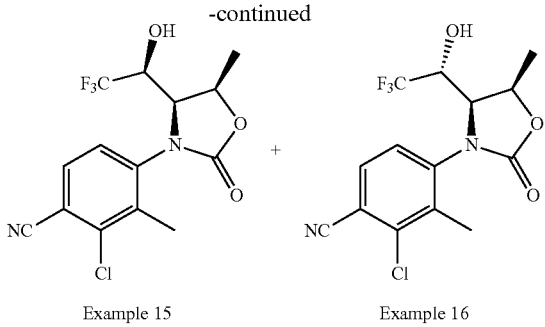

Example 15     Example 16

15d to 15e

To a solution of 2-chloro-4-((4S,5R)-4-(hydroxymethyl)-5-methyl-2-oxooxazolidin-3-yl)-3-methylbenzonitrile (15d) (0.5 g, 1.8 mmol) in CH₃CN (30 mL), cooled to 0° C., Dess-Martin periodinane (1.45 g, 3.42 mmol) was added. The resulting reaction mixture was slowly brought to room temperature and stirred for 30 min. After completion of reaction (by TLC), saturated NaHCO₃ solution (30 mL) was added to the reaction mixture and extracted with EtOAc (2×50 mL). The combined organic extracts were dried over Na₂SO₄ and concentrated under reduced pressure to afford the aldehyde 15e (0.45 g, crude) as a syrup which was taken for the next step without further purification.

TLC: 10% MeOH/DCM ($R_f$: 0.7).

15e to 15f

The crude aldehyde 15e (0.45 g, 1.6 mmol) was dissolved in THF (50 mL), cooled to 0° C., and CsF (245 mg, 1.6 mmol) was added followed by CF₃TMS (2.3 g, 16.2 mmol). The resulting reaction mixture was stirred for 2 h at 0° C. After completion of reaction (by TLC), the reaction mixture was quenched with saturated NH₄Cl solution (50 mL) and extracted with EtOAc (2×100 mL). The combined organic extracts were dried over Na₂SO₄ and concentrated under reduced pressure to afford the silyl ether 15f as a mixture of diastereomers (0.6 g, crude) which was carried forward without purification.

TLC: 50% EtOAc/Hexane ($R_f$: 0.6 & 0.8)

15f to Examples 15 and 16

To a solution of silyl ether 15f (0.6 gm, 1.4 mmol) in THF (20 mL), cooled to 0° C., KOH (0.24 gm, 4.3 mmol) in water (20 mL) was added. The resulting reaction mixture was stirred at 0° C. for 1 h, diluted with water (40 mL) and extracted with EtOAc (2×80 mL). The combined organic extracts were dried over Na₂SO₄ and concentrated under reduced pressure to give the crude mixture which was purified by column chromatography followed by preparative HPLC to afford 15 (35 mg) and 16 (18 mg) both as white solids.

TLC: 50% EtOAc/Hexane ($R_f$: 0.3 15 & 0.6 16)

Example 15

¹H NMR (500 MHz, DMSO-d₆, δ in ppm): 7.89 (d, J=8.5 Hz, 1H), 7.74 (br s, 1H), 6.93 (d, J=6.5 Hz, 1H), 4.66 (t, J=5.5 Hz, 1H), 4.40 (d, J=8.0 Hz, 2H), 2.33 (s, 3H), 1.53 (d, J=6.0 Hz, 3H)

Mass (ESI): 347.1 [M⁺−1]
HPLC purity: 99.75%

Example 16

¹H NMR (500 MHz, DMSO-d₆, δ in ppm): 7.97 (d, J=8.5 Hz, 1H), 7.75 (br s, 1H), 7.11 (br s, 1H), 4.90 (t, J=6.0 Hz, 1H), 4.55 (bs, 1H), 3.96 (t, J=6.0 Hz, 1H), 2.31 (s, 3H), 1.50 (d, J=6.0 Hz, 3H).

Mass (ESI): 347.0 [M⁺−1]
HPLC purity: 98.68%

Examples 17 and 18

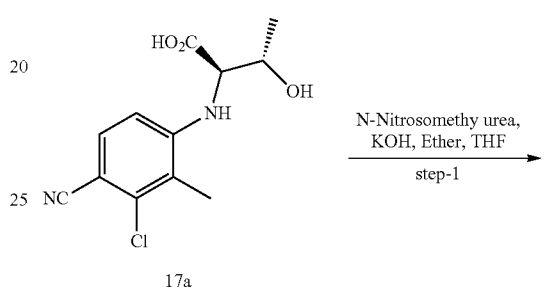

17a

N-Nitrosomethy urea, KOH, Ether, THF
step-1

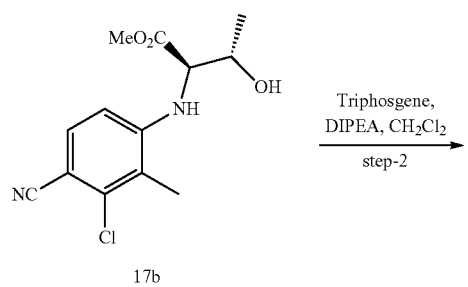

17b

Triphosgene, DIPEA, CH₂Cl₂
step-2

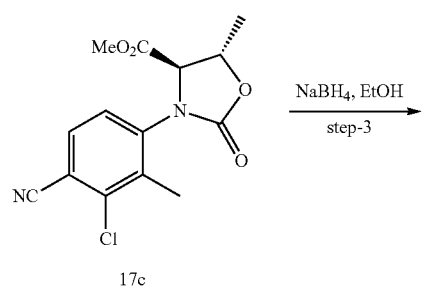

17c

NaBH₄, EtOH
step-3

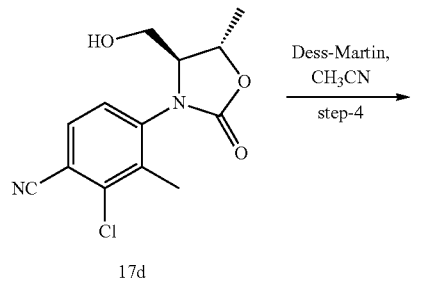

17d

Dess-Martin, CH₃CN
step-4

-continued

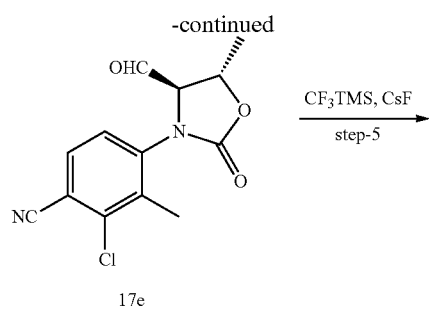

17e

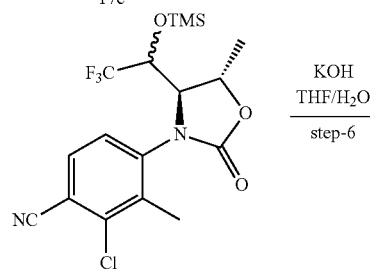

17f

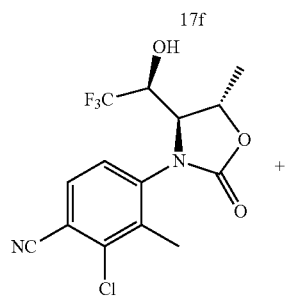 + 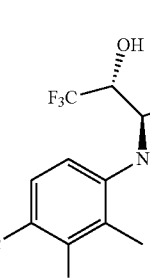

Example 17    Example 18

17a

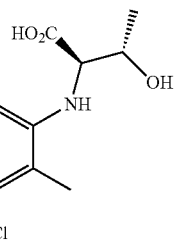

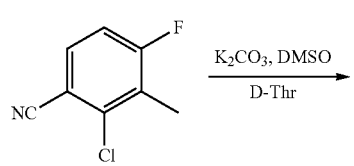

17a

To a stirred solution of D-Threonine (4.63 g, 38.8 mmol) in DMSO (50 mL), cooled to 0° C. K₂CO₃ (4.7 g, 34.8 mmol) was added. After being stirred for 15 min, 2-chloro-4-fluoro-3-methylbenzonitrile (3.0 g, 17.7 mmol) was added to the reaction mixture. The resulting reaction mixture was heated to 80° C. for 36 h. After completion of reaction (by TLC), the reaction mixture was brought to room temperature, diluted with water (50 mL) and extracted with EtOAc (3×30 mL). The aqueous layer was acidified by citric acid (pH 2-3) and extracted with EtOAc (3×50 mL). The combined organic extracts were washed with ice-cold water (5×30 mL), dried over Na₂SO₄ and concentrated under reduced pressure to give the crude product. The crude material was triturated with 10% EtOAc/Hexane to afford the acid 17a (2.0 g, 42%) as an off-white solid.

TLC: 30% MeOH/DCM ($R_f$: 0.2)

¹H NMR (500 MHz, DMSO-$d_6$, δ in ppm): 7.54 (d, J=8.5 Hz, 1H), 6.58 (d, J=9.0 Hz, 1H), 5.46 (d, J=9.0 Hz, 1H), 4.25-4.23 (dd, J=6.5, 3.5 Hz, 1H), 4.13-4.11 (dd, J=8.5, 3.0 Hz, 1H), 2.26 (s, 3H), 1.19 (d, J=6.5 Hz, 3H).

17a to 17b (2R,3S)-methyl-2-(3-chloro-4-cyano-2-methylphenylamino)-3-hydroxybutanoate

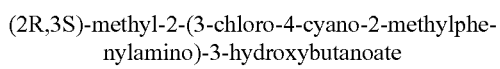

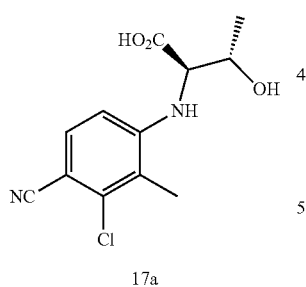

17b

To a solution of (2R,3S)-2-(3-chloro-4-cyano-2-methylphenylamino)-3-hydroxybutanoic acid (17a) (2.0 g, 7.9 mmol) in THF (20 mL), cooled to 0° C., diazomethane [prepared by N-Nitrosomethyl urea (2.2 g) and 40% KOH solution (90 mL) in ether (40 mL)] was added and stirred for 15 min. After completion of reaction (by TLC), the reaction mixture was diluted with water (50 mL). The organic layer was separated, dried over Na₂SO₄ and concentrated under reduced pressure to give crude compound which was triturated with hexane to afford the ester 17b (1.8 g, 86%) as a white solid.

TLC: 50% EtOAc/Hexane ($R_f$: 0.6)

¹H NMR (500 MHz, CDCl₃, δ in ppm): 7.38 (d, J=8.5 Hz, 1H), 6.45 (d, J=8.5 Hz, 1H), 5.06 (d, J=8.0 Hz, 1H), 4.36 (br s, 1H), 4.04 (dd, J=8.5, 2.5 Hz, 1H), 3.79 (s, 3H), 2.32 (s, 3H), 2.20 (d, J=3.5 Hz, 1H), 1.33 (d, J=6.5 Hz, 3H).

Mass (ESI): 283 [M+1]

17b to 17c

(4R,5S)-Methyl 3-(3-chloro-4-cyano-2-methylphenyl)-5-methyl-2-oxooxazolidine-4-carboxylate

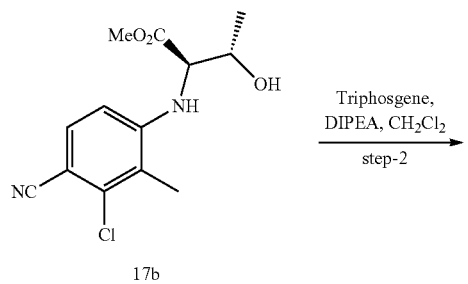

17b

To a solution of (2R,3S)-Methyl 2-(3-chloro-4-cyano-2-methylphenylamino)-3-hydroxybutanoate (17b) (1.8 g, 6.3 mmol) in dry CH$_2$Cl$_2$ (20 mL), cooled to −78° C., DIPEA (3 mL) was added followed by Triphosgene (2.8 g, 9.5 mmol) taken in CH$_2$Cl$_2$ (10 mL). The reaction mixture was slowly brought to room temperature and stirred for 16 h. After completion of reaction (by TLC), the reaction mixture was diluted with water (50 mL) and extracted with CH$_2$Cl$_2$ (3×50 mL). The combined organic extracts were washed with water (3×50 mL), dried over Na$_2$SO$_4$, and concentrated under reduced pressure to give the crude compound. The crude material was purified by column chromatography to provide the oxazolidinone 17c (1.2 g, 61%) as an off white solid.

TLC: 40% EtOAc/Hexane (R$_f$: 0.6)

$^1$H NMR (500 MHz, CDCl$_3$, δ in ppm): 7.56 (d, J=8.0 Hz, 1H), 7.30 (d, J=8.0 Hz, 1H), 4.77 (t, J=6.0 Hz, 1H), 4.43 (d, J=5.5 Hz, 1H), 3.73 (s, 3H), 2.43 (s, 3H), 1.70 (d, J=6.5 Hz, 3H).

17c to 17d

2-chloro-4-((4S,5S)-4-(hydroxymethyl)-5-methyl-2-oxooxazolidin-3-yl)-3-methylbenzonitrile

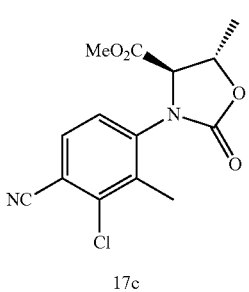

17c

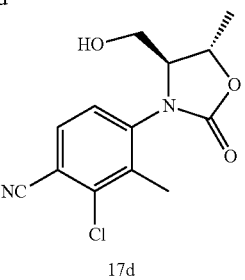

17d

The oxazolidinone 17c (1.2 gm, 4.0 mmol) was taken in EtOH (20 mL), cooled to 0° C., and NaBH$_4$ (0.176 g, 4.6 mmol) was added and stirred at 0° C. for 4 h. After completion of reaction (by TLC), the volatiles were evaporated under reduced pressure and the residue was diluted with aqueous NH$_4$Cl (30 mL) and extracted with EtOAc (3×50 mL). The combined organic extracts were washed with aqueous NH$_4$Cl (2×50 mL). The organic layer was separated, dried over Na$_2$SO$_4$, and concentrated under reduced pressure to give the crude compound which was purified by column chromatography to furnish the alcohol 17d (1.0 g, 91%) as an off-white solid.

TLC: 60% EtOAc/Hexane (R$_f$: 0.3)

$^1$H NMR (500 MHz, DMSO-d$_6$, δ in ppm): 7.92 (d, J=8.5 Hz, 1H), 7.59 (d, J=8.5 Hz, 1H), 5.06 (t, J=5.0 Hz, 1H), 4.70-4.65 (m, 1H), 4.05 (br s, 1H), 3.44-3.40 (m, 1H), 3.35-3.31 (m, 1H), 2.30 (s, 3H), 1.49 (d, J=6.5 Hz, 3H).

17d to Examples 17 and 18

2-chloro-3-methyl-4-((4S,5S)-5-methyl-2-oxo-4-((S)-2,2,2-trifluoro-1-hydroxyethyl)oxazolidin-3-yl)benzonitrile 17 &

2-chloro-3-methyl-4-((4S,5S)-5-methyl-2-oxo-4-((R)-2,2,2-trifluoro-1-hydroxyethyl)oxazolidin-3-yl)benzonitrile 18

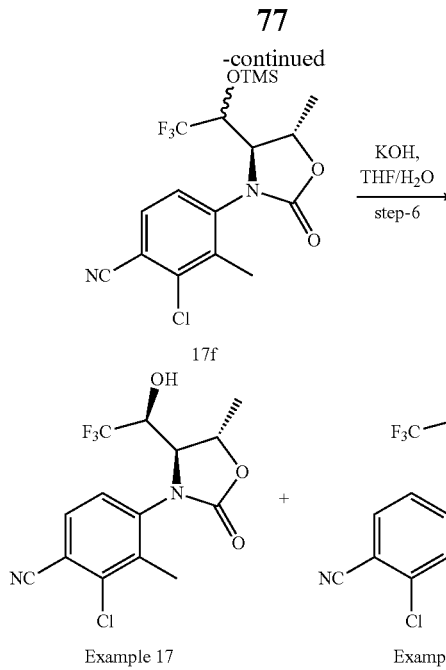

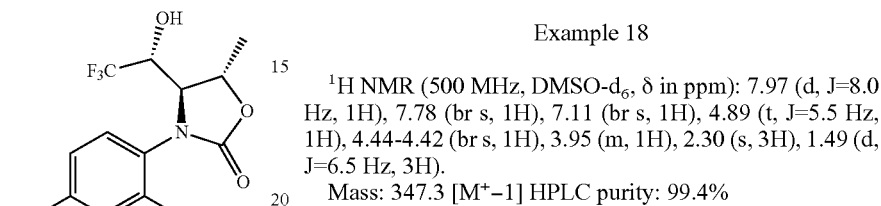

vacuo to provide the crude mixture which was purified by column chromatography to afford 17 (0.032 g) and 18 (0.016 g) both as white solids.

TLC: 50% EtOAc/Hexane ($R_f$: 0.3 17 & 0.4 18)

Example 17

$^1$H NMR (500 MHz, DMSO-$d_6$, δ in ppm): 7.89 (d, J=8.5 Hz, 1H), 7.73 (br s, 1H), 6.93 (d, J=6.0 Hz, 1H), 4.67 (d, J=5.0 Hz, 1H), 4.39 (d, J=7.0 Hz, 2H), 2.33 (s, 3H), 1.53 (d, J=6.5 Hz, 3H).

Mass: 347.3 [M$^+$−1] HPLC purity: 96.3%

Example 18

$^1$H NMR (500 MHz, DMSO-$d_6$, δ in ppm): 7.97 (d, J=8.0 Hz, 1H), 7.78 (br s, 1H), 7.11 (br s, 1H), 4.89 (t, J=5.5 Hz, 1H), 4.44-4.42 (br s, 1H), 3.95 (m, 1H), 2.30 (s, 3H), 1.49 (d, J=6.5 Hz, 3H).

Mass: 347.3 [M$^+$−1] HPLC purity: 99.4%

Examples 19 and 20

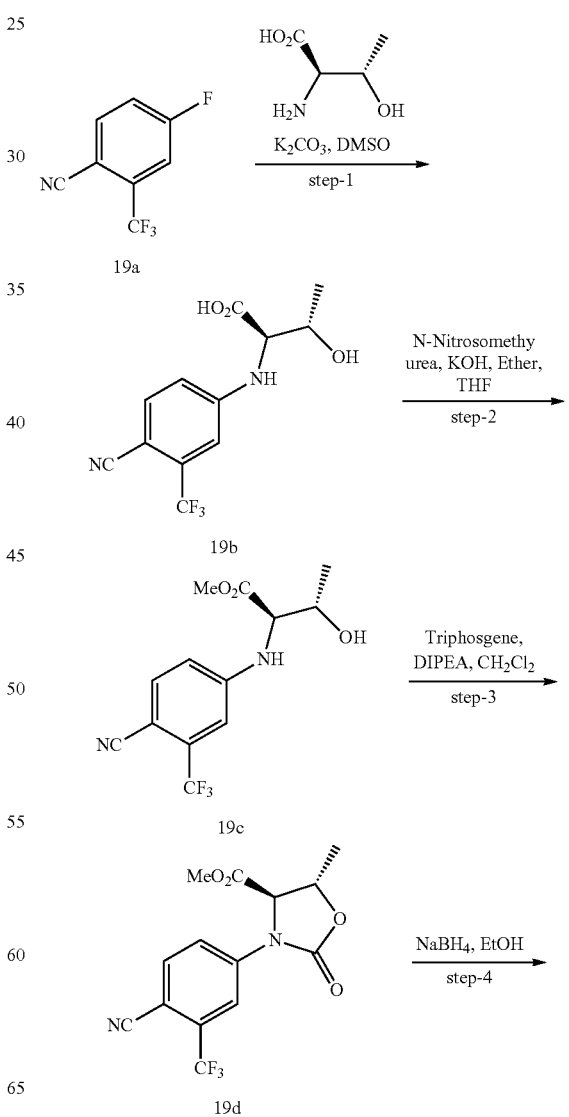

17d to 17e

To a stirred solution of 2-chloro-4-((4S,5S)-4-(hydroxymethyl)-5-methyl-2-oxooxazolidin-3-yl)-3-methylbenzonitrile (17d) (0.6 g, 2.14 mmol) in CH$_3$CN (20 mL), cooled to 0° C., Dess-Martin periodinane (1.8 g, 4.2 mmol) was added portion wise at under nitrogen atmosphere. The reaction mixture was stirred at 0° C. for further 3 h. After completion of reaction (by TLC), the reaction mixture was diluted with aqueous NaHCO$_3$ solution (20 mL) and extracted with CH$_2$Cl$_2$ (2×50 mL). The combined organic extracts were dried over Na$_2$SO$_4$ and concentrated under reduced pressure to afford the aldehyde 17e (0.5 g, crude) as an off-white solid which was taken for the next step without purification.

TLC: 10% MeOH/DCM ($R_f$: 0.5)

17e to 17f

To a solution of the crude aldehyde 17e (0.5 g, 1.79 mmol) in dry THF (30 mL), cooled to 0° C., CsF (0.271 g, 1.7 mmol) was added followed by CF$_3$TMS (3.6 mL, 17.6 mmol) under nitrogen atmosphere. The reaction was continued at 0° C. for 16 h. After completion of reaction (by TLC), the reaction mixture was quenched with aqueous NH$_4$Cl (30 mL) and extracted with EtOAc (3×30 mL). The combined organic extracts were dried over Na$_2$SO$_4$ and concentrated under reduced pressure to afford the silyl ether 17f as a mixture of diastereomers (0.4 g, crude). The crude material was used for the next step without purification.

TLC: 50% EtOAc/Hexane ($R_f$: 0.3&0.6)

17f to Examples 17 and 18

The crude silyl ether 17f (0.4 gm, 0.95 mmol) was dissolved in THF (20 mL), cooled to 0° C., and KOH (0.156 g, 0.28 mmol) taken in water (20 mL) was added. The reaction was stirred at 0° C. for 2 h. After completion of reaction (by TLC), the reaction mixture was diluted with water (20 mL) and extracted with EtOAc (3×30 mL). The combined organic extracts were dried over Na$_2$SO$_4$ and concentrated under -continued

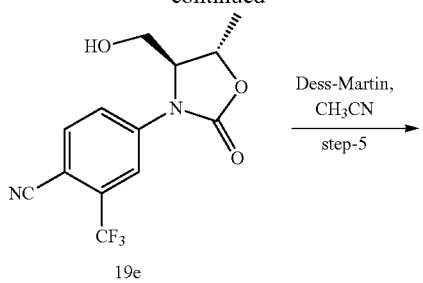
19e

Dess-Martin, CH₃CN
step-5

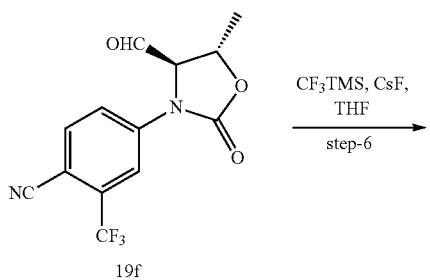
19f

CF₃TMS, CsF, THF
step-6

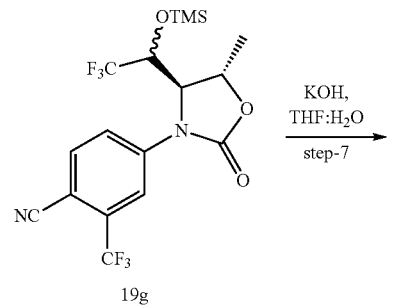
19g

KOH, THF:H₂O
step-7

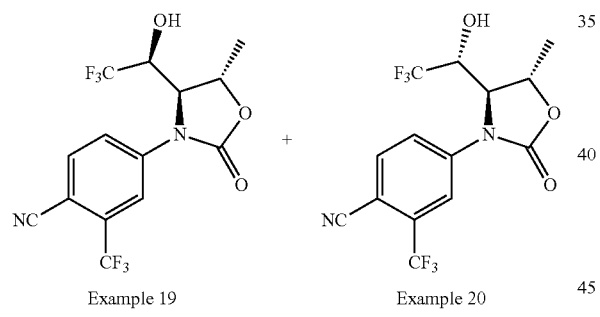
Example 19      Example 20

19a to 19b (2R,3S)-2-(4-Cyano-3-(trifluoro methyl)phenyl amino)-3-hydroxybutanoic acid

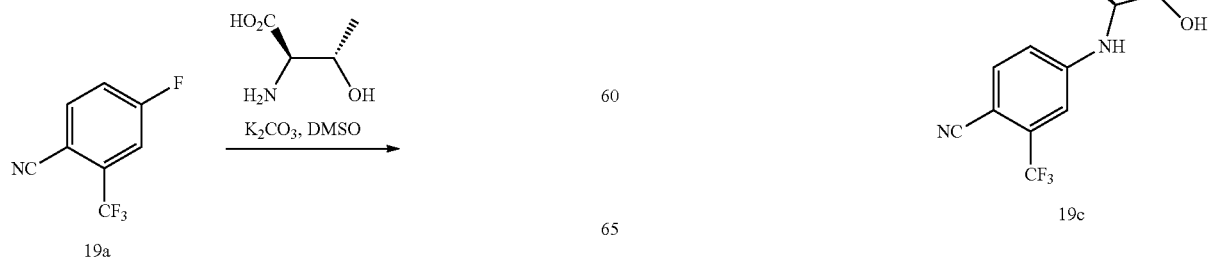
19a

-continued

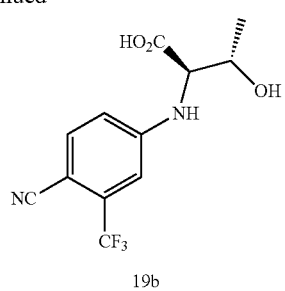
19b

To a solution of D-Threonine (4.14 g, 34.8 mmol) in DMSO (30 mL), K₂CO₃ (4.36 g, 31.6 mmol) followed by 4-Fluoro-2-(trifluoromethyl)benzonitrile (19a) (3.0 g, 15.8 mmol) was added at room temperature. The reaction was heated to 80° C. for 16 h. After completion of reaction (by TLC), the reaction mixture was diluted with water (100 mL) and extracted with EtOAc (3×50 mL). The aqueous layer was acidified with citric acid and extracted with EtOAc (2×100 mL). The combined organic extracts were dried over Na₂SO₄ and concentrated under reduced pressure to afford the acid 19b (2.02 g, crude) as syrup which was taken for the next step without purification.

TLC: 30% MeOH/DCM ($R_f$: 0.4)

¹H NMR (500 MHz, DMSO-d₆, δ in ppm): 7.71 (d, J=9.0 Hz, 1H), 7.27 (br s, 1H), 7.15 (d, J=8.5 Hz, 1H), 6.93 (br s, 1H), 4.24-4.21 (m, 1H), 4.15-4.13 (m, 1H), 3.32 (br s, 1H), 1.19-1.16 (m, 3H).

19b to 19c (2R,3S)-Methyl 2-(4-cyano-3-(trifluoromethyl)phenylamino)-3-hydroxy butanoate N-Nitrosomethyl urea, KOH, Ether, THF
step-2

19c (2R,3S)-2-(4-Cyano-3-(trifluoro methyl)phenyl amino)-3-hydroxybutanoic acid (19b) (2.0 g, 6.94 mmol) was dissolved in THF (20 mL), cooled to 0° C., and diazomethane [prepared by N-Nitrosomethyl urea (2.1 g, 20.8 mmol) and 40% KOH solution (100 mL) in ether (40 mL)] was added. The resulting reaction mixture was slowly warmed to room temperature and stirred for 30 min. After completion of reaction (by TLC), the reaction mixture was poured into water (80 mL) and extracted with EtOAc (2×100 mL). The combined organic extracts were dried over $Na_2SO_4$, filtered and concentrated under reduced pressure to give the crude compound. The crude material was purified by column chromatography to afford the ester 19c (1.8 g, 86%) as a syrup.

TLC: 50% EtOAc/Hexane ($R_f$: 0.5)

$^1$H NMR (500 MHz, DMSO-$d_6$, δ in ppm): 7.20 (d, J=8.5 Hz, 1H), 7.30 (br s, 1H), 7.23 (d, J=8.5 Hz, 1H), 6.93 (br s, 1H), 5.16 (d, J=5.5 Hz, 1H), 4.32 (dd, J=9.0, 3.0 Hz, 1H), 4.25-4.22 (m, 1H), 3.66 (s, 3H), 1.19-1.14 (m, 3H).

19c to 19d (4R,5S)-methyl 3-(4-cyano-3-(trifluoromethyl)phenyl)-5-methyl-2-oxooxazolidine-4-carboxylate

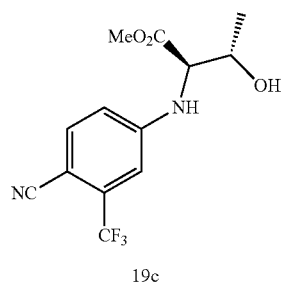

19c

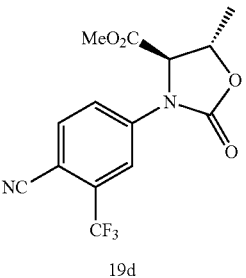

19d

To a solution of (2R,3S)-Methyl 2-(4-cyano-3-(trifluoromethyl)phenylamino)-3-hydroxy butanoate (19c) (1.8 g, 5.96 mmol) in dry $CH_2Cl_2$ (30 mL), cooled to −78° C., DIPEA (2.93 mL, 17.8 mmol) followed by Triphosgene (2.63 g, 8.9 mmol) taken in dry $CH_2Cl_2$ (10 mL) was added. The resulting reaction mixture was slowly warmed to room temperature and stirred for further 16 h. After completion of reaction (by TLC), the reaction mixture was poured into ice-cold water (100 mL) and extracted with $CH_2Cl_2$ (2×150 mL). The combined organic extracts were dried over $Na_2SO_4$ and concentrated under reduced pressure to give the crude compound.

The crude material was purified by column chromatography to afford the oxazolidinone 19d (1.4 g, 71%) as a thick liquid.

TLC: 60% EtOAc/Hexane ($R_f$: 0.6).

$^1$H NMR (500 MHz, DMSO-$d_6$, δ in ppm): 8.27 (d, J=2.0 Hz, 1H), 8.20 (d, J=8.5 Hz, 1H), 7.85 (dd, J=8.5, 1.5 Hz, 1H), 5.37-5.35 (m, 1H), 4.99-4.95 (m, 1H), 3.73 (s, 3H), 1.52 (d, J=6.5 Hz, 3H).

19d to 19e 4-((4S,5S)-4-(hydroxymethyl)-5-methyl-2-oxooxazolidin-3-yl)-2-(trifluoromethyl)benzonitrile

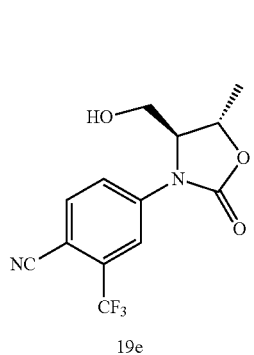

19d

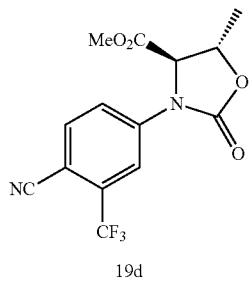

19e

To a solution of (4R,5S)-methyl 3-(4-cyano-3-(trifluoromethyl)phenyl)-5-methyl-2-oxooxazolidine-4-carboxylate (19d) (1.4 g, 4.26 mmol) in EtOH (80 mL), cooled to 0° C., $NaBH_4$ (0.192 g, 5.07 mmol) was added. The resulting reaction mixture was slowly warmed to room temperature and stirred for further 1 h. After completion of reaction (by TLC), the volatiles were removed under reduced pressure and the residue was diluted with saturated $NH_4Cl$ solution (120 mL), stirred for 30 min at room temperature and extracted with EtOAc (2×100 mL). The combined organic extracts were dried over $Na_2SO_4$ and concentrated under reduced pressure to give the crude compound which was purified by column chromatography to furnish the alcohol 19e (1.0 gm, 83%) as a white solid.

TLC: 50% EtOAc/Hexane ($R_f$: 0.2)

$^1$H NMR (500 MHz, DMSO-$d_6$, δ in ppm): 8.33 (d, J=1.5 Hz, 1H), 8.18 (d, J=8.5 Hz, 1H), 7.97 (dd, J=9.0, 2.0 Hz, 1H), 5.12 (t, J=5.5 Hz, 1H), 4.70-4.65 (m, 1H), 4.48-4.46 (m, 1H), 3.66-3.62 (m, 1H), 3.53-3.49 (m, 1H), 1.42 (d, J=6.0 Hz, 3H).

19e to Examples 19 and 20

4-((4S,5S)-5-methyl-2-oxo-4-((S)-2,2,2-trifluoro-1-hydroxyethyl)oxazolidin-3-yl)-2-(trifluoromethyl)benzonitrile 19

4-((4S,5S)-5-methyl-2-oxo-4-((R)-2,2,2-trifluoro-1-hydroxyethyl)oxazolidin-3-yl)-2-(trifluoromethyl)benzonitrile 20

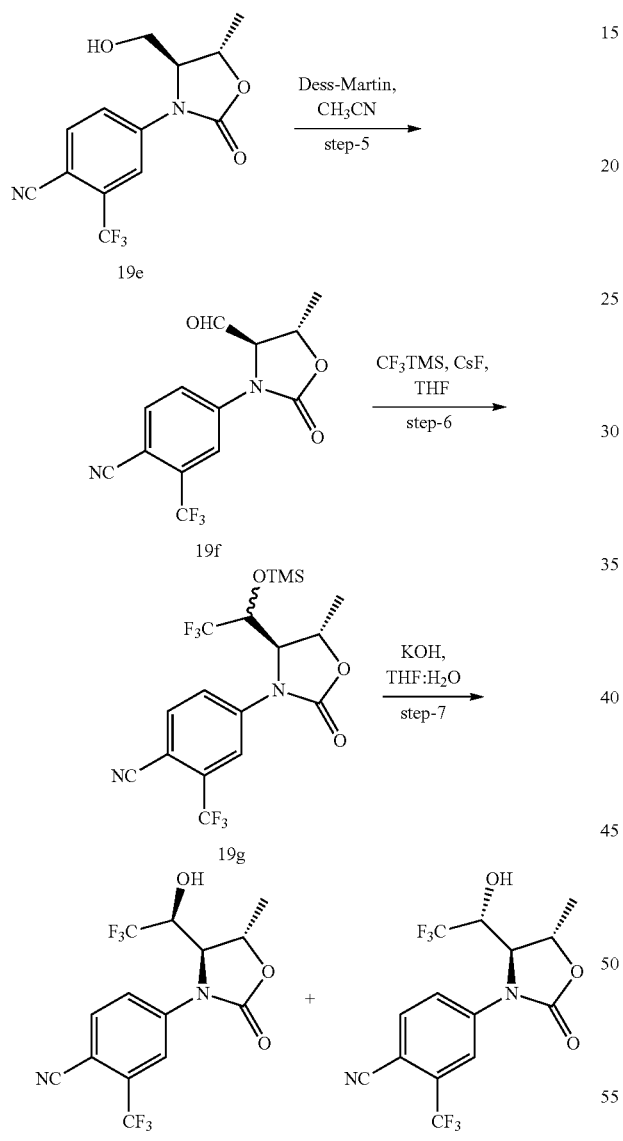

19e to 19f

To a solution of 4-((4S,5S)-4-(hydroxymethyl)-5-methyl-2-oxooxazolidin-3-yl)-2-(trifluoromethyl)benzonitrile (19e) (0.5 g, 1.66 mmol) in CH₃CN (20 mL), cooled to 0° C., Dess-Martin periodinane (1.41 g, 3.32 mmol) was added and the reaction was continued at 0° C. for 3 h. After completion of reaction (by TLC), saturated NaHCO₃ solution (50 mL) was added to the reaction mixture and extracted with CH₂Cl₂ (2×50 mL). The combined organic extracts were washed with saturated NaHCO₃ solution (50 mL). The organic layer was separated, dried over Na₂SO₄ and concentrated under reduced pressure to provide the aldehyde 19f (0.7 g) which was taken forward without purification.

TLC: 10% MeOH/DCM ($R_f$: 0.6)

19f to 19g

The crude aldehyde 19f (0.7 g, 2.35 mmol) was dissolved in THF (20 mL) and cooled to 0° C. To the reaction, CsF (0.356 g, 2.34 mmol) followed by CF₃TMS (3.3 g, 23.2 mmol) was added maintaining the temperature at 0° C. The reaction was stirred at 0° C. for 3 h and quenched with saturated NH₄Cl solution (50 mL). The reaction mixture was extracted with EtOAc (2×20 mL) and the combined organic extracts were dried over Na₂SO₄ and concentrated under reduced pressure to give the crude compound. The crude residue was passed through a short silica pad to afford the silyl ether 19g as a mixture of diastereomers (0.360 g, 24%) which was immediately used for the next step without any purification.

TLC: 30% EtOAc/Hexane ($R_f$: 0.6 & 0.8)

19g to Examples 19 and 20

To crude mixture of silyl ether 19g (0.36 g, 0.81 mmol), dissolved in THF (10 mL), KOH (0.131 g, 2.45 mmol) taken in water (5 mL) was added at 0° C. The resulting reaction mixture was stirred at 0° C. for 30 min. After completion of the reaction (by TLC), the reaction mixture was diluted with water (30 mL) and extracted with EtOAc (2×25 mL). The combined organic extracts were dried over Na₂SO₄ and concentrated under reduced pressure to give the crude mixture. The crude material was purified by column chromatography to afford 19 (0.030 g) as a white solid and 20 (0.040 g) as an off-white solid.

TLC: 50% EtOAc/Hexane ($R_f$: 0.2 19 & 0.5 20)

Example 19

¹H NMR (500 MHz, DMSO-d₆, δ in ppm): 8.23 (s, 1H), 8.19 (d, J=9.0 Hz, 1H), 8.09 (d, J=9.0 Hz, 1H), 6.98 (d, J=7.5 Hz, 1H), 4.93 (d, J=2.0 Hz, 1H), 4.70 (d, J=5.0 Hz, 1H), 4.46 (dd, J=12.0, 7.0 Hz, 1H), 1.44 (d, J=6.5 Hz, 3H).

HPLC purity: 99.68%

Mass (ESI): 481.1[M⁺+TFA]

Example 20

¹H NMR (500 MHz, DMSO-d₆, δ in ppm): 8.27-8.24 (m, 2H), 7.97 (dd, J=8.5, 2.0 Hz, 1H), 7.08 (d, J=6.5 Hz, 1H), 4.92-4.89 (m, 2H), 4.29-4.23 (m, 1H), 1.44 (d, J=6.5 Hz, 3H).

HPLC purity: 98.78%

Mass (ESI): 481.1[M⁺+TFA]

Examples 21 and 22

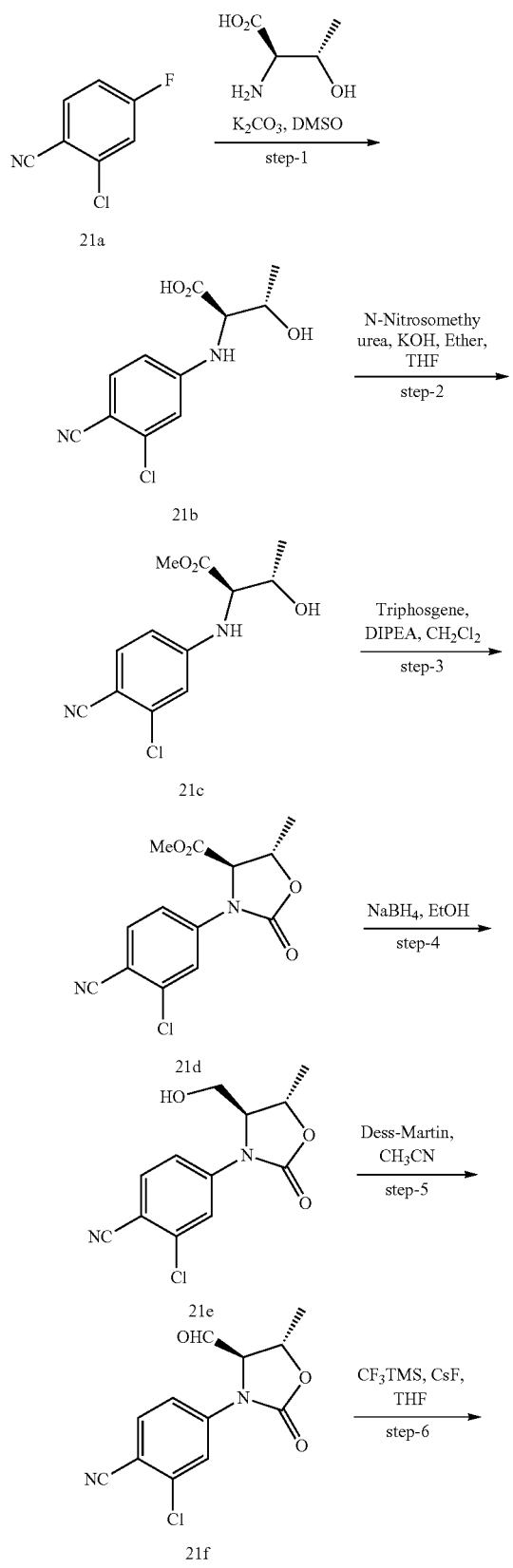

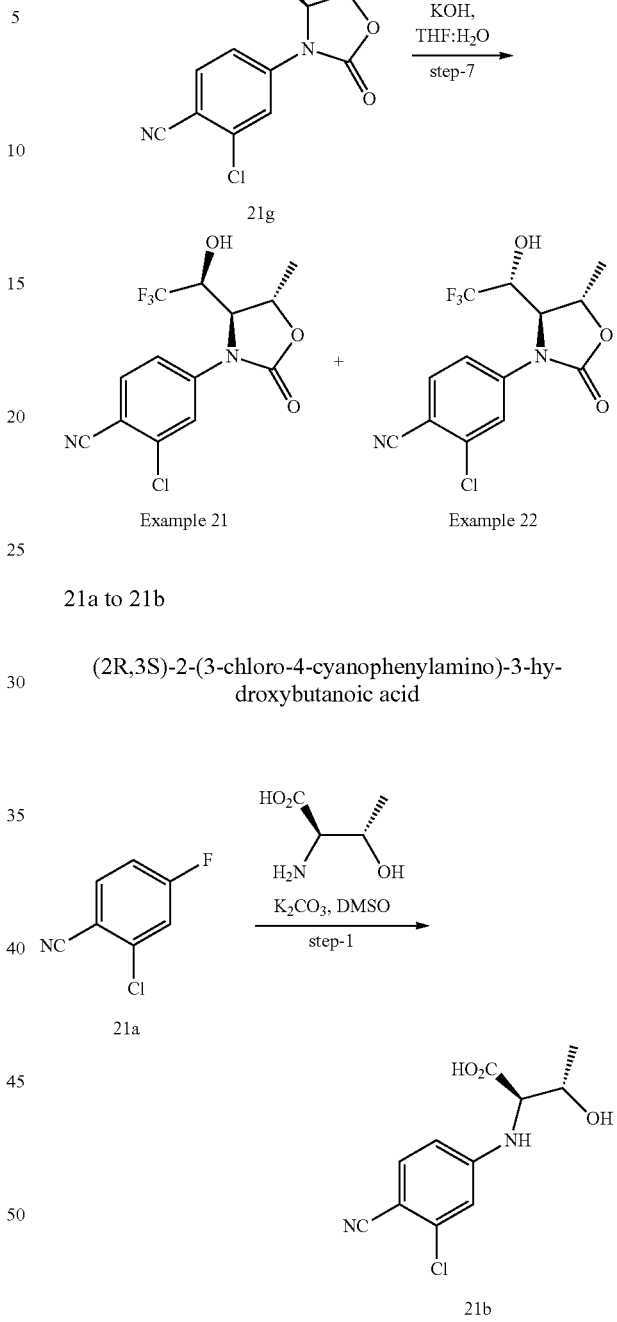

21a to 21b (2R,3S)-2-(3-chloro-4-cyanophenylamino)-3-hydroxybutanoic acid

To a solution of D-Threonine (1.7 g, 14.2 mmol) in DMSO (10 mL), K$_2$CO$_3$ (1.77 g, 12.8 mmol) followed by 2-chloro-4-fluorobenzonitrile (21a) (1.0 g, 6.43 mmol) was added at room temperature. The resulting reaction mixture was heated up to 90° C. and stirred for 16 h. After completion of reaction (by TLC), the reaction mixture was brought to room temperature, diluted with water (10 mL) and extracted with EtOAc (2×20 mL). The combined aqueous layer was acidified by citric acid (pH 3) and extracted with EtOAc (3×20 mL). The combined organic extracts were dried over Na$_2$SO$_4$ and concentrated under reduced pressure to afford the acid 21b (0.8 g, crude) as a syrup. The crude material was taken for the next step without purification.

TLC: 30% EtOAc/Hexane ($R_f$: 0.3).

$^1$H NMR (500 MHz, DMSO-$d_6$, δ in ppm): 7.52 (d, J=8.5 Hz, 1H), 6.92 (s, 1H), 6.88 (d, J=9.0 Hz, 1H), 6.73 (d, J=7.5 Hz, 1H), 4.21-4.17 (m, 1H), 4.07-4.05 (m, 1H), 3.35 (br s, 1H), 1.14 (d, J=6.5 Hz, 3H).

Mass (ESI): 253 [M$^+$-1]

21b to 21c (2R,3S)-Methyl 2-(3-chloro-4-cyanophenylamino)-3-hydroxybutanoate

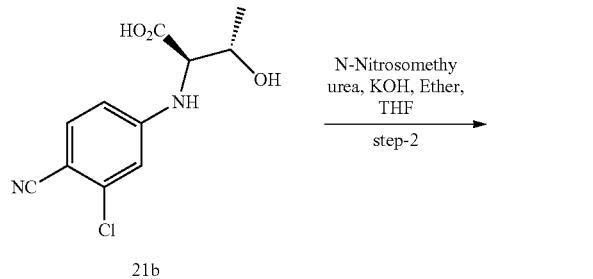

To a stirred solution of (2R,3S)-2-(3-chloro-4-cyanophenylamino)-3-hydroxybutanoic acid (21b) (0.8 g, 3.15 mmol) in THF (20 mL), diazomethane [prepared by N-Nitrosomethyl urea (0.8 g) and 40% KOH solution (30 mL) in ether (20 mL)] was added at 0° C. under nitrogen atmosphere and stirred for 30 min at 0° C. After completion of reaction (by TLC), the volatiles were evaporated under reduced pressure and the residue was diluted with water (20 mL) and extracted with EtOAc (2×20 mL). The combined organic extracts were dried over Na$_2$SO$_4$, and concentrated under reduced pressure to give crude residue which was purified by column chromatography to furnish the methyl ester 21c (0.8 g, 94%) as an off white solid.

TLC: 70% EtOAc/Hexane ($R_f$: 0.6)

$^1$H NMR (500 MHz, CDCl$_3$, δ in ppm): 7.42 (d, J=9.0 Hz, 1H), 6.69 (d, J=2.0 Hz, 1H), 6.54 (dd, J=9.0 Hz, 2.0 Hz, 1H), 5.10 (d, J=8.5, 1H), 4.34 (br s, 1H), 3.99 (dd, J=9.0 Hz, 2.5 Hz, 1H), 3.79 (s, 3H), 2.19 (d, J=4.5 Hz, 1H), 1.31 (d, J=6.5 Hz, 3H).

Mass (ESI): 269.2 [M$^+$+1]

21c to 21d (4R,5S)-Methyl 3-(3-chloro-4-cyanophenyl)-5-methyl-2-oxooxazolidine-4-carboxylate

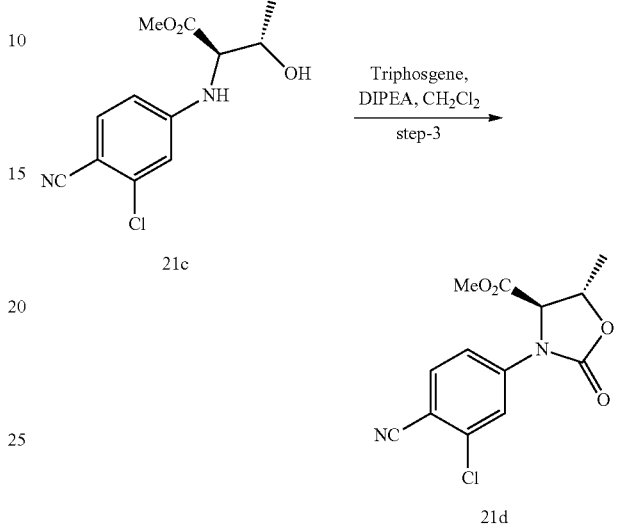

To a stirred solution of (2R,3S)-Methyl-2-(3-chloro-4-cyanophenylamino)-3-hydroxy butanoate (21c) (0.8 g, 2.98 mmol) in dry CH$_2$Cl$_2$ (30 mL), cooled to −78° C., DIPEA (1.5 mL, 9.0 mmol) followed Triphosgene (1.3 g, 4.4 mmol) in CH$_2$Cl$_2$ (10 mL) was added. The resulting reaction mixture was then slowly warmed to room temperature and stirred for 16 h. After completion of reaction (by TLC), the reaction mixture was diluted with water (30 mL) and extracted with CH$_2$Cl$_2$ (3×20 mL). The combined organic extracts were dried over Na$_2$SO$_4$ and concentrated under reduced pressure to give the crude compound. The crude material was purified by column chromatography to afford the oxazolidinone 21d (0.8 g, 95%) as a white solid.

TLC: 10% MeOH/CH$_2$Cl$_2$ ($R_f$: 0.8)

$^1$H NMR (500 MHz, DMSO-$d_6$, δ in ppm): 7.99 (d, J=8.0 Hz, 1H), 7.96 (d, J=2.0 Hz, 1H), 7.61 (dd, J=8.5 Hz, 2.0 Hz, 1H), 5.26 (d, J=3.5 Hz, 1H), 4.93 (dd, J=6.0 Hz, 3.5 Hz, 1H), 3.73 (s, 3H), 1.50 (d, J=5.5 Hz, 3H).

21d to 21e

2-Chloro-4-((4S,5S)-4-(hydroxymethyl)-5-methyl-2-oxooxazolidin-3-yl)benzonitrile

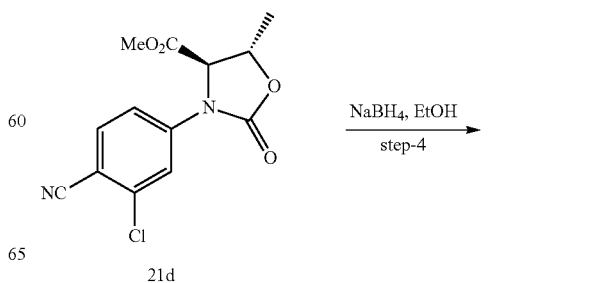

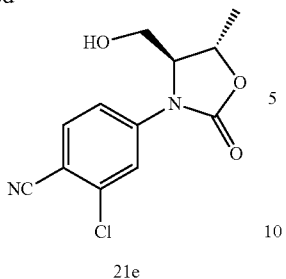

21e

To a solution of the oxazolidinone 21d (0.8 g, 2.8 mmol) in EtOH (50 mL), cooled to 0° C., NaBH$_4$ (0.120 g, 3.1 mmol) was added. The resulting reaction mixture was stirred at 0° C. for 2 h. After completion of reaction (by TLC), the volatiles were evaporated under reduced pressure and the residue was diluted with cold water (30 mL) and extracted with EtOAc (3×15 mL). The combined organic extracts were dried over Na$_2$SO$_4$ and concentrated under reduced pressure to give the crude compound. The crude material was purified by column chromatography to provide the alcohol 21e (0.7 g, 97%) as a syrup.

TLC: 50% EtOAc/Hexane (R$_f$: 0.3)

$^1$H NMR (500 MHz, DMSO-d$_6$, δ in ppm): 8.02 (d, J=2.0 Hz, 1H), 7.97 (d, J=9.0 Hz, 1H), 7.74 (dd, J=8.5 Hz, 2.5 Hz, 1H), 5.11 (t, J=5.0 Hz, 1H), 4.68-4.64 (m, 1H), 4.39-4.37 (m, 1H), 3.64-3.60 (m, 1H), 3.51-3.48 (m, 1H), 1.41 (d, J=6.5 Hz, 3H).

Mass (ESI): 266.1 [M$^+$]

21e to Examples 21 and 22

2-Chloro-4-((4S,5S)-5-methyl-2-oxo-4-((S)-2,2,2-trifluoro-1-hydroxyethyl)oxazolidin-3-yl)benzonitrile 21

2-Chloro-4-((4S,5S)-5-methyl-2-oxo-4-((R)-2,2,2-trifluoro-1-hydroxyethyl)oxazolidin-3-yl)benzonitrile 22

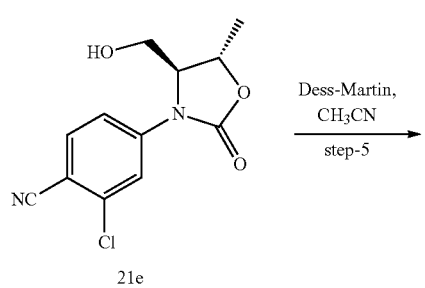

21e

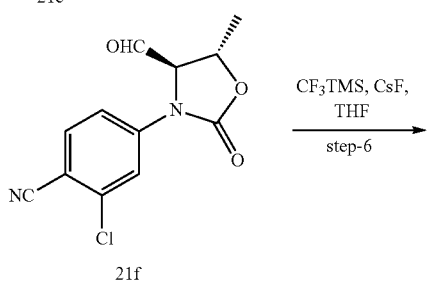

21f

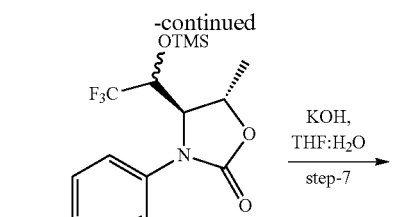

21g

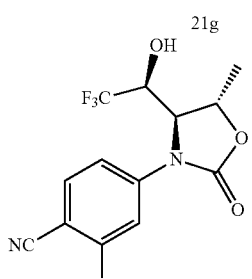

Example 21

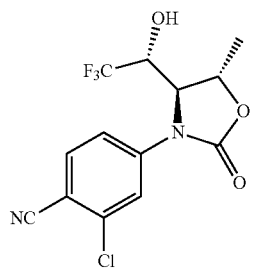

Example 22

21e to 21f

The alcohol 21e (0.7 g, 2.77 mmol) was dissolved in CH$_3$CN (50 mL) and Dess-Martin periodinane (2.3 g, 5.42 mmol) was added portion wise at 0° C. The resulting reaction mixture was slowly warmed to 15° C. and stirred for 2 h. After completion of reaction (by TLC), the reaction mixture was diluted with saturated NaHCO$_3$ solution (30 mL) and extracted with CH$_2$Cl$_2$ (3×30 mL). The combined organic extracts were again washed with NaHCO$_3$ solution (30 mL) followed by water (30 mL). The combined organic extracts were dried over Na$_2$SO$_4$, filtered and concentrated under reduced pressure to afford the aldehyde 21f (0.5 g, crude) as a syrup which was used for the next step without purification.

TLC: 10% MeOH/DCM (R$_f$: 0.8)

21f to 21g

The aldehyde 21f (0.5 g, 2.0 mmol) was dissolved in dry THF (50 mL) and CsF (0.3 g, 2.0 mmol) followed by CF$_3$-TMS (3.0 mL, 20.3 mmol) was added at 0° C. under nitrogen atmosphere. The resulting reaction mixture was stirred for 2 h at 0° C. and quenched with aqueous NH$_4$Cl solution (50 mL). The reaction mixture extracted with EtOAc (3×30 mL) and the combined organic extracts were dried over Na$_2$SO$_4$ and concentrated under reduced pressure to afford the silyl ether 21g as a mixture of diastereomers (0.7 g, crude) which was taken forward for the next step without further purification.

TLC: 50% EtOAc/Hexane (R$_f$: 0.8 & 0.9)

21g to Examples 21 and 22

To a solution of the crude silyl ether 21g (0.7 g, 1.8 mmol) in THF (50 mL), KOH (0.3 gm, 5.4 mmol) dissolved in water (50 mL) was added at 0° C. The resulting reaction mixture was stirred at 0° C. for 1 h. After completion of reaction (by TLC), the reaction mixture was diluted with water (30 mL) and extracted with EtOAc (3×20 mL). The combined organic extracts were dried over Na$_2$SO$_4$ and concentrated under reduced pressure to give the crude mixture. The crude material was purified by column chromatography to afford 21 (0.100 g) and 22 (0.100 g) both as white solids.

TLC: 50% EtOAc/Hexane ($R_f$: 0.3 21 & 0.7 22)

Example 21

$^1$H NMR (500 MHz, DMSO-$d_6$, δ in ppm): 8.0-7.98 (m, 2H), 7.78 (d, J=8.5 Hz, 1H), 6.97 (d, J=6.5 Hz, 1H), 4.82 (s, 1H), 4.75 (d, J=6.0 Hz, 1H), 4.42 (dd, J=11.5 Hz, 7.5 Hz, 1H), 1.42 (d, J=6.5 Hz, 3H).

HPLC purity: 99.43%

Mass (ESI): 333.1 [M$^+$−1]

Example 22

$^1$H NMR (500 MHz, DMSO-$d_6$, δ in ppm): 8.05 (d, J=8.5 Hz, 1H), 8.01 (s, 1H), 7.69 (d, J=9.0 Hz, 1H), 7.10 (d, J=6.0 Hz, 1H), 4.86 (d, J=6.0 Hz, 1H), 4.84 (s, 1H), 4.23-4.18 (m, 1H), 1.43 (d, J=6.0 Hz, 3H).

HPLC purity: 99.87%

Mass (ESI): 333.1 [M$^+$−1]

Examples 23 and 24

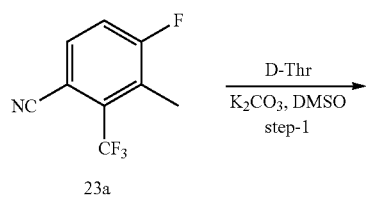

23a

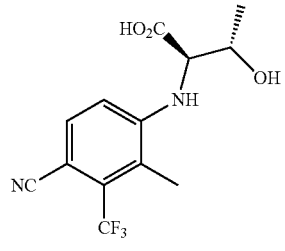

23b

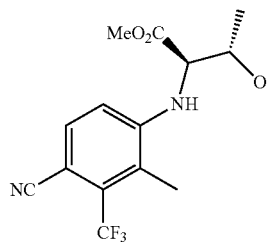

23c

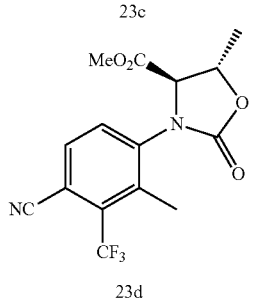

23d

-continued

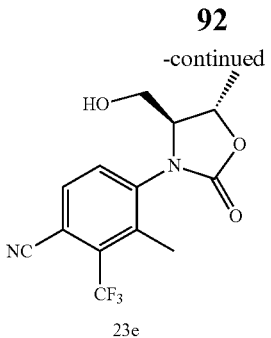

23e

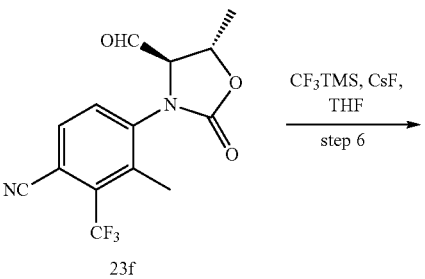

23f

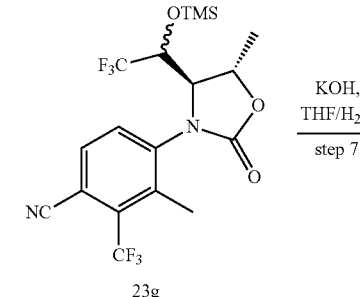

23g

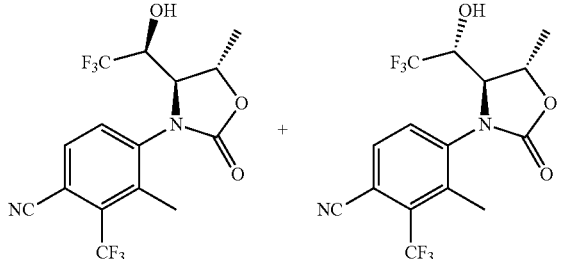

Example 23    Example 24

(2R,3S)-2-((4-cyano-2-methyl-3-(trifluoromethyl)phenyl)amino)-3-hydroxybutanoic acid 23a to 23b

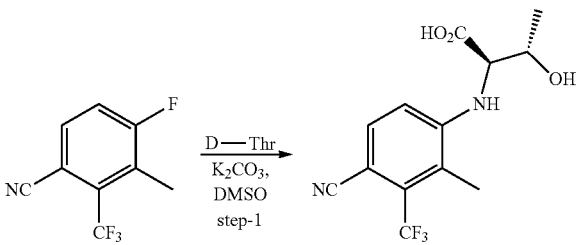

23a    23b

To a solution of D-Threonine (3.8 g, 31.9 mmol) in DMSO (30 mL) $K_2CO_3$ (4.0 g, 28.9 mmol) followed by 4-fluoro-3-methyl-2-(trifluoro methyl)benzo nitrile (23a) (3.0 g, 14.7 mmol) was added at 0° C. under nitrogen atmosphere. The resulting reaction mixture was then heated up to 80° C. for 16 h. After completion of reaction (by TLC), the reaction mixture was diluted with water (30 mL) and acidified to pH-3 using citric acid. The aqueous layer was extracted with EtOAc (3×75 mL). The combined organic extracts were washed with water (3×50 mL). The organic layer was separated dried over $Na_2SO_4$ and concentrated under reduced pressure to give the crude compound. The crude material was triturated with 10% EtOAc/hexane to afford the acid 23b (2.5 g, 57%) as white solid.

TLC: 30% $MeOH/CH_2Cl_2$ ($R_f$: 0.1)

$^1$H NMR (500 MHz, DMSO-$d_6$, δ in ppm): 7.66 (d, J=9.0 Hz, 1H), 6.86 (d, J=9.0 Hz, 1H), 5.59 (d, J=9.0 Hz, 1H), 4.27-4.25 (m, 1H), 4.18 (dd, J=8.5 Hz, 3.5 Hz, 1H), 2.27 (s, 3H), 1.20 (d, J=6.5 Hz, 3H).

Mass (ESI): 303.0 [M$^+$+1]

23b to 23c (2R,3S)-methyl 2-((4-cyano-2-methyl-3-(trifluoromethyl)phenyl)amino)-3-hydroxybutanoate

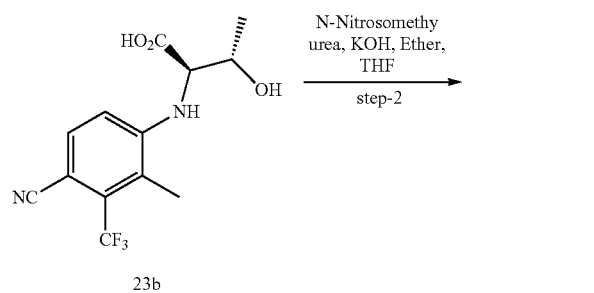

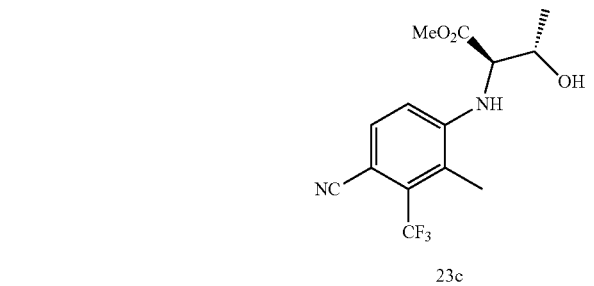

To a solution of (2R,3S)-2-((4-cyano-2-methyl-3-(trifluoromethyl)phenyl)amino)-3-hydroxybutanoic acid (23b) (2.5 g, 8.27 mmol) dissolved in THF (10 mL), cooled to 0° C., diazomethane [prepared from N-Nitrosomethyl urea (2.5 g, 24.7 mmol) and 40% KOH solution (100 mL) in ether (20 mL)] was added under nitrogen atmosphere. The reaction mixture was stirred for another 30 min at 0° C. After completion of reaction (by TLC), the reaction mixture was diluted with water (30 mL) and extracted with EtOAc (3×30 mL). The combined organic extracts were dried over $Na_2SO_4$ and concentrated under reduced pressure to provide the ester 23c (2.2 g, crude) as white solid which was pure by TLC and $^1$H NMR and therefore used for the next step without purification.

TLC: 50% EtOAc/Hexane ($R_f$: 0.6)

$^1$H NMR (500 MHz, CDCl$_3$, δ in ppm): 7.53 (d, J=8.5 Hz, 1H), 6.70 (d, J=8.5 Hz, 1H), 5.20 (d, J=8.0 Hz, 1H), 4.40-4.39 (m, 1H), 4.06 (dd, J=9.0 Hz, 3.0 Hz, 1H), 3.80 (s, 3H), 2.33 (s, 3H), 2.20 (d, J=4.0 Hz, 1H), 1.34 (d, J=6.5 Hz, 3H).

Mass (ESI): 316.9 [M$^+$+1]

23c to 23d (4R,5S)-methyl 3-(4-cyano-2-methyl-3-(trifluoromethyl)phenyl)-5-methyl-2-oxooxazolidine-4-carboxylate

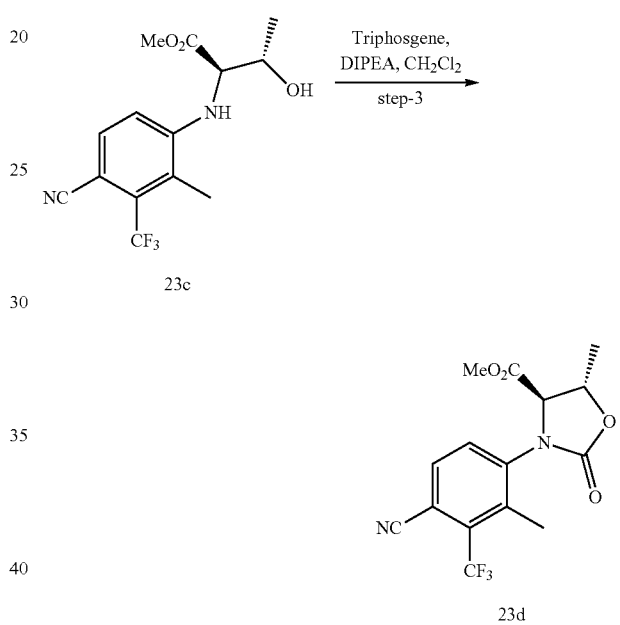

To a solution of (2R,3S)-methyl 2-((4-cyano-2-methyl-3-(trifluoromethyl)phenyl)amino)-3-hydroxybutanoate (23c) (2.2 g, 6.96 mmol) in dry $CH_2Cl_2$ (20 mL), cooled to −78° C., DIPEA (3 mL, 20.7 mmol) followed by Triphosgene (3.0 g, 10.3 mmol) dissolved in dry $CH_2Cl_2$ (10 mL) was added under nitrogen atmosphere. The resulting reaction mixture was allowed to warm to room temperature and stirred for further 16 h. After completion of reaction (by TLC), the reaction mixture was diluted with water (30 mL) and extracted with $CH_2Cl_2$ (3×50 mL). The combined organic extracts were washed with water (3×50 mL). The organic layer was separated dried over $Na_2SO_4$ and concentrated under reduced pressure to give the crude compound. The crude material was purified by column chromatography to afford the oxazolidinone 4 (2.1 g, 88%) as an off-white solid.

$^1$H NMR (500 MHz, DMSO-$d_6$, δ in ppm): 8.15 (d, J=8.5 Hz, 1H), 8.0 (d, J=8.5 Hz, 1H), 5.17 (br s, 1H), 4.95 (m, 1H), 3.60 (s, 3H), 2.40 (s, 1H), 1.6 (d, J=6.5 Hz, 3H).

TLC: 40% EtOAc/hexane (eluted twice) ($R_f$: 0.55)

Mass (ESI): 343.6 [M$^+$+1]

23d to 23e

4-((4S,5S)-4-(hydroxymethyl)-5-methyl-2-oxooxazolidin-3-yl)-3-methyl-2-(trifluoromethyl)benzonitrile

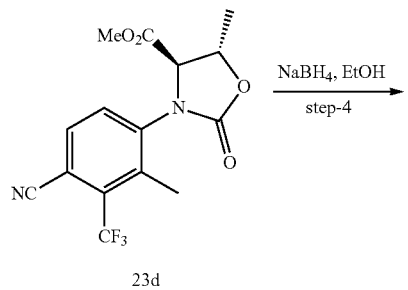

To a solution of the oxazolidinone 23d (2.1 g, 6.14 mmol) in EtOH (20 mL), cooled to 0° C., NaBH₄ (0.279 g, 7.3 mmol) was added under nitrogen atmosphere. The resulting reaction mixture was warmed to room temperature and stirred for 4 h. After completion of reaction (by TLC), the volatiles were evaporated under reduced pressure and the residue was diluted with saturated NH₄Cl solution (30 mL), stirred for 30 min at room temperature and extracted with EtOAc (3×30 mL). The combined organic extracts were dried over Na₂SO₄ and concentrated under reduced pressure to give the crude compound. The crude material was purified by column chromatography to provide the alcohol 23e (1.6 g, 84%) as an off-white solid.

TLC: 50% EtOAc/Hexane ($R_f$: 0.2)

$^1$H NMR (500 MHz, DMSO-$d_6$, δ in ppm): 8.07 (d, J=8.0 Hz, 1H), 7.92 (br s, 1H), 5.08 (br s, 1H), 4.72-4.67 (m, 1H), 4.18 (br s, 1H), 3.46-3.42 (m, 1H), 3.34-3.31 (m, 1H), 2.38 (s, 3H), 1.50 (d, J=6.0 Hz, 3H).

Mass (ESI): 315.0 [M+1]

23e to Examples 23 and 24

3-methyl-4-((4S,5S)-5-methyl-2-oxo-4-((S)-2,2,2-trifluoro-1-hydroxyethyl)oxazolidin-3-yl)-2-(trifluoromethyl)benzonitrile 3-methyl-4-((4S,5S)-5-methyl-2-oxo-4-((R)-2,2,2-trifluoro-1-hydroxyethyl)oxazolidin-3-yl)-2-(trifluoromethyl)benzonitrile

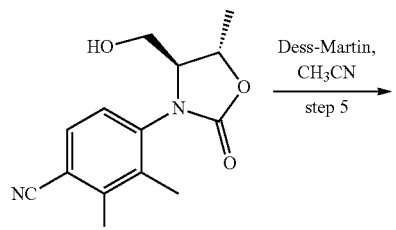

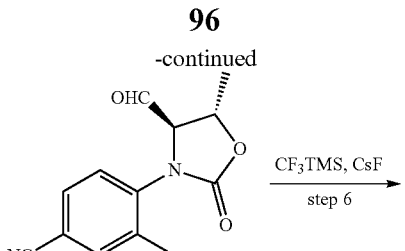

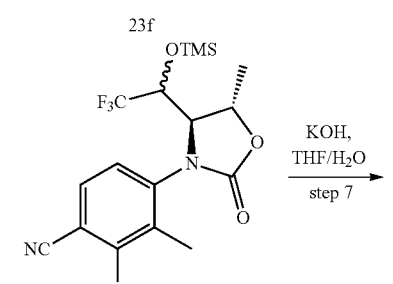

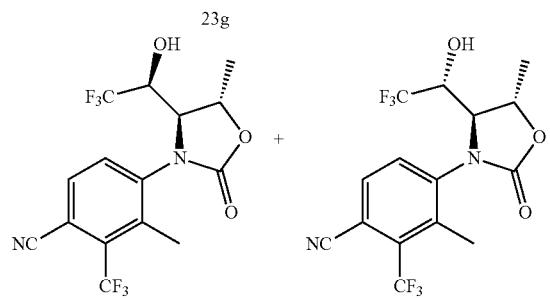

Example 23        Example 24

23e to 23f

The alcohol 23e (1.6 g, 5.1 mmol) was dissolved in CH₃CN (30 mL), cooled to 0° C., and Dess-Martin periodinane (4.8 g, 11.3 mmol) was added under nitrogen atmosphere. The resulting reaction mixture was stirred at 0° C. for 4 h. After completion of reaction (by TLC), saturated NaHCO₃ solution (50 mL) was added to the reaction mixture and extracted with CH₂Cl₂ (2×30 mL). The combined organic extracts were again washed with saturated NaHCO₃ solution (2×30 mL). The organic layer was separated, dried over Na₂SO₄ and concentrated under reduced pressure to afford the aldehyde 23f (1.2 g, crude) as a white solid. The crude material was taken to the next step without purification.

TLC: 10% MeOH/CH₂Cl₂ ($R_f$: 0.4)

23f to 23g

To the solution of the aldehyde 23f (1.2 g, 3.8 mmol) in THF (20 mL), cooled to 0° C., CsF (0.574 g, 3.8 mmol) followed by CF₃TMS (4.0 mL, 38 mmol) was added under nitrogen atmosphere. The reaction mixture was stirred at 0° C. for 3 h. After completion of reaction (by TLC), the reaction mixture was quenched with saturated NH₄Cl solution (50 mL) and extracted with EtOAc (2×50 mL). The combined organic extracts were dried over Na₂SO₄ and concentrated under reduced pressure to furnish the silyl ether 23g as mixture of diastereomers (1.0 g, crude). The crude material was carried forward for the next step without purification.

TLC: 50% EtOAc/Hexane ($R_f$: 0.8)

23g to example 23 and 24

The crude silyl ether 23g (1.0 g, 2.2 mmol) was taken in THF (20 mL), cooled to 0° C., and KOH (363 mg, 6.6 mmol) taken in water (20 mL) was added. The resulting reaction mixture was stirred at 0° C. for 30 min. After completion of reaction (by TLC), the reaction mixture was diluted with water (30 mL) and extracted with EtOAc (3×30 mL). The combined organic extracts were dried over $Na_2SO_4$ and concentrated under reduced pressure to give the crude mixture. The crude residue was purified by column chromatography to afford example 23 (0.093 g) as white solid and example 24 (0.092 g) as a light yellow solid.

TLC: 50% EtOAc/Hexane [$R_f$: Example 23 0.3 & Example 24 0.45]

Example 23

$^1$H NMR (500 MHz, DMSO-$d_6$, δ in ppm): 8.09 (br s, 1H), 8.05 (d, J=8.5 Hz, 1H), 6.98 (d, J=7.0 Hz, 1H), 4.68 (t, J=5.5 Hz, 1H), 4.49 (m, 1H), 4.41 (m, 1H), 2.42 (s, 3H), 1.55 (d, J=6.0 Hz, 3H).

HPLC purity: 94.44%

Mass (ESI): 381.2 [$M^+-1$]

Example 24

$^1$H NMR (500 MHz, DMSO-$d_6$, δ in ppm): 8.12 (m, 2H), 7.12 (br s, 1H), 4.92 (t, J=6.0 Hz, 1H), 4.58 (br s, 1H), 4.00 (t, J=7.0 Hz, 1H), 2.38 (s, 3H), 1.51 (d, J=6.0 Hz, 3H).

HPLC purity: 97.84%

Mass (ESI): 383.0 [$M^++1$]

Examples 25 and 26

4-((R)-5-((S)-2,2,2-trifluoro-1-hydroxyethyl)-3-methyl-2-oxoimidazolidin-1-yl)-2-(trifluoromethyl) benzonitrile Example 25

4-((R)-5-((R)-2,2,2-trifluoro-1-hydroxyethyl)-3-methyl-2-oxoimidazolidin-1-yl)-2-(trifluoromethyl) benzonitrile Example 26

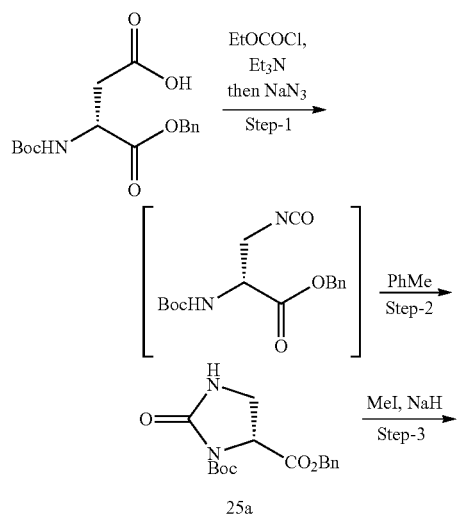
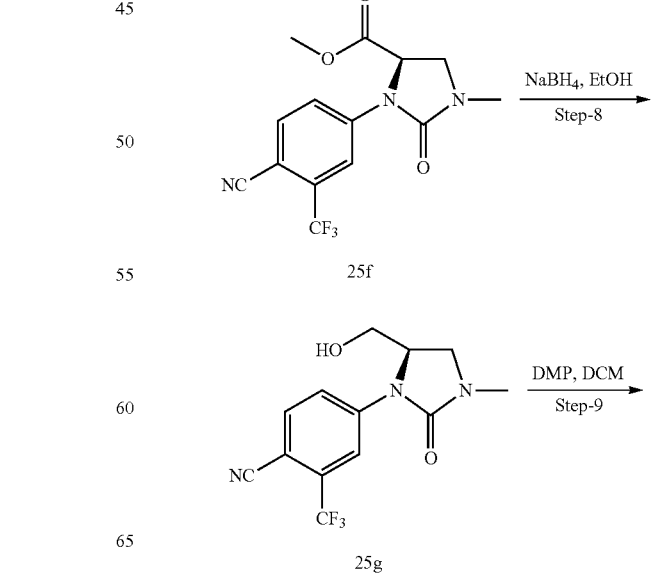

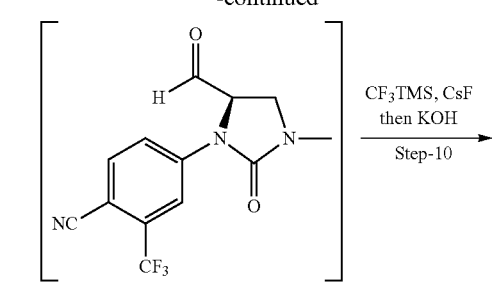

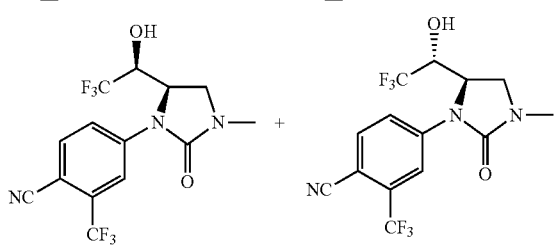

Example 25     Example 26

(R)-1-tert-butyl 5-benzyl 2-oxoimidazolidine-1,5-dicarboxylate (25a)

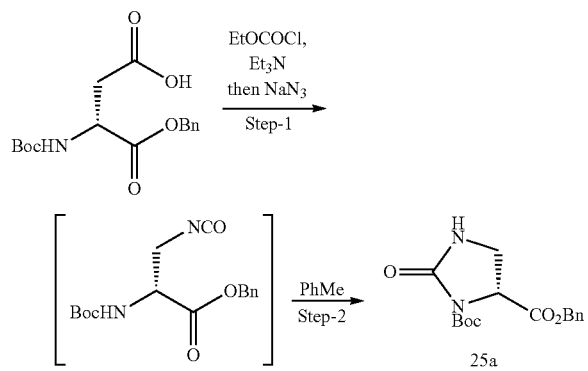

To a solution of Boc-D-Aspartic acid-1-benzyl ester (0.250 g, 0.77 mmol) taken in THF (4 mL), cooled to −10° C., Ethyl chloroformate (0.11 ml, 1.1 mmol) and TEA (0.34 ml, (2.47 mmol) was added and stirred for 30 min. NaN$_3$ (0.25 g, 0.386 mmol) was dissolved in water (4 ml) and added portion wise to the reaction mixture maintaining the temperature at −10° C. The reaction mixture was slowly warmed to room temperature and stirred for further 2 h. After completion of reaction (by TLC), the reaction mixture was poured into saturated NaCl solution and extracted with EtOAc (2×10 mL). The combined organic extracts were dried over Na$_2$SO$_4$ and concentrated under reduced pressure to half of the volume; PhMe (15 mL) was added and heated to 80° C. for 4 h. After completion (by TLC), the reaction mixture was poured into saturated NaCl solution and extracted with EtOAc (2×15 mL). The combined organic extracts were dried over Na$_2$SO$_4$ and purified by column chromatography to afford 25a (0.11 g, 44%) as a brown sold.

TLC: 80% EtOAc/Hexane (R$_f$: 0.8)

$^1$H NMR (DMSO-d6, 500 MHz): δ 7.47 (br s, 1H), 7.39-7.34 (m, 5H), 5.20 (d, J=1.5 Hz, 2H), 4.74 (dd, J=10.5, 3.5 Hz, 1H), 3.63-3.59 (m, 1H), 3.19 (dd, J=9.5, 3.0 Hz, 1H), 1.34 (s, 9H).

(R)-1-tert-butyl 5-benzyl 3-methyl-2-oxoimidazolidine-1,5-dicarboxylate (25b)

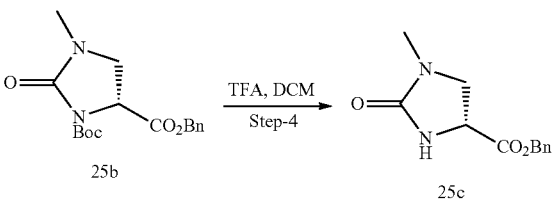 [SMILES: CN1C[C@H](C(=O)OCc2ccccc2)N(C(=O)OC(C)(C)C)C1=O ; CN1C[C@H](C(=O)OCc2ccccc2)NC1=O]

To a solution of (R)-benzyl 2-oxooxazolidine-5-carboxylate (25a) (0.1 g 0.312 mmol) in THF (2 mL), cooled to 0° C., Sodium hydride (13.9 mg, 0.37 mmol, 50% dispersion in mineral oil) was added and stirred for 60 min. MeI (0.048 g, 0.343 mmol) was added drop-wise to the reaction mixture, slowly warmed to room temperature and stirred for further 2 h. After completion (by TLC), the reaction mixture was poured into saturated NH$_4$Cl solution (10 mL) and extracted with EtOAc (2×5 mL). The combined organic extracts were dried over Na$_2$SO$_4$ and concentrated under reduced pressure to provide the crude residue which was purified by column chromatography to afford 25b (0.070 g, 67%) as a brown syrup.

TLC: 60% EtOAc/Hexane (R$_f$: 0.3)

1H NMR (DMSO-d6, 500 MHz): δ 7.39-7.35 (m, 5H), 5.20 (s, 2H), 4.71 (dd, J=10.5, 3.5 Hz, 1H), 3.64 (t, J=10.0 Hz, 1H), 3.33 (m, 1H), 2.68 (s, 3H), 1.33 (s, 9H).

(R)-benzyl 1-methyl-2-oxoimidazolidine-4-carboxylate (25c)

To a solution of (R)-1-tert-butyl 5-benzyl 3-methyl-2-oxoimidazolidine-1,5-dicarboxylate (25b) (0.650 g, 1.95 mmol) in DCM (20 mL), cooled to 0° C., TFA (3 mL, 2.9 mmol) was added. The reaction mixture was slowly warmed to room temperature and stirred for further 1 h. After completion (by TLC), the reaction mixture was neutralized with saturated NaHCO$_3$ solution and extracted with EtOAc (3×10 mL). The combined organic extracts were dried over Na$_2$SO$_4$ and concentrated under reduced pressure to provide the crude residue which was purified by column chromatography to furnish 25c (0.320 g, 70%) as off white solid.

TLC: 60% EtOAc/Hexane (R$_f$: 0.4)

1H NMR (DMSO-d6, 500 MHz): δ 7.39-7.33 (m, 5H), 6.94 (s, 1H), 5.17 (s, 2H), 4.27 (dd, J=9.5, 5.0 Hz, 1H), 3.58 (t, J=9.5 Hz, 1H), 3.99 (dd, J=8.5, 4.0 Hz, 1H), 3.16 (s, 3H).

(R)-benzyl-3-(4-cyano-3-(trifluoromethyl)phenyl)-1-methyl-2-oxoimidazolidine-4-carboxylate (25d)

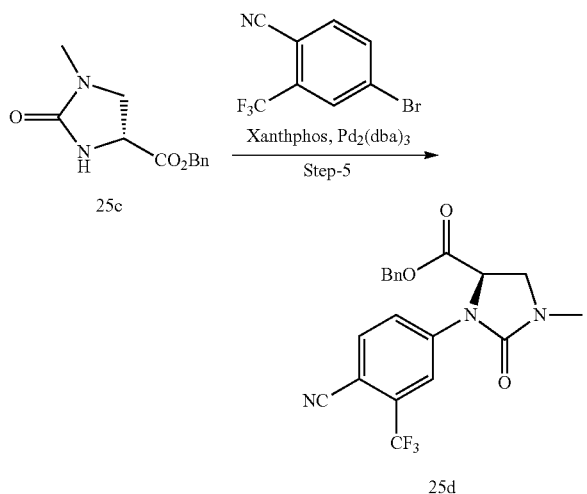

To a solution of 4-bromo-2-(trifluoromethyl)benzonitrile (0.1 g, 0.4 mmol) dissolved in 1,4-Dioxane (5 mL), (R)-benzyl 1-methyl-2-oxoimidazolidine-4-carboxylate (25c) (0.093 g, 0.4 mmol) was added at room temperature followed by Cs₂CO₃ (0.260 g, 0.8 mmol) and Argon gas was purged for 30 min. To the reaction mixture Pd₂(dba)₃ (0.036 g, 0.04 mmol) and Xanthphos (0.034 g, 0.058 mmol) were added at room temperature. The resulting reaction mixture was then heated to 100° C. for 5 h. After completion (by TLC), the reaction mixture was filtered through celite bed. The celite bed was washed with EtOAc (2×5 mL), the filtrates were combined, dried over Na₂SO₄ and concentrated under reduced pressure to give the crude compound. The crude residue was purified by column chromatography to provide 25d (0.075 g, 46%) as a colourless syrup.

TLC: 60% EtOAc/Hexane (R$_f$: 0.4)

1H NMR (DMSO-d6, 500 MHz): δ 8.35 (d, J=2.0 Hz, 1H), 8.04 (d, J=8.5 Hz, 1H), 7.75 (dd, J=9.0, 2.5 Hz, 1H), 7.34 (t, J=3.0 Hz, 3H), 7.26-7.25 (m, 2H), 5.42 (dd, J=2.5, 10.0, Hz, 1H), 5.21-5.14 (m, 2H), 3.82 (t, J=9.5 Hz, 1H), 3.64 (m, 1H), 3.80 (s, 3H).

(R)-3-(4-cyano-3-(trifluoromethyl)phenyl)-1-methyl-2-oxoimidazolidine-4-carboxylic acid (25e)

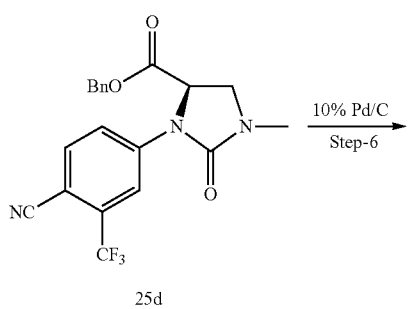

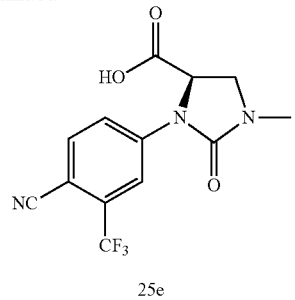

To a solution of (R)-benzyl 3-(4-cyano-3-(trifluoromethyl)phenyl)-1-methyl-2-oxoimidazolidine-4-carboxylate (25d) (0.4 g, 0.99 mmol) in MeOH (10 mL), 10% Pd/C (50 mg) was added and stirred for 2 h under H₂ atmosphere. After completion (by TLC), the reaction mixture was filtered through a celite bed, the celite bed was washed with MeOH (10 mL), the combined filtrates were concentrated under reduced pressure to provide the acid 25e (0.280 g, 90%) as a white solid.

TLC: 60% EtOAc/Hexane (R$_f$: 0.9)

¹H NMR (DMSO-d₆, 500 MHz): δ 13.6 (br s, 1H), 8.42 (s, 1H), 8.08 (d, J=8.5 Hz, 1H), 7.69 (d, J=8.0 Hz, 1H), 5.17 (dd, J=10.0, 2.5 Hz, 1H), 3.81-3.77 (m, 1H), 3.59-3.57 (m, 1H), 2.80 (s, 3H).

(R)-Methyl 3-(4-cyano-3-(trifluoromethyl)phenyl)-1-methyl-2oxoimidazolidine-4-carboxylate (25f)

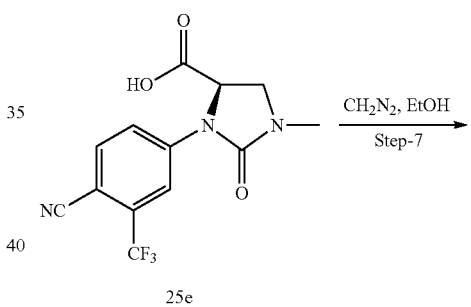

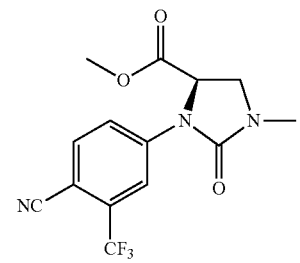

To a solution of (R)-3-(4-cyano-3-(trifluoromethyl)phenyl)-1-methyl-2-oxoimidazolidine-4-carboxylic acid (25e) (0.280 g, 0.894 mmol) in THF (10 mL), cooled to 0° C., Diazomethane [prepared from N-Nitrosomethyl urea (0.276 g, 2.68 mmol) and 40% KOH solution (15 mL) in ether (10 mL)] was added under nitrogen atmosphere. The resulting reaction mixture was warmed up to room temperature and stirred for 1 h. After completion (by TLC), the reaction mixture was poured into saturated NaCl solution and extracted with EtOAc (2×10 mL). The combined organic extracts were dried over Na₂SO₄ and concentrated under reduced pressure to provide the crude residue which was purified by column chromatography to afford the methyl ester 25f (0.210 g, 72%) as a colorless syrup.

TLC: 50% EtOAc/Hexane (R$_f$: 0.7)

1H NMR (DMSO-d6, 500 MHz): δ 8.47 (d, J=2.0 Hz, 1H), 8.08 (d, J=8.5 Hz, 1H), 7.65 (dd, J=8.5, 2.0 Hz, 1H), 5.34 (dd, J=10.0, 2.5 Hz, 1H), 3.82-3.78 (m, 1H), 3.71 (s, 3H), 3.64-3.61 (m, 1H), 2.79 (s, 3H).

2-(trifluoromethyl)-4-((R)-5-(hydroxymethyl)-3-methyl-2-oxoimidazolidin-1-yl)benzonitrile (25g)

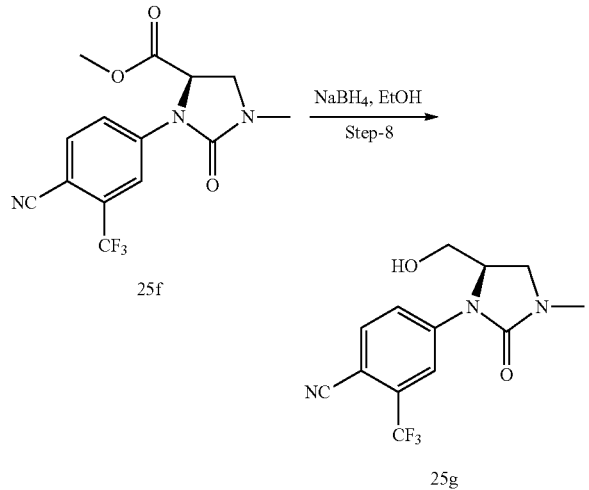

To a solution of (R)-methyl 3-(4-cyano-3-(trifluoromethyl)phenyl)-1-methyl-2-oxoimidazolidine-4-carboxylate (25f) (0.330 g, 1.01 mmol) in EtOH (20 mL), cooled to 0° C., Sodium borohydride (0.045 g, 1.21 mmol) was added portion wise maintaining the temperature at 0° C. The reaction mixture was slowly warmed to room temperature and stirred for further 6 h. After completion (by TLC) the volatiles were removed under reduced pressure and the crude residue was extracted with EtOAc (3×20 mL). The combined organic extracts were dried over Na$_2$SO$_4$ and concentrated under reduced pressure to provide the crude reaction mixture which was purified by column chromatography to afford the alcohol 25g (0.21 g, 69%) as a white solid.

TLC: 60% EtOAc/Hexane (R$_f$: 0.4)

1H NMR (DMSO-d6, 500 MHz): δ 8.49 (d, J=1.5 Hz, 1H), 8.05 (d, J=8.5 Hz, 1H), 7.83 (dd, J=9.0, 2.0 Hz, 1H), 5.04 (t, J=5.5 Hz, 1H), 4.5 (m, 1H), 3.60-3.46 (m, 3H), 3.36 (dd, J=9.0, 3.0 Hz, 1H), 2.79 (s, 3H).

4-((R)-5-((S)-2,2,2-trifluoro-1-hydroxyethyl)-3-methyl-2-oxoimidazolidin-1-yl)-2-(trifluoromethyl)benzonitrile Example 25

4-((R)-5-((R)-2,2,2-trifluoro-1-hydroxyethyl)-3-methyl-2-oxoimidazolidin-1-yl)-2-(trifluoromethyl)benzonitrile Example 26

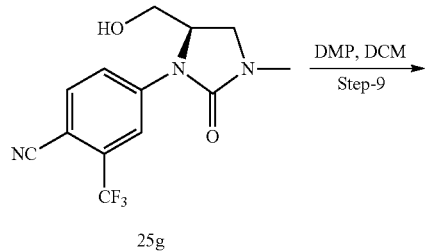

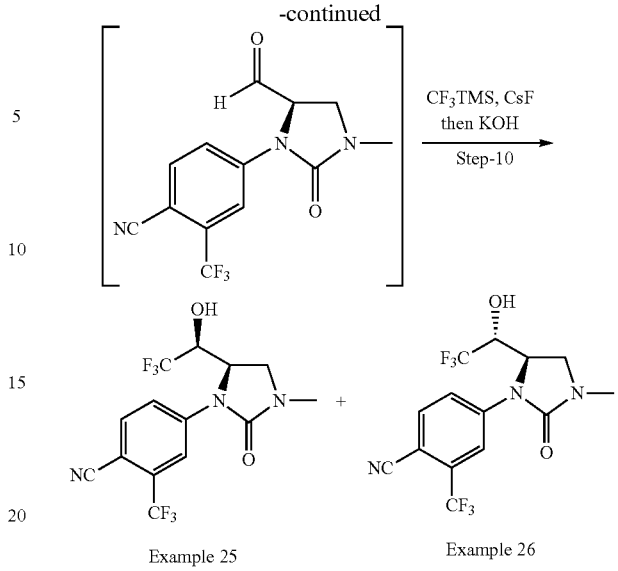

Example 25  Example 26

To a solution of 2-(trifluoromethyl)-4-((R)-5-(hydroxymethyl)-3-methyl-2-oxoimidazolidin-1-yl)benzonitrile (25g) (0.1 g, 0.33 mmol) in CH$_2$Cl$_2$ (10 mL), cooled to 0° C., Dess-Martin periodinane (0.212 g, 0.49 mmol) was added. The reaction mixture was slowly warmed to room temperature, stirred for 1 h and quenched with saturated NaHCO$_3$ solution (10 mL) and extracted with EtOAc (2×20 mL). The combined organic extracts were dried over Na$_2$SO$_4$ and concentrated under reduced pressure to provide the aldehyde (0.99 g, crude) which was carried forward to the next step without any purification.

TLC: 10% MeOH/DCM (R$_f$: 0.5)

The crude aldehyde (0.099 g, 0.33 mmol) was dissolved in dry THF (5 mL), cooled to 0° C., CsF (0.025 g, 1.49 mmol) followed by CF$_3$TMS (0.213 g, 0.166 mmol) were added and stirred for 1 h. After completion (by TLC), the reaction mixture was quenched with aqueous NH$_4$Cl and extracted with EtOAc (2×20 mL). The combined organic extracts were dried over Na$_2$SO$_4$ and concentrated under vacuo to furnish the crude silyl ether (0.147 g) as a mixture of diastereomers. The crude material was used for the next step without purification.

TLC: 50% EtOAc/Hexane R$_f$: (0.7 & 0.8)

The crude silyl ether (0.147 g, 0.334 mmol) was taken in THF (5 mL), cooled to 0° C., KOH (0.093 g, 1.67 mmol) dissolved in H$_2$O (2 mL) was added and stirred for 1 h. After completion (by TLC), the reaction mixture was diluted with H$_2$O (20 mL) and extracted with EtOAc (2×15 mL). The combined organic extracts were dried over Na$_2$SO$_4$ and concentrated under vacuo to give the crude residue which was purified by column chromatography to afford Example 25 (0.008 g) and Example 26 (0.010 g) both as white solids.

TLC: 50% EtOAc/Hexane R$_f$: 0.2 (Example 25) & 0.4 (Example 26)

Example 25

1H NMR (DMSO-d6, 500 MHz): δ 8.32 (d, J=1.5, 1H), 8.07 (d, J=8.5, 1H), 7.93-7.91 (m, 1H), 6.86 (d, J=7.0 Hz, 1H), 4.94 (t, J=7.5 Hz, 1H), 4.34-4.30 (m, 1H), 3.64 (m, 1H), 3.47 (d, J=9.5 Hz, 1H), 2.79 (s, 3H).

Example 26

1H NMR (DMSO-d6, 500 MHz): δ 8.35 (d, J=1.5 Hz, 1H), 8.14 (d, J=9.0 Hz, 1H), 7.72 (dd, J=9.0, 2.0 Hz, 1H), 6.87 (d, J=6.0 Hz, 1H), 5.02-4.99 (m, 1H), 4.25-4.22 (m, 1H), 3.60 (d, J=7.0 Hz, 2H), 2.8 (s, 3H).

The following compounds were prepared from appropriate starting materials using similar methods as in Examples 1 to 4:

Examples 27 and 28

(R)-1-(3,4-dichlorophenyl)-5-((S)-2,2,2-trifluoro-1-hydroxyethyl)pyrrolidin-2-one (Example 27) &

(R)-1-(3,4-dichlorophenyl)-5-((R)-2,2,2-trifluoro-1-hydroxyethyl)pyrrolidin-2-one (Example 28)

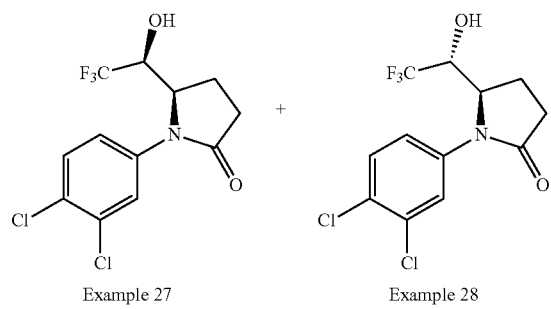 [SMILES: O=C1CC[C@H]([C@H](O)C(F)(F)F)N1c1ccc(Cl)c(Cl)c1 ; O=C1CC[C@H]([C@@H](O)C(F)(F)F)N1c1ccc(Cl)c(Cl)c1]

Example 27     Example 28

Examples 29 and 30

2-chloro-4-((R)-2-((S)-2,2,2-trifluoro-1-hydroxyethyl)-5-oxopyrrolidin-1-yl)-3-methylbenzonitrile (Example 29) &

2-chloro-4-((R)-2-((R)-2,2,2-trifluoro-1-hydroxyethyl)-5-oxopyrrolidin-1-yl)-3-methylbenzonitrile (Example 30)

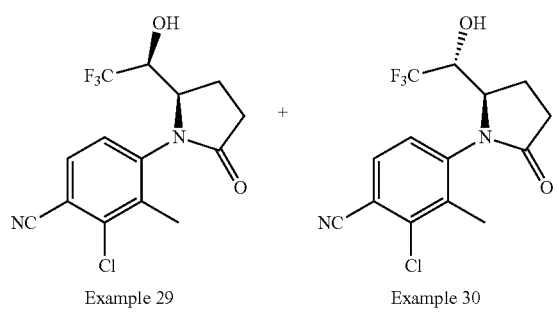 [SMILES: Cc1c(N2C(=O)CC[C@@H]2[C@H](O)C(F)(F)F)ccc(C#N)c1Cl ; Cc1c(N2C(=O)CC[C@@H]2[C@@H](O)C(F)(F)F)ccc(C#N)c1Cl]

Example 29     Example 30

Examples 31, 32, and 33

2-chloro-4-((R)-2-(2,2,2-trifluoro-1-hydroxyethyl)-5-oxopyrrolidin-1-yl)benzonitrile (Example 31), 2-chloro-4-((R)-2-((S)-2,2,2-trifluoro-1-hydroxyethyl)-5-oxopyrrolidin-1-yl)benzonitrile (Example 32) &

2-chloro-4-((R)-2-((R)-2,2,2-trifluoro-1-hydroxyethyl)-5-oxopyrrolidin-1-yl)benzonitrile (Example 33)

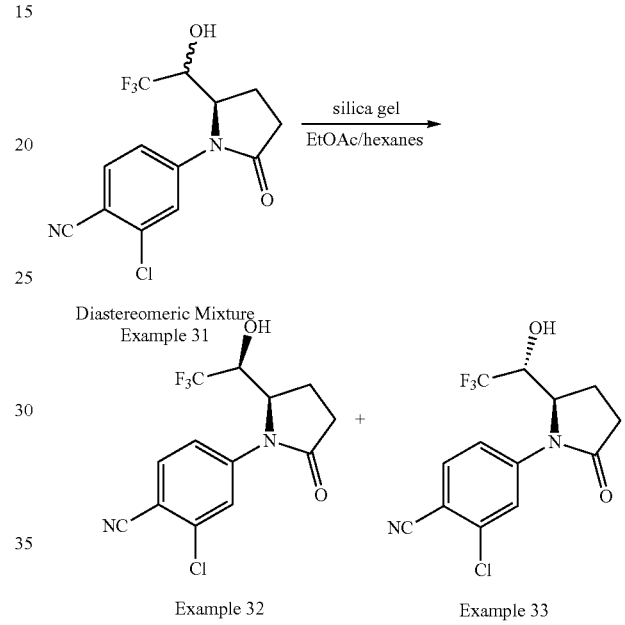

Example 32     Example 33

The following compounds were prepared from appropriate starting materials using similar methods as in Examples 7 to 24:

Examples 34 and 35

4-((4S,5R)-4-((S)-2,2,2-trifluoro-1-hydroxyethyl)-5-methyl-2-oxooxazolidin-3-yl)-2-(trifluoromethyl)-3-methylbenzonitrile (Example 34)

& 4-((4S,5R)-4-((R)-2,2,2-trifluoro-1-hydroxyethyl)-5-methyl-2-oxooxazolidin-3-yl)-2-(trifluoromethyl)-3-methylbenzonitrile (Example 35)

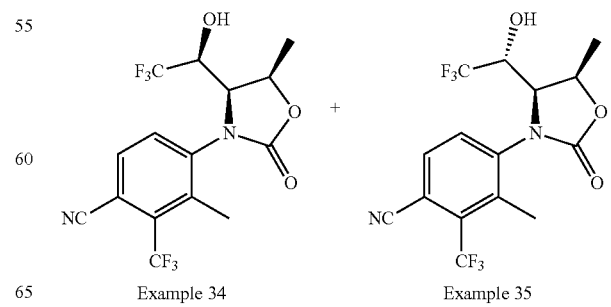

Example 34     Example 35

Examples 36 and 37

4-((4S,5R)-4-((S)-2,2,2-trifluoro-1-hydroxyethyl)-5-methyl-2-oxooxazolidin-3-yl)-2-(trifluoromethyl)benzonitrile (Example 36)

& 4-((4S,5R)-4-((R)-2,2,2-trifluoro-1-hydroxyethyl)-5-methyl-2-oxooxazolidin-3-yl)-2-(trifluoromethyl)benzonitrile (Example 37)

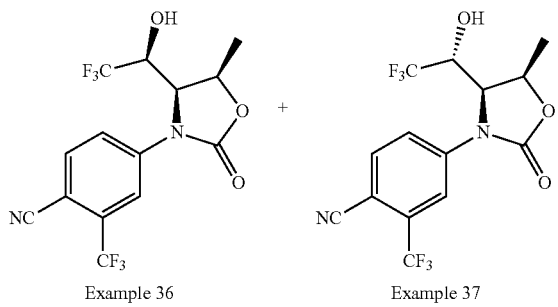 [SMILES: C[C@H]1OC(=O)N(c2ccc(C#N)c(C(F)(F)F)c2)[C@H]1[C@H](O)C(F)(F)F ; C[C@H]1OC(=O)N(c2ccc(C#N)c(C(F)(F)F)c2)[C@H]1[C@@H](O)C(F)(F)F]

Example 36        Example 37

Examples 38 and 39

2-chloro-4-((4S,5R)-4-((S)-2,2,2-trifluoro-1-hydroxyethyl)-5-methyl-2-oxooxazolidin-3-yl)benzonitrile (Example 38) &

2-chloro-4-((4S,5R)-4-((R)-2,2,2-trifluoro-1-hydroxyethyl)-5-methyl-2-oxooxazolidin-3-yl)benzonitrile (Example 39)

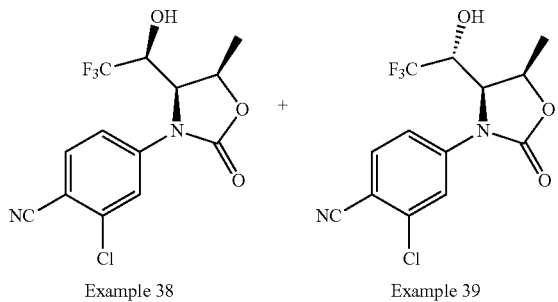 [SMILES: C[C@H]1OC(=O)N(c2ccc(C#N)c(Cl)c2)[C@H]1[C@H](O)C(F)(F)F ; C[C@H]1OC(=O)N(c2ccc(C#N)c(Cl)c2)[C@H]1[C@@H](O)C(F)(F)F]

Example 38        Example 39

Determination of Biological Activity

In order to demonstrate the utility of the compounds of this invention, an androgen receptor binding assay was performed wherein many of the compounds of this invention are shown to demonstrate significant affinity for the androgen receptor. The assay was performed as specified by the manufacturer (Invitrogen, Madison, Wis.). Briefly, 1 µl of 10 mM compound was added to 500 µl of AR screening buffer in a 1.5 ml eppendorf tube to make a $2 \times 10^{-5}$ M stock. 10-fold serial dilutions of the test compounds were prepared ranging in concentration from $10^{-5}$ M to $10^{-12}$ M. Each dilution was added in triplicate to a black 384-microtiter plate. The test compounds will be diluted 2-fold in the final reaction. 2×AR-Fluormone™ complex was prepared with 2 nM Flourmone AL Green™ and 30 nM AR. 25 µl of 2× complex was aliquoted to each reaction well, such that the final reaction volume was 50 µl per well. Plate was sealed with a foil cover and incubated in the dark at room temperature for 4 h. Polarization values for each well were measured. The polarization values were plotted against the concentration of the test compound. The concentration of the test compound that results in half-maximum shift equals the $IC_{50}$ of the test compound. As a control, a competition curve for R1881 (methyltrienolone) was performed for each assay. Curve Fitting was performed using GraphPad Prism® software from GraphPad™ Software Inc. Results are set forth in Table 1.

In Vivo Rat Model of Androgen and Anabolic Activity-Rat Herschberger Assay

The following is a typical procedure of the in vivo evaluation of the selective androgens of this invention. In particular, this assay looks primarily at the ability of the selective androgens of this invention to increase muscle size in an immature, castrated rat. In addition, androgenic effects are looked at primarily by weighing the prostate and seminal vesicles. Selective compounds will show a greater increase in the levator ani relative to the prostate and seminal vesicles when compared to testosterone treated, castrated animals or to intact animals that have not been treated. Immature Sprague Dawley male rats were obtained Charles River Laboratories (Stoneridge, N.Y.). All animals were maintained in a temperature and humidity controlled room with a 12 hr light: 12 hr dark cycle, with ad lib access to food (TD 291615, Teklad, Madison, Wis.) and water. Rats were anesthetized and orchidectomized (GDX) or sham surgery (SHAM) was performed. After a 7-day recovery period, the animals were randomized according to weight and assigned to treatment groups (n=5), SHAM, OVX+vehicle, OVX+Cpd treated. Testosterone propionate (TP 1 mg/kg in 5% DMSO/95% corn oil) was administered by once daily subcutaneous injections, while the compounds of the invention are dosed in vehicle (0.5% carboxymethylcellulose) was administered by once daily oral gavage. The rats were then dosed once daily for 4 days. All animals were euthanized via carbon dioxide inhalation 24 hs after the last dose. The prostate, seminal vesicle and levator ani and bulba cavernous (LABC) tissues were removed, weighed and recorded. An increase in mean LABC indicates anabolic activity for that particular compound with regard to oral dosing typically at a maximum tested dose of between 1 mg/kg and 30 mg/kg—see Table 1.

In Vivo Models of Bone Loss and Prevention

Compounds of this invention may also be assayed in vivo to determine their effect on preventing bone loss in animal models of bone loss. Animal models of bone loss are well-known to those of ordinary skill in the art. Examples of bone loss models include the rat and mouse ovariectomized models. Examples of such models are replete in the art, some non-limiting methods and examples are provided in Cesnjaj, et al *European Journal of Clinical Chemistry and Clinical Biochemistry* (1991), 29(4), 211-219; Y. L. Ma et al., *Japanese Journal of Bone and Mineral Research* 23 (Suppl.):62-68 (2005); Ornoy, et al, Osteoporosis: Animal Models for the Human Disease; *Animal Models of Human Related calcium Metabolic Disorders* (1995), 105-126.

TABLE 1

Compound AR-Binding Affinity and Oral Activity

| Compound | Binding $IC_{50}$ (nM) | Oral activity in Hercheberger assay on LABC weight |
|---|---|---|
| Example 1 | 14 | yes |
| Example 2 | 100 | nt |
| Example 3 | 11 | yes |
| Example 4 | 120 | nt |
| Example 5 | 530 | nt |
| Example 6 | No binding | nt |

TABLE 1-continued

Compound AR-Binding Affinity and Oral Activity

| Compound | Binding IC$_{50}$ (nM) | Oral activity in Herscheberger assay on LABC weight |
|---|---|---|
| Example 7 | 50 | yes |
| Example 8 | >1,000 | nt |
| Example 9 | 45 | yes |
| Example 10 | >1,000 | nt |
| Example 11 | 25 | yes |
| Example 12 | 933 | nt |
| Example 13 | 13 | yes |
| Example 14 | >1,000 | nt |
| Example 15 | 200 | nt |
| Example 16 | >1,000 | nt |
| Example 17 | 13 | yes |
| Example 18 | 700 | nt |
| Example 19 | 4 | yes |
| Example 20 | 72 | yes |
| Example 21 | 15 | yes |
| Example 22 | 210 | yes |
| Example 23 | 33 | nt |
| Example 24 | >1,000 | nt |
| Example 25 | 10 | no |
| Example 26 | >1,000 | no | no = no activity observed at highest dose tested.
yes = increased LABC weight relative to castrated vehicle control.
nt = not tested Additional data is presented in Table 2.

TABLE 2

| Compound | Binding IC$_{50}$ (nM) | Oral activity in Herscheberger assay on LABC weight |
|---|---|---|

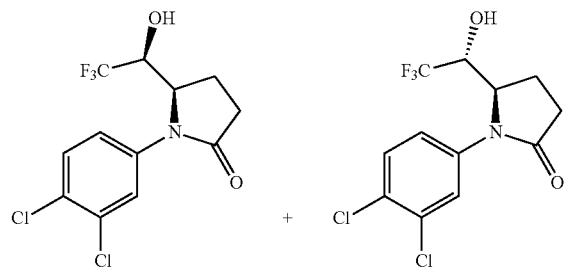

Example 27            Example 28

| Example 27 | 62 | yes |
|---|---|---|
| Example 28 | >1000 | nt |

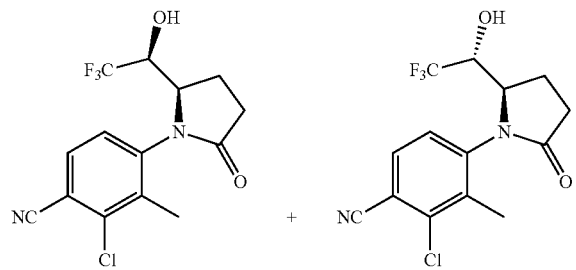

Example 29            Example 30

| Example 29 | 25 | yes |
|---|---|---|
| Example 30 | 491 | no |

TABLE 2-continued

| Compound | Binding IC$_{50}$ (nM) | Oral activity in Herscheberger assay on LABC weight |
|---|---|---|

[Diastereomeric Mixture Example 31] → silica gel, EtOAc/hexanes → [Example 32] + [Example 33]

| Example 31 | 46 | yes |
| Example 32 | nt | nt |
| Example 33 | 65 | nt |

[Example 34] + [Example 35]

| Example 34 | >1000 | nt |
| Example 35 | >10000 | nt |

[Example 36] + [Example 37]

| Example 36 | >1000 | nt |
| Example 37 | >1000 | nt |

TABLE 2-continued

| Compound | Binding IC$_{50}$ (nM) | Oral activity in Herscheberger assay on LABC weight |
|---|---|---|
| Example 38 / Example 39 | | |
| Example 38 | 150 | nt |
| Example 39 | 550 | nt |

What is claimed is:

1. A compound according to formula I:

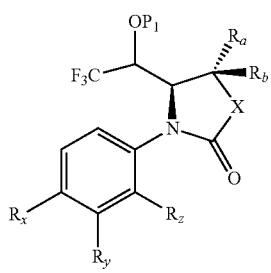

I wherein $R_x$ is CN, Cl, Br, or NO$_2$;

$R_y$ is CH$_3$, CF$_3$, or halogen;

$R_z$ is hydrogen or optionally C$_{1-3}$ alkyl, C$_{2-3}$ alkenyl, C$_{1-3}$ hydroxyalkyl, C$_{1-3}$ haloalkyl, NO$_2$, NH$_2$, OMe, halogen or OH;

P$_1$ is hydrogen or a metabolically labile group;

R$_a$ and R$_b$ are each independently selected from hydrogen or C$_1$-C$_3$ alkyl; and X is O;

or pharmaceutically acceptable salts thereof.

2. A compound according to claim 1, wherein:
R$_x$ is CN; or
pharmaceutically acceptable salts thereof.

3. A compound according to claim 1, wherein:
R$_y$ is CF$_3$ or Cl; or
pharmaceutically acceptable salts thereof.

4. A compound according to claim 1, wherein:
R$_z$ is H, CH$_3$, CF$_3$ or Cl; or
pharmaceutically acceptable salts thereof.

5. A compound according to claim 1, wherein:
R$_x$ is CN;
R$_y$ is CF$_3$ or Cl;
R$_z$ is H or CH$_3$; or
pharmaceutically acceptable salts thereof.

6. A compound according to claim 1, wherein:
P$_1$ is hydrogen or (C=O)—C$_{1-6}$alkyl; or
pharmaceutically acceptable salts thereof.

7. A compound according to claim 1, wherein:
P$_1$ is hydrogen.

8. A compound according to claim 1, wherein:
R$_a$ and R$_b$ are each independently selected from hydrogen and CH$_3$; or
pharmaceutically acceptable salts thereof.

9. A compound according to claim 1, wherein:
R$_a$ is CH$_3$ and R$_b$ is hydrogen; or
R$_a$ and R$_b$ are each hydrogen; or
pharmaceutically acceptable salts thereof.

10. A compound according to claim 1 wherein:
R$_a$ is CH$_3$ and R$_b$ is hydrogen; or
a pharmaceutically acceptable salt thereof.

11. A compound according to claim 1 wherein:
R$_a$ and R$_b$ are each hydrogen; or
a pharmaceutically acceptable salt thereof.

12. A compound according to claim 1 wherein the exocyclic stereochemical center is as shown in structure Ia below:

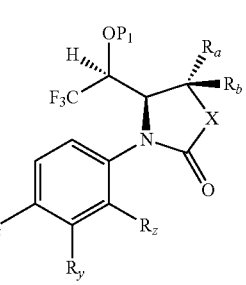

Ia or a pharmaceutically acceptable salt thereof.

13. A compound according to claim 1 wherein the exocyclic stereo chemical center is as shown in structure Ib below

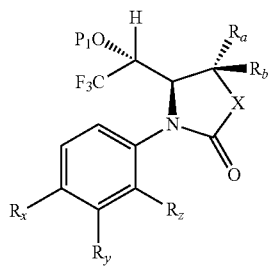

or a pharmaceutically acceptable salt thereof.

14. A compound selected from the following:
4-((R)-2-oxo-4-((R)-2,2,2-trifluoro-1-hydroxyethyl)oxazolidin-3-yl)-2-(trifluoromethyl)benzonitrile;
4-((R)-2-oxo-4-((S)-2,2,2-trifluoro-1-hydroxyethyl)oxazolidin-3-yl)-2-(trifluoromethyl)benzonitrile;
2-chloro-4-((S)-2-oxo-4-((R)-2,2,2-trifluoro-1-hydroxyethyl)oxazolidin-3-yl) benzonitrile;
2-chloro-4-((S)-2-oxo-4-((S)-2,2,2-trifluoro-1-hydroxyethyl)oxazolidin-3-yl) benzonitrile;
2-chloro-3-methyl-4-((R)-2-oxo-4-((R)-2,2,2-trifluoro-1-hydroxy ethyl)oxazolidin-3-yl)benzonitrile;
2-chloro-3-methyl-4-((R)-2-oxo-4-((S)-2,2,2-trifluoro-1-hydroxy ethyl)oxazolidin-3-yl)benzonitrile;
3-methyl-4-((R)-2-oxo-4-((R)-2,2,2-trifluoro-1-hydroxyethyl)oxazolidin-3-yl)-2-(trifluoro methyl)benzonitrile;
3-methyl-4-((R)-2-oxo-4-((S)-2,2,2-trifluoro-1-hydroxy ethyl)oxazolidin-3-yl)-2-(trifluoro methyl)benzonitrile;
2-chloro-3-methyl-4-((4S,5R)-5-methyl-2-oxo-4-((S)-2,2,2-trifluoro-1-hydroxy ethyl)oxazolidin-3-yl)benzonitrile;
2-chloro-3-methyl-4-((4S,5R)-5-methyl-2-oxo-4-((R)-2,2,2-trifluoro-1-hydroxyethyl)oxazolidin-3-yl)benzonitrile;
2-chloro-3-methyl-4-((4S,5S)-5-methyl-2-oxo-4-((R)-2,2,2-trifluoro-1-hydroxyethyl)oxazolidin-3-yl)benzonitrile;
2-chloro-3-methyl-4-((4S,5S)-5-methyl-2-oxo-4-((S)-2,2,2-trifluoro-1-hydroxyethyl)oxazolidin-3-yl)benzonitrile;
4-((4S,5S)-5-methyl-2-oxo-4-((R)-2,2,2-trifluoro-1-hydroxyethyl)oxazolidin-3-yl)-2-(trifluoromethyl)benzonitrile;
4-((4S,5S)-5-methyl-2-oxo-4-((S)-2,2,2-trifluoro-1-hydroxyethyl)oxazolidin-3-yl)-2-(trifluoromethyl)benzonitrile;
2-chloro-4-((4S,5S)-5-methyl-2-oxo-4-((R)-2,2,2-trifluoro-1-hydroxyethyl)oxazolidin-3-yl)benzonitrile;
2-chloro-4-((4S,5S)-5-methyl-2-oxo-4-((S)-2,2,2-trifluoro-1-hydroxyethyl)oxazolidin-3-yl)benzonitrile;
3-methyl-4-((4S,5S)-5-methyl-2-oxo-4-((R)-2,2,2-trifluoro-1-hydroxyethyl)oxazolidin-3-yl)-2-(trifluoromethyl)benzonitrile;
3-methyl-4-((4S,5S)-5-methyl-2-oxo-4-((S)-2,2,2-trifluoro-1-hydroxyethyl)oxazolidin-3-yl)-2-(trifluoromethyl)benzonitrile;
or a pharmaceutically acceptable salt of any of the foregoing.

15. A compound selected from the following:
4-((R)-2-oxo-4-((S)-2,2,2-trifluoro-1-hydroxyethyl)oxazolidin-3-yl)-2-(trifluoromethyl) benzonitrile;
2-chloro-4-((S)-2-oxo-4-((R)-2,2,2-trifluoro-1-hydroxyethyl)oxazolidin-3-yl) benzonitrile;
2-chloro-3-methyl-4-((R)-2-oxo-4-((S)-2,2,2-trifluoro-1-hydroxy ethyl)oxazolidin-3-yl)benzonitrile;
3-methyl-4-((R)-2-oxo-4-((S)-2,2,2-trifluoro-1-hydroxyethyl)oxazolidin-3-yl)-2-(trifluoro methyl) benzonitrile;
2-chloro-3-methyl-4-((4S, 5S)-5-methyl-2-oxo-4-((S)-2,2,2-trifluoro-1-hydroxyethyl)oxazolidin-3-yl)benzonitrile;
4-((4S,5S)-5-methyl-2-oxo-4-((S)-2,2,2-trifluoro-1-hydroxyethyl)oxazolidin-3-yl)-2-(trifluoromethyl)benzonitrile;
4-((4S,5S)-5-methyl-2-oxo-4-((R)-2,2,2-trifluoro-1-hydroxyethyl)oxazolidin-3-yl)-2-(trifluoromethyl)benzonitrile;
2-chloro-4-((4S,5S)-5-methyl-2-oxo-4-((R)-2,2,2-trifluoro-1-hydroxyethyl)oxazolidin-3-yl)benzonitrile; and
2-chloro-4-((4S,5S)-5-methyl-2-oxo-4-((S)-2,2,2-trifluoro-1-hydroxyethyl)oxazolidin-3-yl)benzonitrile or a pharmaceutically acceptable salt of any of the foregoing.

16. A pharmaceutical composition comprising a compound according to claim 1, and at least one pharmaceutically acceptable excipient.

17. A method of modulating an androgen receptor in a cell, comprising the administration of a compound according to claim 1 or a pharmaceutically acceptable salt thereof.

18. A method of identifying a compound capable of modulating an androgen receptor comprising contacting a cell expressing an androgen receptor with a compound according to claim 1, and monitoring the effect of the compound on the cell.

* * * * *